United States Patent
Stitzel

US012270042B2

(10) Patent No.: US 12,270,042 B2
(45) Date of Patent: Apr. 8, 2025

(54) METHODS FOR PREVENTING AND TREATING TYPE II DIABETES

(71) Applicant: The Jackson Laboratory, Bar Harbor, ME (US)

(72) Inventor: Michael Stitzel, Bar Harbor, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 1099 days.

(21) Appl. No.: 16/966,287

(22) PCT Filed: Jan. 31, 2019

(86) PCT No.: PCT/US2019/015958
§ 371 (c)(1),
(2) Date: Jul. 30, 2020

(87) PCT Pub. No.: WO2019/152590
PCT Pub. Date: Aug. 8, 2019

(65) Prior Publication Data
US 2020/0370068 A1 Nov. 26, 2020
US 2021/0317473 A9 Oct. 14, 2021

Related U.S. Application Data

(60) Provisional application No. 62/666,596, filed on May 3, 2018, provisional application No. 62/624,640, filed on Jan. 31, 2018.

(51) Int. Cl.
| | | |
|---|---|---|
| *C12N 15/85* | (2006.01) | |
| *A01K 67/0275* | (2024.01) | |
| *A61K 38/28* | (2006.01) | |
| *C12Q 1/6827* | (2018.01) | |
| *G01N 33/74* | (2006.01) | |

(52) U.S. Cl.
CPC ...... *C12N 15/8509* (2013.01); *A01K 67/0275* (2013.01); *A61K 38/28* (2013.01); *C12Q 1/6827* (2013.01); *G01N 33/74* (2013.01); *A01K 2227/105* (2013.01); *A01K 2267/0362* (2013.01); *C12N 2015/8527* (2013.01); *C12Q 2600/156* (2013.01)

(58) Field of Classification Search
None
See application file for complete search history.

(56) References Cited

U.S. PATENT DOCUMENTS

2015/0296757 A1  10/2015  Schüle et al.

FOREIGN PATENT DOCUMENTS

WO    WO 2012/029993 A1    3/2012

OTHER PUBLICATIONS

Cox et al. Mouse Models And the Interpretation of Human GWAS in Type 2 Diabetes and Obesity. Disease Models & Mechanisms, 2011. 4:155-164.*
Kluge et al. (2012). Pathophysiology and Genetics of Obesity and Diabetes in the New Zealand Obese Mouse: A Model of the Human Metabolic Syndrome. In: Joost, HG., Al-Hasani, H., Schürmann, A. (eds) Animal Models in Diabetes Research. Methods in Molecular Biology, vol. 933. Humana Press, Totowa, NJ. https://doi.org/.*
PCT/US2019/015958, Jul. 1, 2019, International Search Report and Written Opinion.
PCT/US2019/015958, Aug. 13, 2020, International Preliminary Report on Patentability.
International Search Report and Written Opinion mailed Jul. 1, 2019 in connection with Application No. PCT/US2019/015958.
International Preliminary Report on Patentability mailed Aug. 13, 2020 in connection with Application No. PCT/US2019/015958.
Aramburu et al., Selective inhibition of NFAT activation by a peptide spanning the calcineurin targeting site of NFAT. Mol Cell. Apr. 1998;1(5):627-37. doi: 10.1016/s1097-2765(00)80063-5.
Bernal-Mizrachi et al., Transgenic overexpression of active calcineurin in beta-cells results in decreased beta-cell mass and hyperglycemia. PLoS One. Aug. 3, 2010;5(8):e11969. doi: 10.1371/journal.pone.0011969.
Cui et al., A genome-wide association study confirms previously reported loci for type 2 diabetes in Han Chinese. PLoS One. 2011;6(7):e22353. doi: 10.1371/journal.pone.0022353. Epub Jul. 22, 2011.
Diabetes Genetics Replication and Meta-analysis (DIAGRAM) Consortium et al., Genome-wide trans-ancestry meta-analysis provides insight into the genetic architecture of type 2 diabetes susceptibility. Nat Genet. Mar. 2014;46(3):234-44. doi: 10.1038/ng.2897. Epub Feb. 9, 2014.
Dupuis et al., New genetic loci implicated in fasting glucose homeostasis and their impact on type 2 diabetes risk. Nat Genet. Feb. 2010;42(2):105-16. doi: 10.1038/ng.520. Epub Jan. 17, 2010. Erratum in: Nat Genet. May 2010;42(5):464.
Grarup et al., The diabetogenic VPS13C/C2CD4A/C2CD4B rs7172432 variant impairs glucose-stimulated insulin response in 5,722 non-diabetic Danish individuals. Diabetologia. Apr. 2011;54(4):789-94. doi: 10.1007/s00125-010-2031-2. Epub Jan. 20, 2011.
Heit et al., Calcineurin/NFAT signalling regulates pancreatic beta-cell growth and function. Nature. Sep. 21, 2006;443(7109):345-9. doi: 10.1038/nature05097.
Huyghe et al., Exome array analysis identifies new loci and low-frequency variants influencing insulin processing and secretion. Nat Genet. Feb. 2013;45(2):197-201. doi: 10.1038/ng.2507. Epub Dec. 23, 2012.

(Continued)

*Primary Examiner* — Christopher M Babic
*Assistant Examiner* — Kimberly A Aron
(74) *Attorney, Agent, or Firm* — Heather J. DiPietrantonio

(57) ABSTRACT

Provided herein, in some aspects, are methods for preventing or treating diabetes in a subject, the method comprising assaying a genomic sample obtained from the subject for an intergenic variant located in a region between a C2 calcium-dependent domain containing 4A gene (C2CD4A) and a C2 calcium-dependent domain containing 4B gene (C2CD4B), and when the intergenic variant is present in the genomic sample, administering to the subject a therapy for diabetes. Also provided herein are rodent cells homozygous for a C2cd4a mutation and/or homozygous for a C2cd4h mutation, and methods for producing the rodent cells.

4 Claims, 23 Drawing Sheets

Specification includes a Sequence Listing.

(56) References Cited

OTHER PUBLICATIONS

Keller et al., The Transcription Factor Nfatc2 Regulates β-Cell Proliferation and Genes Associated with Type 2 Diabetes in Mouse and Human Islets. PLoS Genet. Dec. 9, 2016;12(12):e1006466. doi: 10.1371/journal.pgen.1006466. PMID: 27935966; PMCID: PMC5147809.

Lawrence et al., Calcineurin/nuclear factor of activated T cells and MAPK signaling induce TNF-{alpha} gene expression in pancreatic islet endocrine cells. J Biol Chem. Jan. 14, 2011;286(2):1025-36. doi: 10.1074/jbc.M110.158675. Epub Nov. 8, 2010.

Lawrence et al., NFAT regulates insulin gene promoter activity in response to synergistic pathways induced by glucose and glucagon-like peptide-1. Diabetes. Mar. 2002;51(3):691-8. doi: 10.2337/diabetes.51.3.691.

Lawrence et al., NFAT targets signaling molecules to gene promoters in pancreatic β-cells. Mol Endocrinol. Feb. 2015;29(2):274-88. doi: 10.1210/me.2014-1066. Epub Dec. 12, 2014.

Mehta et al., Changes in the expression of the type 2 diabetes-associated gene VPS13C in the β-cell are associated with glucose intolerance in humans and mice. Am J Physiol Endocrinol Metab. Aug. 1, 2016;311(2):E488-507. doi: 10.1152/ajpendo.00074.2016. Epub Jun. 21, 2016.

Saxena et al., Genetic variation in GIPR influences the glucose and insulin responses to an oral glucose challenge. Nat Genet. Feb. 2010;42(2):142-8. doi: 10.1038/ng.521. Epub Jan. 17, 2010.

Shu et al., Identification of new genetic risk variants for type 2 diabetes. PLoS Genet. Sep. 16, 2010;6(9):e1001127. doi: 10.1371/journal.pgen.1001127.

Soleimanpour et al., Calcineurin signaling regulates human islet {beta}-cell survival. J Biol Chem. Dec. 17, 2010;285(51):40050-9. doi: 10.1074/jbc.M110.154955. Epub Oct. 13, 2010.

Strawbridge et al., Genome-wide association identifies nine common variants associated with fasting proinsulin levels and provides new insights into the pathophysiology of type 2 diabetes. Diabetes. Oct. 2011;60(10):2624-34. doi: 10.2337/db11-0415. Epub Aug. 26, 2011.

Yamauchi et al., A genome-wide association study in the Japanese population identifies susceptibility loci for type 2 diabetes at UBE2E2 and C2CD4A-C2CD4B. Nat Genet. Oct. 2010;42(10):864-8. doi: 10.1038/ng.660. Epub Sep. 5, 2010.

\* cited by examiner

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
```

<223> OTHER INFORMATION: Synthetic polynucleotide

<400> SEQUENCE: 1
agccactggt atcgtccctt                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 2
ttccaaaggg acgataccag                                               20

<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 3
ctgctgcttt gaccggctcc                                               20

<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 4
ctggatatgt taaacgtagg                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 5
cttggcatgt ccgtttagga                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 6
cctggccgtg cgcatcaagg                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 7
ccttgatgcg cacggccagg                                               20

```
<210> SEQ ID NO 8
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 8
ctgctttgac cggctcccgg                                               20

<210> SEQ ID NO 9
<211> LENGTH: 19
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (10)..(10)
<223> OTHER INFORMATION: n is a, c, g, or t

<400> SEQUENCE: 9 tgattttctcn attttaagc                                               19

<210> SEQ ID NO 10
<211> LENGTH: 11
<212> TYPE: DNA
<213> ORGANISM: Artificial Sequence
<220> FEATURE:
<223> OTHER INFORMATION: Synthetic polynucleotide

<400> SEQUENCE: 10
tttttccatt t                                                        11

<210> SEQ ID NO 11
<211> LENGTH: 11
<212> TYPE: DNA
<213> ORGANISM: Artificial Sequence
<220> FEATURE:
<223> OTHER INFORMATION: Synthetic polynucleotide

<400> SEQUENCE: 11
tttttctatt t                                                        11

<210> SEQ ID NO 12
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 12
tttttccccc                                                          10

<210> SEQ ID NO 13
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 13
ctgtccctag tgccaagaca ttggaaagaa gccagacgtc a                       41

<210> SEQ ID NO 14
<211> LENGTH: 41
<212> TYPE: DNA
```

```
<213> ORGANISM: Artificial Sequence
<220> FEATURE:
<223> OTHER INFORMATION: Synthetic polynucleotide

<400> SEQUENCE: 14
tcatccttcc tcgccttccc gggtcccggg gcgacgagcg c                    41

<210> SEQ ID NO 15
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 15
tgatttttcy attttaagc                                             19

<210> SEQ ID NO 16
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 16

Val Ile Val Ile Thr
1               5
```

METHODS FOR PREVENTING AND TREATING TYPE II DIABETES

RELATED APPLICATIONS

This application is a national stage filing under 35 U.S.C. § 371 of international application number PCT/US2019/015958, filed Jan. 31, 2019, which was published under PCT Article 21(2) in English and claims the benefit under 35 U.S.C. § 119(e) of U.S. provisional application No. 62/624,640, filed Jan. 31, 2018, and U.S. provisional application No. 62/666,596, filed May 3, 2018, each of which is incorporated by reference herein in its entirety.

GOVERNMENT LICENSE RIGHTS

This invention was made with government support under R01 DK117137A awarded by National Institute of Diabetes and Digestive and Kidney Diseases, National Institutes of Health and under W81XWH-18-1-0401 awarded by Department of Defense. The government has certain rights in the invention.

REFERENCE TO AN ELECTRONIC SEQUENCE LISTING

The content of the electronic sequence listing (J022770011US02-SUBSEQ-NTJ.txt; Size: 3,570 bytes; and Date of Creation: Dec. 22, 2023) is herein incorporated by reference in its entirety.

BACKGROUND

Type 2 diabetes (T2D) is characterized by dysfunction in pancreatic islet cells resulting in insulin resistance and elevated blood glucose levels. Genome-wide association studies (GWAS) have identified >150 loci associated with T2D and diabetes-related glycemic traits such as fed and fasting glucose and insulin levels[1]. The prevailing model that has emerged from collective analyses is that islet dysfunction plays a major role in T2D genetic risk[2]. Protein-coding variants have been implicated as the most likely causal variants for only a handful of loci[3]. Thus, the large majority of SNPs identified by T2D GWAS likely reside in non-coding, regulatory regions of the genome. Identifying the causal variant(s), target gene(s), and direction-of-effect for each of these loci are important steps to translate GWAS results into mechanistic understanding of islet gene regulation and T2D pathogenesis and to identify and develop new therapeutic targets and strategies[4].

SUMMARY

Provided herein, in some embodiments, are cells and transgenic animals (and methods for producing these cells and animals) for use, for example, as models for the assessment of diabetes and associated conditions. Also provided herein, in other aspects, are methods for assessing risk, diagnosing, preventing, and/or treating diabetes. The technology as provided herein is based, at least in part, on genome-wide association studies (GWAS) and functional genomics approaches that have implicated enhancer disruption in islet dysfunction and type 2 diabetes (T2D) genetic risk. The present disclosure describes genetic fine-mapping and functional (epi)genomic approaches to a T2D-associated and proinsulin-associated locus on q22.2 to identify a causal variant, determine its direction-of-effect, and elucidate plausible target genes. Fine-mapping and conditional analyses of proinsulin levels of 8,635 non-diabetic individuals from the METSIM study support a single association signal represented by a cluster of sixteen strongly associated ($p<10^{-17}$) variants in high linkage disequilibrium ($r^2>0.8$) with the GWAS index SNP rs7172432. These variants reside in an evolutionarily and functionally conserved islet/beta cell stretch/super enhancer (SE); the most strongly associated variant (rs7163757, $p=3\times10^{-19}$) overlaps a conserved islet open chromatin site. DNA sequence containing the rs7163757 risk allele displayed two-fold higher enhancer activity than the non-risk allele in reporter assays ($p<0.01$) and was differentially bound by beta cell nuclear extract proteins. The nuclear factor of activated T cells (NFAT) transcription factor specifically potentiated risk allele enhancer activity and altered patterns of nuclear protein binding to the risk allele in vitro, suggesting it may be a factor mediating risk allele effects. Unexpectedly, the rs7163757 proinsulin-raising and T2D risk (C) allele was associated with increased human islet C2CD4B expression and possibly C2CD4A expression, both of which were induced by diabetogenic inflammatory islet stressors. Together, these data suggest that the rs7163757 risk allele contributes to genetic risk of islet dysfunction and T2D by increasing NFAT-mediated islet enhancer activity and modulating C2CD4B, and likely C2CD4A, expression.

Thus, some aspects of the present disclosure provide cells comprising a modification in at least one allele of a C2 calcium-dependent domain containing 4A (C2cd4a) gene, in at least one allele of a C2 calcium-dependent domain containing 4B (C2cd4b) gene, or in a least one allele of a C2cd4a gene and in at least one allele of a C2cd4b gene. In some aspects, the present disclosure provides a (at least one) cell in a transgenic animal (e.g., a rodent, such as a mouse), the cell comprising a modification in at least one allele of a C2cd4a gene, in at least one allele of C2cd4b gene, or in a least one allele of a C2cd4a gene and in at least one allele of a C2cd4b gene. In some embodiments, the modification is a deletion.

Some aspects of the present disclosure provide cells comprising an inactivated C2cd4a allele, an inactivated C2cd4b allele, or an inactivated C2cd4a allele and an inactivated C2cd4b allele. In some aspects, the present disclosure provides a (at least one) cell in a transgenic animal (e.g., a rodent, such as a mouse), the cell comprising an inactivated C2cd4a allele, an inactivated C2cd4b allele, or an inactivated C2cd4a allele and an inactivated C2cd4b allele.

In some embodiments, the genotype of the cell is C2cd4a$^{-/-}$. In other embodiments, the genotype of the cell is C2cd4b$^{-/-}$. In yet other embodiments, the genotype of the cell is C2cd4a$^{-/-}$/C2cd4b$^{-/-}$.

Other aspects of the present disclosure provide a transgenic mouse that comprises an inactivated C2cd4a allele, an inactivated C2cd4b allele, or an inactivated C2cd4a allele and an inactivated C2cd4b allele.

Also provided herein, in some aspects, are methods of producing C2cd4a$^{-/-}$,C2cd4b$^{-/-}$, or C2cd4a$^{-/-}$/C2cd4b$^{-/-}$ rodent cells and animals (e.g., rodents, such as mice).

Further aspects of the present disclosure provide methods for preventing or treating diabetes. In some embodiments, the methods comprise assaying a genomic sample obtained from a subject for a single nucleotide polymorphism (SNP) selected from rs4502156 allele (T), rs1881415 allele (T), rs67818839 allele (A), rs7162757 allele (C), rs8037894 allele (G), rs8038040 allele (G), rs6494307 allele (C), rs7161785 allele (G), rs7167878 allele (C), rs7167932 allele (C), rs7172432 allele (A), rs7173964 allele (G), rs4775466 allele (C), rs4775467 allele (G), rs10083587 allele (C), and rs11856307 (A). In some embodiments, when the SNP is present in the genomic sample, the methods further comprise diagnosing the subject as having diabetes or as at risk of diabetes. In some embodiments, when the SNP is present in the genomic sample, the methods further comprise administering to the subject a therapy (e.g., for insulin resistance) to prevent or treat diabetes in the subject.

In other embodiments, the methods comprise assaying a genomic sample obtained from a subject (e.g., a human subject) for an intergenic variant located in a region between a C2CD4A gene and a C2CD4B gene, and measuring a level of proinsulin in a biological sample obtained from the subject.

In some embodiments, when the intergenic variant is present in the genomic sample and the level of proinsulin in the biological sample is greater than 20 pmol/L (e.g., 25 pmol/L, 30 pmol/L, 35 pmol/L, 40 pmol/L, 45 pmol/L, or 50 pmol/L), the method further comprises administering to the subject a therapy (e.g., for insulin resistance) to prevent or treat diabetes in the subject.

BRIEF DESCRIPTION OF DRAWINGS

(FIG. 1A) Locus Zoom plot showing association of genetic variants with increased proinsulin levels in the VPS13C/C2CD4A/C2CD4B locus in the Metabolic Syndrome in Men (METSIM) study population. The arrow points to the index SNP (rs7172432). X-axis displays the gene and variant position on Chromosome 15 (chr15) in megabases (Mb). Y-axis indicates association p-values (left) and recombination rate (right) in centiMorgans (cM). Associated variants reside between two intergenic recombination hotspots (peaks) between C2CD4A and C2CD4B. (FIG. 1B) Locus Zoom plot of proinsulin association in the locus after conditioning on rs7172432. X- and Y-axes are as described in (A).

(FIG. 2B) mouse MIN6 beta cells; and (FIG. 2C) rat INS-1(832/13) beta cells. RefSeq Genes indicate the location of C2CD4A, C2CD4B and VPS13C genes in the region. Increased low/no signal states in 832/13 is due to low mappability. Sixteen proinsulin associated variants are indicated (upper panel) in A. Genome Browser coordinates correspond to hg19, mm9, and rn5 respectively.

(FIG. 4A) UCSC Genome Browser view of islet stretch/super enhancer (SE) constituent HS3. Islet transcription factor (Islet TFs) ChIP-seg[16], ATAC-seq pileup and cross-species sequence conservation (seq. cons.) are indicated. Proinsulin- and T2D-associated rs7163757 (C/T) is indicated by light gray shading and font. DNA sequence cloned and tested for enhancer activity is indicated. Genome browser coordinates correspond to hg19. (FIG. 4B) Luciferase reporter assay of HS3 sequence (cloned in forward and reverse orientations) containing the rs7163757 risk allele (C) or non-risk alleles (T) (haplotype 1 and 2 respectively) and (C) allele mutated to (T) allele (C:T) and vice versa (T:C). All luciferase activity is normalized to that of empty vector. HS3 enhancer activity is compared to the normalized activity of pGL4.23 vector containing Gateway sequence in the forward and reverse orientations. All cloned HS3 enhancer sequences are significantly more active than the control vectors (p-values not indicated). p-values are indicated for HS3 (C) allele versus (T) allele, (T) versus (T:C), (C) versus (C:T) and (T:C) versus (C:T) in forward and in reverse orientation. The mutated alleles (T:C) versus (C) and (C:T) versus (T) are not significantly different (p-values not indicated). Each construct was measured in triplicate; a total of 16 biological replicates were measured per haplotype over seven independent experiments. Data represent the mean±SEM; ,* indicate $p<0.01$, $<0.001$, respectively, according to two-sided unpaired t-test.

(FIG. 5A) Box plots of C2CD4B, C2CD4A, and VPS13C expression (PEER-adjusted, inverse-normalized FPKM) in 112 human islets, grouped by rs7163757 genotype. Dots indicate FPKM values from FUSION and Groop islet cohorts, respectively; * indicates genome-wide significant association. (FIG. 5B) Schematic depicting principles of AEI. Heterozygous regulatory SNP (rSNP) genotype leads to expression imbalance of the transcribed SNP (tSNP) in RNA-seq data for genes regulated by the rSNP (left side of the schematic). Homozygous rSNP genotype manifests as equivalent transcription both tSNP alleles. (FIG. 5C) AEI between rSNP rs7163757 and tSNPs in C2CD4A and VPS13C in FUSION human pancreatic islet RNA-seq data. Number (n) of samples with heterozygous (Het) and homozygous (Hom) rs7163757 genotypes is shown on the x-axis. Absolute value of allelic imbalance for each tSNP is indicated on the y-axis; * denotes q<0.05, two-sided Wilcoxon Rank Sum Test adjusted for multiple testing (see Methods). C2CD4A, not VPS13C, exhibits rs7163757 genotype-dependent allelic imbalance as depicted schematically in B. (FIGS. 5D-5F) C2CD4A, C2CD4B, and VPS13C expression in (FIG. 5D) human islets before and after IL-1ß (IL) and IFN-7 (IFN) exposure[46], (FIG. 5E) rat islets exposed to 0, 0.1, or 20 ng/mL IL-1ß[47], or (FIG. 5F) INS-1(832/13) cells exposed to 2 U/ml IL-1ß for 2 hours. Box plots represent fold change in expression (RPKM) relative to untreated controls. * indicates p<0.05, Wilcoxon rank sum test.

(FIG. 6A) PWM scores (Haploreg) identify NFAT as the most plausible transcription factor binding to the risk allele (C), but not to the non-risk allele (T), of rs7163757. Sequence is shown for the risk allele ("R") (SEQ ID NO: 10) and the non-risk allele ("NR") (SEQ ID NO: 11) indicating the affected position in the NFAT binding motif. (FIG. 6B) Islet NFAT footprints. Density plots indicate normalized sequence coverage of ATAC-seq at the NFAT motifs predicted as bound, which include the rs7163757 site, or unbound in two human islet samples. (FIG. 6C) Luciferase reporter assay of HS3 (cloned in forward orientation) containing the rs7163757 risk allele (C) or non-risk allele (T) in MIN6 cells treated with 10 ng/ml Tacrolimus (Tac) or ethanol control (Vehicle). Between four and five biological replicates were measured in three independent experiments. Luciferase activity of HS3 constructs are normalized to the corresponding vehicle control- and Tacrolimus-treated pGL4.23 empty vector. Bars represent mean luciferase activity ±SEM; *, , * indicate p<0.05, <0.01, <0.001 (unpaired two-sided t-test), respectively. (FIG. 6D) Luciferase reporter assay of HS3 (cloned in forward and reverse orientations) containing the rs7163757 risk allele (C) or non-risk allele (T) in the presence of EGFPC1-huNFATc1EE-WT or the NFAT inhibitor construct EGFPN1-VIVIT (SEQ ID NO: 16). pGL3-NFAT-Luciferase (NFAT-Reporter), containing three canonical NFAT binding sites upstream of a luciferase reporter, plus EGFP plasmid serves as a control for NFAT activity of the expression constructs. For all cloned HS3 enhancer sequences co-transfected with EGFP/EGFPC1-huNFATc1EE-WT/EGFPN1-VIVIT (SEQ ID NO: 16) eight biological replicates were measured in four independent experiments. Luciferase activity of NFAT expression constructs are normalized to NFAT-Reporter plus EGFP. Luciferase activity of HS3 expression constructs with EGFP or NFAT expression constructs are normalized to pGL4.23 empty vector with EGFP or NFAT expression constructs, respectively. NFAT Rep. =pGL3-NFAT-Luciferase, HS3-F and HS3-R denote the HS3 sequence ((C) or (T) allele) cloned into pGL4.23 in the forward or reverse orientations respectively. G=EGFP, N=EGFPC1-huNFATc1EE-WT, V=EGFPN1-VIVIT (SEQ ID NO: 16). Bars represent mean luciferase activity+/− SEM; *, , * indicate p<0.05, <0.01, <0.001 (unpaired two-sided t-test), respectively. (FIG. 6E) Allele-specific protein binding of sequences containing different rs7163757 alleles. Electrophoretic mobility shift assay (EMSA) with biotin-labeled probes containing either the rs7163757 (T) or (C) allele incubated with MIN6 nuclear extract (NE). Black arrows indicate allelic differences in protein binding. Gray arrows show non-specific binding or no clear differences between alleles. Bands labeled 'b', 'c' and 'd' indicate proteins that bind specifically to the (C) allele. Asterisk in lane 9 indicates disruption of band 'c' by NFATc2 antibody. Asterisks in lanes 5 and 10 indicate supershift of non-allele specific band 'a' by YY1 antibody.

(FIGS. 7A, 7B) UCSC Genome Browser views of the C2cd4a (FIG. 7A) and C2cd4b (FIG. 7B) loci in the rat genome (rn5 genome build). Guide RNA (gRNA) target sites are indicated by black lines; each region expected to be deleted by each gRNA pair is indicated by the gray box. ATAC-seq tracks indicate open chromatin sites, which were used as a reference to ensure upstream gRNAs deleted the whole promoter/transcription start site. RNA-seq tracks show C2CD4A (FIG. 7A) and C2CD4B (FIG. 7B) expression in wild type, C2cd4a$^{-/-}$, C2cd4b$^{-/-}$ and C2cd4a$^{-/-}$; C2cd4b$^{-/-}$ clones. (FIG. 7C) Reverse transcriptase-quantitative PCR (RT-qPCR) analyses of C2cd4a, C2cd4b and Vps13c gene expression in wildtype and deletion mutants. Expression of each transcript was normalized to Gapdh using the delta Ct method. Mean values ±SEM of each gene's expression relative to wild type is plotted. Expression from three clones per genotype was measured on two separate occasions. *, p<0.01, unpaired Student's t-test. (FIG. 7D) ELISA measurements of insulin secretion from wild type and mutant cells exposed to 3 mM or 15 mM glucose. Each mutant exhibited comparable basal (3 mM) insulin secretion levels. Double mutants exhibited impaired GSIS, as indicated by lower insulin secretion in cells exposed to 15 mM glucose. Insulin secretion (ng) was normalized to total protein content (mg) in the paired cell lysate for each clone. Data are plotted as mean±SEM of three clones per genotype, and GSIS experiments were completed on five separate occasions. *, p<0.0005, unpaired Student's t-test.

(FIG. 8A) Cartoon depicting dual-plasmid approach to generate and monitor CRISPR/Cas9 deletions. (FIG. 8B) Schematic of experimental design to create, isolate, and screen/identify CRISPR/Cas9 C2cd4a, C2cd4b, and C2cd4a; C2cd4b INS-1(832/13) deletion mutants. (FIG. 8C) Image of INS-1(832/13) co-transfected with eGFP and mCherry CRISPR/Cas9 plasmids. (FIG. 8D-FIG. 8G) PCR genotyping of wildtype, each single gene deletion, and double deletion mutants using external primers flanking the C2cd4a (FIG. 8D) and C2cd4b (FIG. 8E) regions targeted for deletion and primers in the C2cd4a (FIG. 8F) and C2cd4b (FIG. 8G) regions deleted. (FIG. 8H, FIG. 8I) Representative Sanger sequence traces of C2cd4a (FIG. 8H) and C2cd4b (FIG. 8I) deletion breakpoints in single and double gene deletion clones. Arrows indicate the deletion breakpoints in each locus. FIG. 8H and FIG. 8I show SEQ ID NOs: 13 and 14, respectively.

DETAILED DESCRIPTION

Figure 1A:
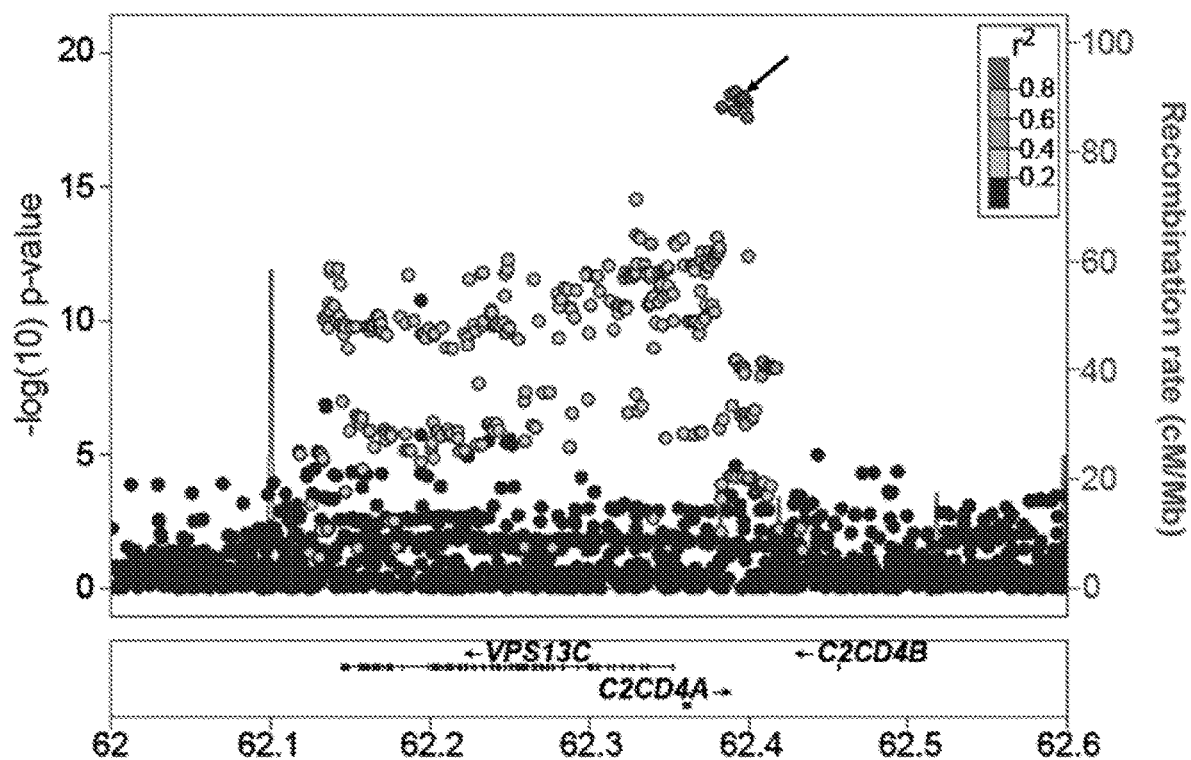
FIGS. 1A-1B. Fine-mapping identifies a single signal consisting of a cluster of sixteen highly linked variants associated with high proinsulin levels.

Genome-wide association studies (GWAS) in different populations have reported multiple T2D index SNPs in the C2 calcium-dependent domain-containing protein 4A/C2 calcium-dependent domain-containing protein 4B/Vacuolar protein sorting 13 homolog C locus (C2CD4A [MIM 610343], C2CD4B [MIM 610344], VPS13C [MIM 608879]) on 15q22.2, each associated with a T2D odds ratio (OR) of ~1.1 (range 1.06-1.14)5-8. Physiologic studies in non-diabetic European individuals suggest these variants do not affect insulin sensitivity, but rather contribute to T2D genetic risk through islet dysfunction. Reported T2D index SNP risk alleles were associated with increased fasting glucose[9-11] and proinsulin levels[11,12] and with decreased 2-hour glucose[11,13], HOMA-B9, glucose stimulated insulin secretion/release (GSIS/GSIR)[10], insulinogenic index[10,11], and BIGTT-based acute insulin release[10]. Conditional analysis of this locus in a Danish cohort indicated that rs7172432, or SNPs in high linkage disequilibrium (LD), exhibited stronger effects on fasting glucose and GSIR than several other SNPs reported[10]. Similarly, the rs7172432 risk "A" allele was associated with increased proinsulin levels in 8,224 METSIM study participants ($\beta$=0.042+0.005, p=7.4× 10-18)[12].

Genome-wide functional genomic and epigenomic analyses revealed that T2D GWAS SNPs are specifically and significantly enriched in islet enhancers[14-17], suggesting that these variants may perturb enhancer activity and transcriptional regulation in the islet to contribute genetic susceptibility to islet dysfunction and T2D[18]. In particular, associated variants are enriched in islet stretch/super enhancers (SEs), which are large (>3 kb), tissue-specific enhancer regions located in or nearby genes important for cell type-specific functions, such as genes encoding insulin (INS [MIM 176730]), Pancreas/Duodenum homeobox protein 1 (PDX1[MIM 600733]), and the regulatory and catalytic subunits of the ATP-binding cassette, subfamily C, member 8/Potassium channel, inwardly rectifying, subfamily J, member 11 (ABCC8 [MIM 600509], KCNJ11 [MIM 600937]) in islets[14]. As such, SE chromatin state signatures can be used to nominate likely important regulatory regions in or nearby genes of unknown function.

In this disclosure, genetic and functional genomic approaches were combined to investigate the T2D and T2D-related metabolic trait GWAS association on chromosome 15q22.2. Together, the data identify rs7163757 as the most likely causal variant in this locus and implicate C2CD4B [MIM 610344] and C2CD4A [MIM 610343] induction in T2D genetic risk and diabetogenic islet stress responses. Genetic fine-mapping identified a single association signal consisting of sixteen highly associated variants, which reside in an islet stretch enhancer state between C2CD4A and C2CD4B. rs7163757 is the only variant overlapping an islet open chromatin site. The rs7163757 T2D risk allele (C) exhibits two-fold higher enhancer activity than the non-risk allele (T), is differentially bound by beta cell nuclear factors, and is associated with increased C2CD4B, and likely C2CD4A, expression in human pancreatic islets.

Transgenic Cells and Animals

Some aspects of the present disclosure provide cells and/or animals (e.g., rodents, such as mice) comprising an inactivated C2 calcium-dependent domain containing 4A (C2cd4a) allele, an inactivated C2 calcium-dependent domain containing 4B (C2cd4b) allele, or an inactivated C2cd4a allele and an inactivated C2cd4b allele.

In some embodiments, the cells and/or animals comprise a modification in an allele of a C2cd4a gene, in an allele of a C2cd4b gene, or in an allele of a C2cd4a gene and in an allele of a C2cd4b gene. In some embodiments, the modification is in a C2cd4a gene (e.g., *Mus musculus* C2cd4a, Chromosome 9 NC_000075.6 (67830532..67832330, complement); or *Rattus norvegicus* C2cd4b, Chromosome 8 NC_005107.4 (73671516..73686344, complement)). In some embodiments, the modification is in a C2cd4b gene (e.g., *Mus musculus* C2cd4b, Chromosome 9 NC_000075.6 (67716225..67760933); or *Rattus norvegicus* C2cd4b, Chromosome 8 NC_005107.4 (73589848..73594516)). In some embodiments, the modification is in a C2cd4a gene and in a C2cd4b gene.

In some embodiments, the cells and/or animals comprise a modification in a genetic element that regulates expression of an allele of a C2cd4a gene, a modification in a genetic element that regulates expression of an allele of a C2cd4b gene, or a modification in a genetic element that regulates expression of an allele of a C2cd4a gene and a modification in a genetic element that regulates expression of an allele of a C2cd4b gene. In some embodiments, the genetic element is a promoter.

An inactivated gene is a gene that is not transcribed and/or does not encode a functional protein. A modification, with respect to a nucleic acid, is any manipulation of the nucleic acid, relative to the corresponding wild-type nucleic acid (e.g., the naturally-occurring nucleic acid). Non-limiting examples of nucleic acid modifications include deletions and/or insertions (e.g., "indels" and frameshift mutations) as well as substitutions (e.g., point mutations). Modifications also include chemical modifications, for example, chemical modifications of a nucleobase. Methods of nucleic acid modification, for example, those that result in gene inactivation, are known and include, without limitation, RNA interference, chemical modification, and gene editing (e.g., using recombinases or other programmable nuclease systems, e.g., CRISPR/Cas, TALENs, and/or ZFNs).

In some embodiments, the cells and/or animals comprise a deletion in at least one (e.g., one or more) allele of a C2cd4a gene, in at least one allele of a C2cd4b gene, or in a least one allele of a C2cd4a gene and in at least one allele of a C2cd4b gene. In some embodiments, the deletion is in a C2cd4a gene (e.g., *Mus musculus* C2cd4a, Chromosome 9 NC_000075.6 (67830532..67832330, complement); or *Rattus norvegicus* C2cd4b, Chromosome 8 NC_005107.4 (73671516..73686344, complement)). In some embodiments, the deletion is in a C2cd4b gene (e.g., *Mus musculus* C2cd4b, Chromosome 9 NC_000075.6 (67716225..67760933); or *Rattus norvegicus* C2cd4b, Chromosome 8 NC_005107.4 (73589848..73594516)). In some embodiments, the deletion is in a C2cd4a gene and a deletion in a C2cd4b gene.

A deletion refers to a mutation or loss of a genomic sequence. A gene deletion refers to a mutation or loss of a genomic sequence in or near a gene that prevents transcription of the gene and translation of a functional gene product. For example, a C2cd4a deletion may refer to a complete or partial loss of the C2cd4a gene sequence such that a functional C2cd4a gene product is not produced. Likewise, a C2cd4b deletion may refer to a complete or partial loss of the C2cd4b gene sequence such that a functional C2cd4b gene product is not produced.

An allele, as known in the art, is one of two or more alternative forms of a gene that arise by mutation and are found at the same place on a chromosome. In some embodiments, a cell comprises a modification (e.g., deletion) in one allele of a C2cd4a gene. In some embodiments, a cell comprises a modification (e.g., deletion) in both alleles of a C2cd4a gene. In some embodiments, a cell comprises a modification (e.g., deletion) in one allele of a C2cd4b gene. In some embodiments, a cell comprises a deletion in both alleles of a C2cd4b gene.

It is understood in the art that a cell comprising a deletion in one allele of a C2cd4a gene is referred to as having a C2cd4a$^{-/+}$ genotype. Likewise, a cell comprising a deletion in one allele of a C2cd4b gene has a C2cd4b$^{-/+}$ genotype. A cell comprising a deletion in both alleles of a C2cd4a gene has a C2cd4a$^{-/-}$ genotype, and a cell comprising a deletion in both alleles of a C2cd4b gene has a C2cd4b$^{-/-}$ genotype.

The cells provided herein are transgenic cells, meaning that the cells comprise an exogenous (foreign) nucleic acid. In some embodiments, the cells are eukaryotic cells, such as mammalian cells. Non-limiting examples of mammalian cells include human cells and rodent cells (e.g., mouse cells and/or rat cells). In some embodiments, the cells are islet beta cells, such as human islet beta cells and/or rodent islet beta cells (e.g., mouse islet beta cells or rat islet beta cells). In some embodiments, the cells are stem cells, e.g., embryonic stem cells. Other cell types (e.g., primate, equine, bovine, porcine, canine, and/or feline) are provided herein.

In some embodiments, a cell is a rodent cell. In some embodiments, a cell is mouse cell. For example, the mouse cell may be a New Zealand Obese (NZO) mouse cell (e.g., NZO/HILtJ cells, The Jackson Laboratory, Stock No: 002105). NZO inbred mice and strains derived from them develop severe obesity, and are thus useful for studying obesity and Type 2 diabetes.

In some embodiments, the transgenic cells as provided herein are present in a transgenic animal. Thus, the present disclosure provides transgenic animals comprising a transgenic cell. In some embodiments, a transgenic animal comprises a (at least one) C2cd4a$^{-/+}$ cell. In some embodiments, a transgenic animal comprises a C2cd4a$^{-/-}$ cell. In some embodiments, a transgenic animal comprises a C2cd4b$^{-/+}$ cell. In some embodiments, a transgenic animal comprises a C2cd4b$^{-/-}$ cell. In some embodiments, transgenic animal comprises a C2cd4a$^{-/+}$ cell and a C2cd4b$^{-/+}$. In some embodiments, transgenic animal comprises a C2cd4a$^{-/+}$ cell and a C2cd4b$^{-/-}$.

In some embodiments, transgenic animal comprises a C2cd4a$^{-/-}$ cell and a C2cd4b$^{-/+}$. In some embodiments, transgenic animal comprises a C2cd4a$^{-/-}$ cell and a C2cd4b$^{-/-}$. The transgenic animal may be a rodent, for example a mouse or a rat. Other transgenic animals (e.g., primate, equine, bovine, porcine, canine, and/or feline) are provided herein.

Transgenic Production Methods

Some aspects of the present disclosure provide methods for producing transgenic cells and/or animals. Methods of transgenic production are known in the art, any of which may be used herein. Examples of such methods include DNA microinjection, embryonic stem cell-mediated gene transfer, retrovirus-mediated gene transfer. See, e.g., Kumar T R et al. *Methods Mol Biol.* 2009; 590: 335-362, incorporated herein by reference. In some embodiment, Clustered Regularly Interspaced Short Palindromic Repeats (CRISPR)/Cas-mediated gene transfer approach is used. As one example, a transgenic mouse model can be generated with CRISPR/Cas9 by injecting Cas9 mRNA and either one or multiple single guide RNAs (sgRNA) directly into mouse embryos to generate precise genomic edits into specific loci. Mice that develop from these embryos are genotyped or sequenced to determine if they carry the desired mutation(s), and those that do are bred to confirm germline transmission. As another example, mouse strains with Cre recombinase-dependent Cas9 expression may be used. These mouse strains allow for in vivo CRISPR gene editing wherever a viral vector co-expressing Cre and the sgRNA is injected. The virally-expressed Cre turns on Cas9 expression, which in turn edits the targeted gene or genes. As yet another example, in vivo gene editing in mice can be accomplished by local or systemic injection of separate Cas9 and sgRNA expressing lenti- or adeno-associated viruses. CRISPR/Cas9-mediated gene editing occurs in cells that express both expression vectors.

Thus, provided herein are methods for producing a C2cd4a$^{-/-}$ rodent cell, the methods comprising introducing into the rodent cell a nucleic acid encoding a gRNA that targets a C2cd4a gene, wherein (a) the cell expresses a Cas nuclease, (b) the method further comprises activating expression of a Cas nuclease in the cell, or (c) the method further comprises introducing into the cell a nucleic acid encoding a Cas nuclease, culturing the cell, and producing the C2cd4a$^{-/-}$ rodent cell. The methods may further comprise introducing into the C2cd4a$^{-/-}$ rodent cell a nucleic acid encoding a gRNA that targets a C2cd4b gene, wherein (a) the C2cd4a$^{-/-}$ rodent cell expresses a Cas nuclease, (b) the method further comprises activating expression of a Cas nuclease in the C2cd4a$^{-/-}$ rodent cell, or (c) the method further comprises introducing into the C2cd4a$^{-/-}$ rodent cell a nucleic acid encoding a Cas nuclease, culturing C2cd4a$^{-/-}$ rodent cell, and producing a C2cd4a$^{-/-}$ IC2cd4b$^{-/-}$ rodent cell.

Other aspects of the present disclosure provide methods for producing a C2cd4b$^{-/-}$ rodent cell, the methods comprising introducing into the rodent cell a nucleic acid encoding a gRNA that targets a C2cd4b gene, wherein (a) the cell expresses a Cas nuclease, (b) the method further comprises activating expression of a Cas nuclease in the cell, or (c) the method further comprises introducing into the cell a nucleic acid encoding a Cas nuclease, culturing the cell, and producing the C2cd4b$^{-/-}$ rodent cell. In some embodiments, the methods further comprise introducing into the C2cd4b$^{-/-}$ rodent cell a nucleic acid encoding a gRNA that targets a C2cd4a gene, wherein (a) the C2cd4b$^{-/-}$ rodent cell comprises a Cas nuclease, (b) the method further comprises activating expression of a Cas nuclease in the C2cd4b$^{-/-}$ rodent cell, or (c) the method further comprises introducing into the C2cd4b$^{-/-}$ rodent cell a nucleic acid encoding a Cas nuclease, culturing the C2cd4b$^{-/-}$ rodent cell, and producing a C2cd4a$^{-/-}$C2cd4b$^{-/-}$ rodent cell.

Yet other aspects of the present disclosure provide methods for producing a C2cd4a$^{-/-}$/C2cd4b$^{-/-}$ rodent cell, the methods comprising introducing into the rodent cell a nucleic acid encoding a gRNA that targets a C2cd4a gene and a nucleic acid encoding a gRNA that targets a C2cd4b gene, wherein (a) the cell expresses a Cas nuclease, (b) the method further comprises activating expression of a Cas nuclease in the cell, or (c) the method further comprises introducing into the cell a nucleic acid encoding a Cas nuclease, culturing the cell, and producing the C2cd4a$^{-/-}$/C2cd4b$^{-/-}$ rodent cell.

As is known in the art, the CRISPR pathway includes two principal components: the Cas (e.g., Cas9) nuclease and a guide RNA (gRNA). The guide RNA is a two component system including crRNA and tracrRNA. The crRNA targets the double stranded DNA to be cut, and has a short region of homology allowing it to bind the tracrRNA. The tracrRNA provides a stem loop structure which associates with Cas nuclease. The crRNA:tracrRNA duplex is referred to as the gRNA. The Cas9 nuclease and gRNA form a Cas9 ribonucleoprotein (RNP), which can bind and cut a specific DNA target in a whole genome context. In order to be cleaved by the RNP, a target includes two specific sequences. First, the gRNA typically includes approximately 20 bases of RNA-to-DNA homology, which is referred to as the protospacer. Second, the Cas nuclease includes a short protospacer adjacent motif (PAM) in order to bind to the target DNA. If the linking tracrRNA is present, and enough homology exists between the gRNA and the genomic target, the RNP cleaves both strands of the target DNA, creating a double-stranded break (DSB) at this precise location in the genome.

In some embodiments, a Cas nuclease is a Cas9 nuclease. It should be understood that in any of the embodiments described herein, Cas nuclease may substituted with Cpf1 nuclease or other CRISPR-associated nuclease. Cas nuclease and Cpf1 nuclease variants are also encompassed herein.

Methods of identifying gRNAs for use in modifying or deleting a nucleic acid sequence (e.g., of an allele) are known. For example, there are various commercial companies that offer computation programs to guide the selection of gRNA targets. See, e.g., Addgene's Validated gRNA Sequence Datatable. The general principles guiding gRNA selection include: identifying the region of the genome for targeting (the intended target site), identify protospacer sequences near the intended target site, and select protospacer sequences that minimize off-target effects. Examples of gRNA sequences used to target C2cd4a and C2cd4b are as follows:

```
                                          (SEQ ID NO: 1)
AGCCACTGGTATCGTCCCTT (6358_C2cd4a_sgRNA1), (SEQ ID NO: 2)
TTCCAAAGGGACGATACCAG (6359_C2cd4a_sgRNA2), (SEQ ID NO: 3)
CTGCTTTGACCGGCTCCCGG, (6360_C2cd4a_sgRNA3),

CTGCTGCTTTGACCGGCTCC (6361_C2cd4a_sgRNA4), (SEQ ID NO: 4)
CTGGATATGTTAAACGTAGG (6362_C2cd4b_sgRNA1), (SEQ ID NO: 5)
CTTGGCATGTCCGTTTAGGA (6363_C2cd4b_sgRNA2), (SEQ ID NO: 6)
CCTGGCCGTGCGCATCAAGG (6364_C2cd4b_sgRNA3),
and (SEQ ID NO: 7)
CCTTGATGCGCACGGCCAGG (6365_C2cd4b_sgRNA4)).
```

Methods of introducing nucleic acids (e.g., DNA and/or RNA) and proteins into cells are known, any of which may be used herein. In some embodiments, the step of introducing a nucleic acid (e.g., a gRNA or a nucleic acid encoding a gRNA, or a nucleic acid encoding Cas nuclease) into a cell is performed by electroporation, viral transduction, chemical transfection, or other non-chemical transfection methods.

Transgenic cells produced herein may be used to produce transgenic animals. In some embodiments, the methods further comprise introducing a transgenic cell such as a transgenic embryonic stem cell into an inner cell mass of a blastocyst, which is then implanted in the uterus of a female animal. In some embodiments, the methods further comprise introducing a transgenic embryonic murine stem cell into an inner cell mass of a murine blastocyst, which is then implanted in the uterus of a female mouse (female mice), such as a NZO/HILtJ mouse.

Heterozygous offspring of a female mouse may be mated to produce homozygous mice having, for example, a C2cd4a$^{-/+}$, C2cd4b$^{-/+}$, or C2cd4a$^{-/+}$/C2cd4b$^{-/+}$ genotype.

Prevention and/or Treatment of Type II Diabetes

Some aspects of the present disclosure provide methods for preventing and/or treating diabetes (e.g., Type II diabetes). Genetic fine-mapping of genome-wide association study (GWAS) sequences described herein identified a single association signal including sixteen highly-associated single nucleotide polymorphisms (SNPs) (T2D-associated SNPs): rs4502156 allele (T), rs1881415 allele (T), rs67818839 allele (A), rs7163757 allele (C), rs8037894 allele (G), rs8038040 allele (G), rs6494307 allele (C), rs7161785 allele (G), rs7167878 allele (C), rs7167932 allele (C), rs7172432 allele (A), rs7173964 allele (G), rs4775466 allele (C), rs4775467 allele (G), rs10083587 allele (C), and rs11856307 (A), which are associated with high levels of fasting proinsulin and with T2D. Thus, in some embodiments, the methods that comprise assaying a genomic sample for at least one of these sixteen highly-associated SNPs. In some embodiments, the methods comprise assaying a genomic sample for rs4502156 allele (T). In some embodiments, the methods comprise assaying a genomic sample for rs1881415 allele (T). In some embodiments, the methods comprise assaying a genomic sample for rs67818839 allele (A). In some embodiments, the methods comprise assaying a genomic sample for rs7162757 allele (C). In some embodiments, the methods comprise assaying a genomic sample for rs8037894 allele (G). In some embodiments, the methods comprise assaying a genomic sample for rs8038040 allele (G). In some embodiments, the methods comprise assaying a genomic sample for rs6494307 allele (C). In some embodiments, the methods comprise assaying a genomic sample for rs7161785 allele (G). In some embodiments, the methods comprise assaying a genomic sample for rs7167878 allele (C). In some embodiments, the methods comprise assaying a genomic sample for rs7167932 allele (C). In some embodiments, the methods comprise assaying a genomic sample for rs7172432 allele (A). In some embodiments, the methods comprise assaying a genomic sample for rs7173964 allele (G). In some embodiments, the methods comprise assaying a genomic sample for rs4775466 allele (C). In some embodiments, the methods comprise assaying a genomic sample for rs4775467 allele (G). In some embodiments, the methods comprise assaying a genomic sample for rs10083587 allele (C). In some embodiments, the methods comprise assaying a genomic sample for rs11856307 allele (A).

A genomic (DNA) sample may be assayed for a particular SNP by simply sequencing the genomic sample. For example, DNA isolated from a biological sample obtained from a subject may be sequenced using any one of the basic or high-throughput sequencing methods known in the art (see, e.g., Heather J M et al. Genomics, 2016; 107(1): 1-8, incorporated herein by reference). Other methods for assaying a SNP include single strand conformation polymorphism (SSCP), cleavage fragment length polymorphism analysis (CFLPA), and denaturing high performance liquid chromatography (DHPLC).

In some embodiments, a genomic sample is obtained from a biological sample from a subject. For example, a genomic sample may be obtained from blood, saliva, or urine. Other biological samples may be used.

In other embodiments, the methods comprise assaying a genomic sample obtained from a subject (e.g., a human subject) for an intergenic variant located in a region between a C2 calcium-dependent domain containing 4A gene (C2CD4A) and a C2 calcium-dependent domain containing 4B gene (C2CD4B). An intergenic variant may be any change in nucleotide sequence in a region located between two genes. In some embodiments, the intergenic variant is a SNP. In other embodiments, the intergenic variant is a deletion (of one or more nucleotides). In yet other embodiments, the intergenic variant is an insertion (of one or more nucleotides). Intergenic variants also include nucleotides modifications. In some embodiments, the intergenic variant is a SNP selected from rs4502156 allele (T), rs1881415 allele (T), rs67818839 allele (A), rs7162757 allele (C), rs8037894 allele (G), rs8038040 allele (G), rs6494307 allele (C), rs7161785 allele (G), rs7167878 allele (C), rs7167932 allele (C), rs7172432 allele (A), rs7173964 allele (G), rs4775466 allele (C), rs4775467 allele (G), rs10083587 allele (C), and rs11856307 (A). In some embodiments, the intergenic variant is SNP rs7163757 allele (C).

In some embodiments, the methods further comprise measuring a level of proinsulin in a biological sample obtained from the subject. Insulin resistance and deterioration of beta-cell secretion are main features in the development of type 2 diabetes, which is reflected in increasing serum intact proinsulin levels. Proinsulin is synthesized by the beta cell of the pancreas as a precursor molecule for insulin. Physiologically, virtually all proinsulin molecules are intracellularly cleaved by carboxypeptides into insulin and C-peptide. Normal (non-diabetic) subjects typically have proinsulin concentrations below the upper limit of the normal fasting reference range (~22 pmol/L) when hypoglycemic (blood glucose <60 mg/dL). Proinsulin levels may be measured, for example, using a blood test.

Thus, when the intergenic variant (e.g., is SNP rs7163757 allele (C)) is present in a genomic sample and/or the level of proinsulin in the biological sample is greater than 22 pmol/L, (e.g., greater than 25, 30, 35, 40, 45, or 50 pmol/L) the methods may further comprise administering to the subject a therapy to prevent or treat diabetes in the subject. In some embodiments, the therapy is for insulin resistance. Therapies for insulin resistance to prevent or treat diabetes include pharmacologic therapies that reduce insulin resistance (insulin-sensitizing and antihyperglycemic effects) such as metformin, thiazolidinediones, and concentration insulin (U-100 insulin or U-500 insulin) and surgical treatment of underlying causes, such as bariatric surgery (e.g., gastric banding, sleeve gastrectomy, and gastric bypass) in selected morbidly obese subjects.

In some embodiments, the therapy for diabetes comprises administering to the subject an agent that reduces expression and/or activity of C2CD4A protein and/or C2CD4B protein. In some embodiments, the therapy for diabetes comprises administering to the subject an agent that reduces expression of C2CD4A protein. In some embodiments, the therapy for diabetes comprises administering to the subject an agent that reduces activity of C2CD4A protein. In some embodiments, the therapy for diabetes comprises administering to the subject an agent that reduces expression of C2CD4B protein. In some embodiments, the therapy for diabetes comprises administering to the subject an agent that reduces activity of C2CD4B protein. Examples of these agents include RNA interference molecules, such as siRNA and shRNA molecules, small molecule drugs, and other agents that reduce expression and/or activity of C2CD4A protein and/or C2CD4B protein.

In some embodiments, the therapy for insulin resistance comprises administering to the subject an agent that reduces expression and/or activity of C2CD4A protein and/or C2CD4B protein. In some embodiments, the therapy for insulin resistance comprises administering to the subject an agent that reduces expression of C2CD4A protein. In some embodiments, the therapy for insulin resistance comprises administering to the subject an agent that reduces activity of C2CD4A protein. In some embodiments, the therapy for insulin resistance comprises administering to the subject an agent that reduces expression of C2CD4B protein. In some embodiments, the therapy for insulin resistance comprises administering to the subject an agent that reduces activity of C2CD4B protein. Examples of these agents include RNA interference molecules, such as siRNA and shRNA molecules, small molecule drugs, and other agents that reduce expression and/or activity of C2CD4A protein and/or C2CD4B protein.

In some embodiments, the therapy for diabetes comprises administering to the subject an agent that reduces calcineurin (Cn)/NFAT pathway activity. In some embodiments, the therapy for insulin resistance comprises administering to the subject an agent that reduces calcineurin (Cn)/NFAT pathway activity. The NFAT family transcription factors are highly expressed in human and rodent islet cells and regulate the expression of several T2D-associated genes. Calcineurin mediates the localization of NFAT proteins from the cytosol to the nucleus where they can regulate gene expression. Examples of agents that reduce (inhibit) Cn/NFAT pathway activity include the microbial drugs Cyclosporin A (CsA) and FK506. Other Cn/NFAT pathway inhibitors may be used.

Diagnosis of Type II Diabetes

Some aspects of the present disclosure provide methods for diagnosing diabetes (e.g., Type II diabetes (T2D)) in a subject. In some embodiments, diagnostic methods comprise assaying a genomic sample obtained from a subject (e.g., a human subject) for at least one of the following sixteen highly-associated SNPs (T2D-associated SNPs): rs4502156 allele (T), rs1881415 allele (T), rs67818839 allele (A), rs7163757 allele (C), rs8037894 allele (G), rs8038040 allele (G), rs6494307 allele (C), rs7161785 allele (G), rs7167878 allele (C), rs7167932 allele (C), rs7172432 allele (A), rs7173964 allele (G), rs4775466 allele (C), rs4775467 allele (G), rs10083587 allele (C), and/or rs11856307 (A). In some embodiments, the methods comprise assaying a genomic sample for rs4502156 allele (T). In some embodiments, the methods comprise assaying a genomic sample for rs1881415 allele (T). In some embodiments, the methods comprise assaying a genomic sample for rs67818839 allele (A). In some embodiments, the methods comprise assaying a genomic sample for rs7162757 allele (C). In some embodiments, the methods comprise assaying a genomic sample for rs8037894 allele (G). In some embodiments, the methods comprise assaying a genomic sample for rs8038040 allele (G). In some embodiments, the methods comprise assaying a genomic sample for rs6494307 allele (C). In some embodiments, the methods comprise assaying a genomic sample for rs7161785 allele (G). In some embodiments, the methods comprise assaying a genomic sample for rs7167878 allele (C). In some embodiments, the methods comprise assaying a genomic sample for rs7167932 allele (C). In some embodiments, the methods comprise assaying a genomic sample for rs7172432 allele (A). In some embodiments, the methods comprise assaying a genomic sample for rs7173964 allele (G). In some embodiments, the methods comprise assaying a genomic sample for rs4775466 allele (C). In some embodiments, the methods comprise assaying a genomic sample for rs4775467 allele (G). In some embodiments, the methods comprise assaying a genomic sample for rs10083587 allele (C). In some embodiments, the methods comprise assaying a genomic sample for rs11856307 allele (A). In some embodiments, when the SNP is present in the genomic sample, the methods further comprise diagnosing the subject as having diabetes (e.g., T2D) or as at risk of diabetes (e.g., T2D).

Methods for assaying a SNP are described elsewhere herein.

In other embodiments, diagnostic methods comprise assaying a genomic sample obtained from a subject (e.g., a human subject) for an intergenic variant located in a region between a C2 calcium-dependent domain containing 4A gene (C2CD4A) and a C2 calcium-dependent domain containing 4B gene (C2CD4B). In some embodiments, the intergenic variant is a SNP. In other embodiments, the intergenic variant is a deletion (of one or more nucleotides). In yet other embodiments, the intergenic variant is an insertion (of one or more nucleotides). Intergenic variants also include nucleotides modifications. In some embodiments, the intergenic variant is a SNP selected from rs4502156 allele (T), rs1881415 allele (T), rs67818839 allele (A), rs7162757 allele (C), rs8037894 allele (G), rs8038040 allele (G), rs6494307 allele (C), rs7161785 allele (G), rs7167878 allele (C), rs7167932 allele (C), rs7172432 allele (A), rs7173964 allele (G), rs4775466 allele (C), rs4775467 allele (G), rs10083587 allele (C), and rs11856307 (A). In some embodiments, the intergenic variant is SNP rs7163757 allele (C). In some embodiments, when the intergenic variant (e.g., is SNP rs7163757 allele (C)) is present in a genomic sample, the methods further comprise diagnosing the subject as having diabetes (e.g., T2D) or as at risk of diabetes (e.g., T2D).

In some embodiments, the diagnostic methods further comprise measuring a level of proinsulin in a biological sample obtained from the subject. In some embodiments, when the intergenic variant (e.g., is SNP rs7163757 allele (C)) is present in a genomic sample and/or the level of proinsulin in the biological sample is greater than 22 pmol/ L, (e.g., greater than 25, 30, 35, 40, 45, or 50 pmol/L) the methods may comprise diagnosing the subject as having diabetes (e.g., T2D) or at risk of diabetes (e.g., T2D).

sis identified a cluster of sixteen strongly associated variants ($p<1\times10^{-17}$; FIG. 1A). These included the GWAS index SNP rs7172432 (arrow) and fifteen variants in high linkage disequilibrium ($r^2>0.8$) as putative causal variants (see also Table 1). Of note, the set of 16 most strongly associated ($p<1\times10^{-17}$) variants corresponded to the 99% "credible set" obtained by carrying out a more formal Bayesian fine-mapping analysis based on approximate Bayes' factors[48,49]. This 99% credible set contains, with >99% probability, the variant causal for the association signal, assuming this variant was included in the analysis. Finally, these variants also exhibited the strongest association p-values for this locus in the latest T2D meta-analysis[50].

Figure 1B:
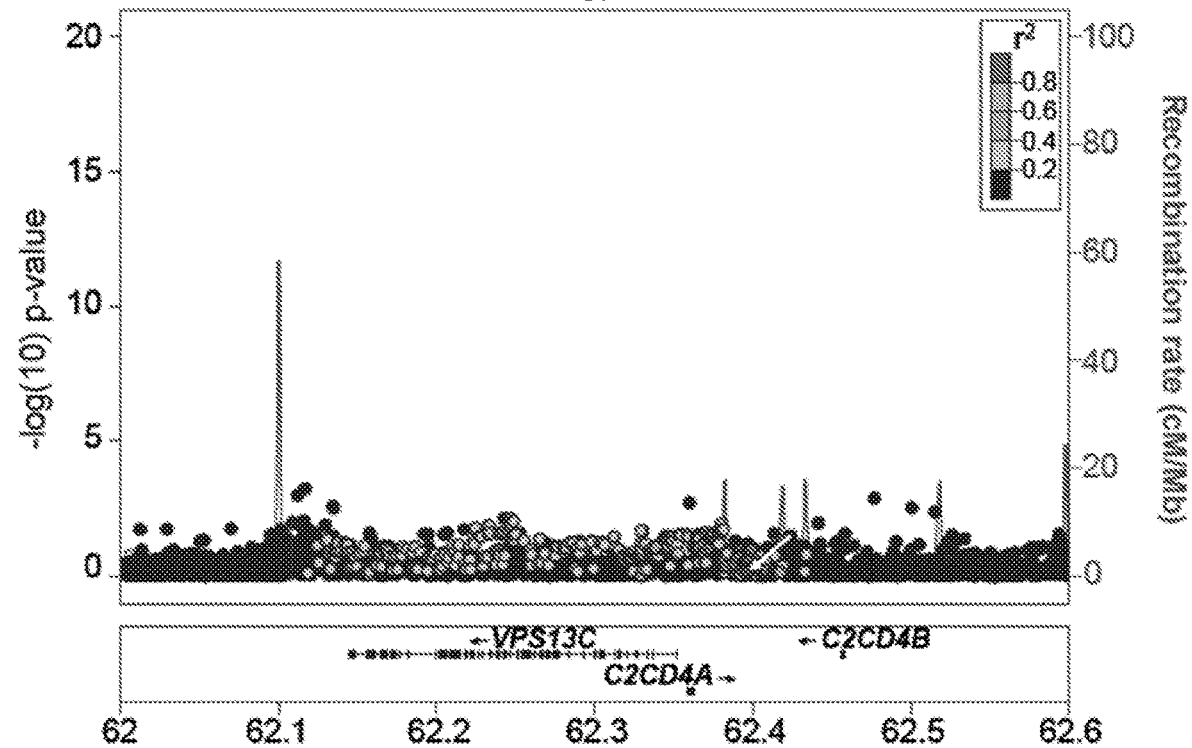

All sixteen variants are located between two recombination hotspots in the intergenic region between C2CD4A and C2CD4B. Conditional analysis using rs7172432 as a covariate attenuated the strength of the proinsulin association in this locus (FIG. 1B, all SNPs, $p>10^{-5}$). Taken together, fine mapping and conditional analysis support a single proinsulin association signal in this locus and implicate sixteen highly-linked intergenic variants ($r^2>0.8$) as the putative causal/ functional variants underlying both increased proinsulin levels and T2D risk in this locus.

TABLE 1

Proinsulin-associated C2CD4A/B intergenic variants.

| SNP ID | Chr | Pos | p-value | Effect | Effect Allele | Other Allele | MAF |
|---|---|---|---|---|---|---|---|
| rs4502156 | chr15 | 62383155 | 1.08E−18 | −0.136 | C | T | 0.4355 |
| rs1881415 | chr15 | 62388530 | 3.69E−19 | −0.139 | C | T | 0.4369 |
| rs67818839 | chr15 | 62391184 | 1.38E−18 | −0.136 | AT | A | 0.44608 |
| rs7163757 | chr15 | 62391608 | 2.98E−19 | −0.138 | T | C | 0.44653 |
| rs8037894 | chr15 | 62394264 | 6.13E−19 | −0.137 | C | G | 0.45058 |
| rs8038040 | chr15 | 62394339 | 6.01E−19 | −0.137 | A | G | 0.45067 |
| rs6494307 | chr15 | 62394690 | 6.31E−19 | −0.137 | G | C | 0.45061 |
| rs7161785 | chr15 | 62395224 | 6.21E−19 | −0.137 | C | G | 0.45058 |
| rs7167878 | chr15 | 62396189 | 6.24E−19 | −0.137 | A | C | 0.45072 |
| rs7167932 | chr15 | 62396278 | 6.30E−19 | −0.137 | T | C | 0.45059 |
| rs7172432 | chr15 | 62396389 | 4.88E−19 | −0.138 | G | A | 0.44769 |
| rs7173964 | chr15 | 62396942 | 6.86E−19 | −0.137 | A | G | 0.45067 |
| rs4775466 | chr15 | 62397118 | 6.65E−19 | −0.137 | T | C | 0.4507 |
| rs4775467 | chr15 | 62397398 | 6.64E−19 | −0.137 | A | G | 0.45068 |
| rs10083587 | chr15 | 62398533 | 7.39E−19 | −0.137 | T | C | 0.45168 |
| rs11856307 | chr15 | 62399093 | 2.54E−19 | −0.135 | C | A | 0.45279 |

The following abbreviations are used:
SNP ID: single nucleotide polymorphism identification data,
Chr: chromosome,
Pos: position,
MAF: minor allele frequency and
ATAC: assay for transposase accessible chromatin.

EXAMPLES

Example 1. Fine-Mapping Identifies Sixteen Highly Linked Intergenic Variants Associated with Fasting Proinsulin and T2D on 15q22.2 rs7172432 has been the most reported C2CD4A/B/ VPS13C locus index SNP associated with T2D and quantitative traits related to islet dysfunction in multiple populations[5,6,8,10,12]. To identify a set of candidate causal variants for functional follow-up in this locus, a genetic fine-mapping analysis of the fasting proinsulin association signal in the locus in 8,635 non-diabetic Finnish individuals from the METSIM study was conducted[11,12,19]. Fine-mapping analy-

Example 2. Putative Causal Variants Reside in an Evolutionarily-Conserved Islet Stretch Enhancer (SE)

Figure 2A:
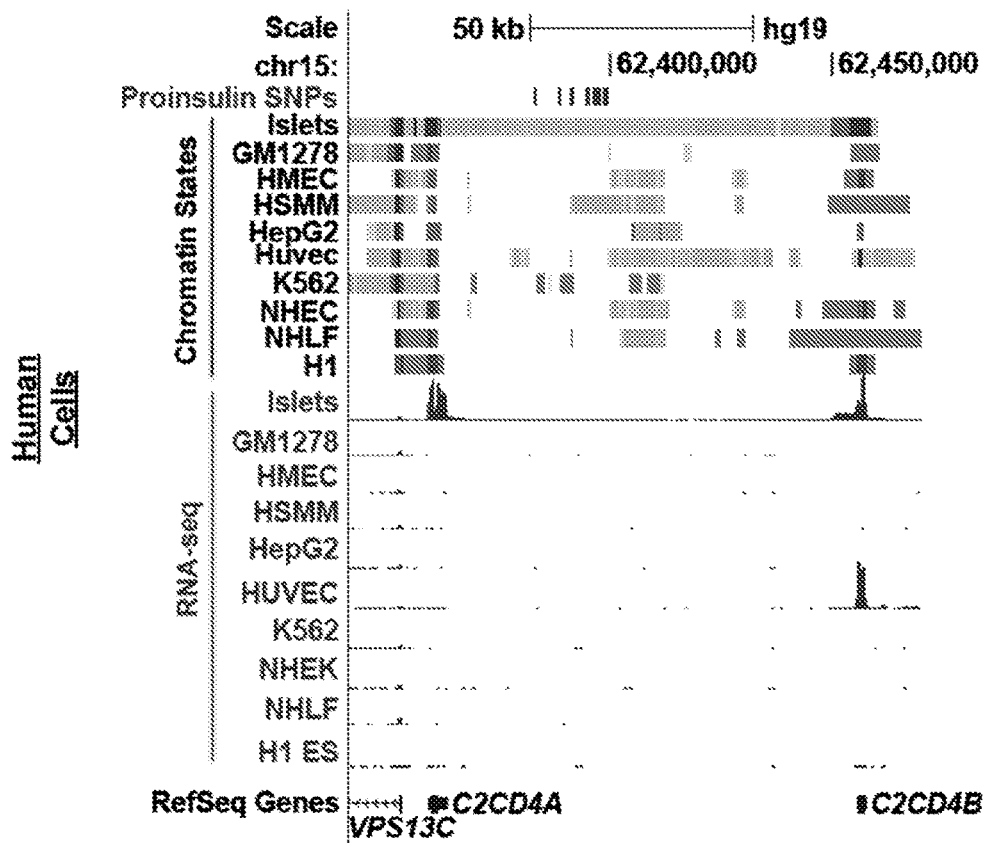
FIGS. 2A-2C. Fine-mapped variants reside in an evolutionarily conserved islet stretch enhancer. UCSC Genome Browser views of chromatin states (upper panels) and RNA-seq (lower panels) in (FIG. 2A) human pancreatic islets and nine ENCODE cell types (GM12878, lymphoblastoid cells; HMEC, human mammary epithelial cells; HSMM, human smooth muscle myoblasts; HepG2, hepatocellular carcinoma cells; HUVEC, human umbilical vein endothelial cells; K562, erythroleukemia cells; NHEK, normal human epidermal keratinocytes; NHLF, normal human lung fibroblasts; H1 ES, embryonic stem cells)
Figure 2B:
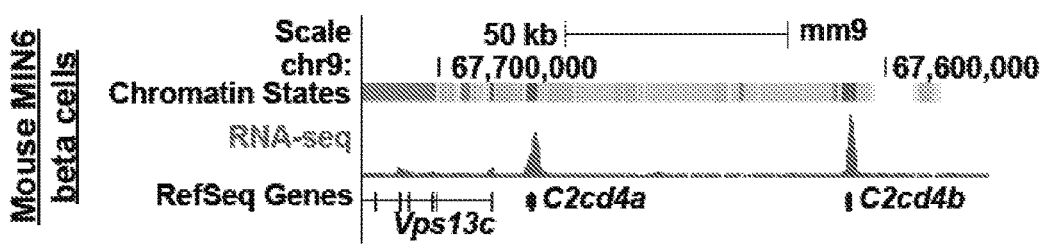
Figure 2C:
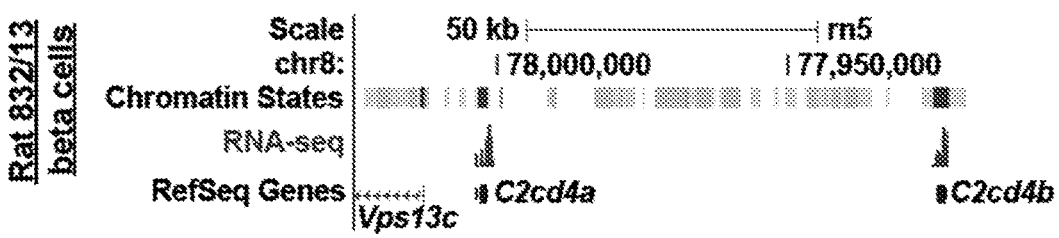

Because all sixteen variants identified by fine-mapping were intergenic (FIG. 1, Table 1), it was hypothesized that one or more of them may reside in islet regulatory elements. Analysis of ChromHMM-defined chromatin states[14,34] in this region revealed that these variants overlap islet-specific SEs between the C2CD4A and C2CD4B genes (FIG. 2A). VPS13C was modestly expressed in multiple tissues (RPKM>1), while C2CD4A and C2CD4B expression was restricted to human pancreatic islets and a few additional cell types/tissues (FIG. 2A, RNA-seq tracks). Interestingly, ChIP-seq and chromatin state analyses of the orthologous region in mouse MIN6 (FIG. 2B) and rat INS-1(832/13) (FIG. 2C) beta cell lines detected SE signatures in both species. Furthermore, both C2cd4a and C2cd4b were expressed in MIN6 and INS-1(832/13) beta cells (RNA-seq tracks; FIGS. 2B, 2C). The functional preservation of the chromatin structure and transcriptional output in this locus suggest that it plays an evolutionarily important role in islet/beta cell function. Collectively, these results indicate that the putative causal variants overlap an evolutionarily-conserved islet SE and support the hypothesis that one or more of them may contribute to beta cell dysfunction by altering SE activity and target gene expression.

Example 3. Rs7163757 Resides in an Islet SE Constituent Open Chromatin Site

Figure 3A:
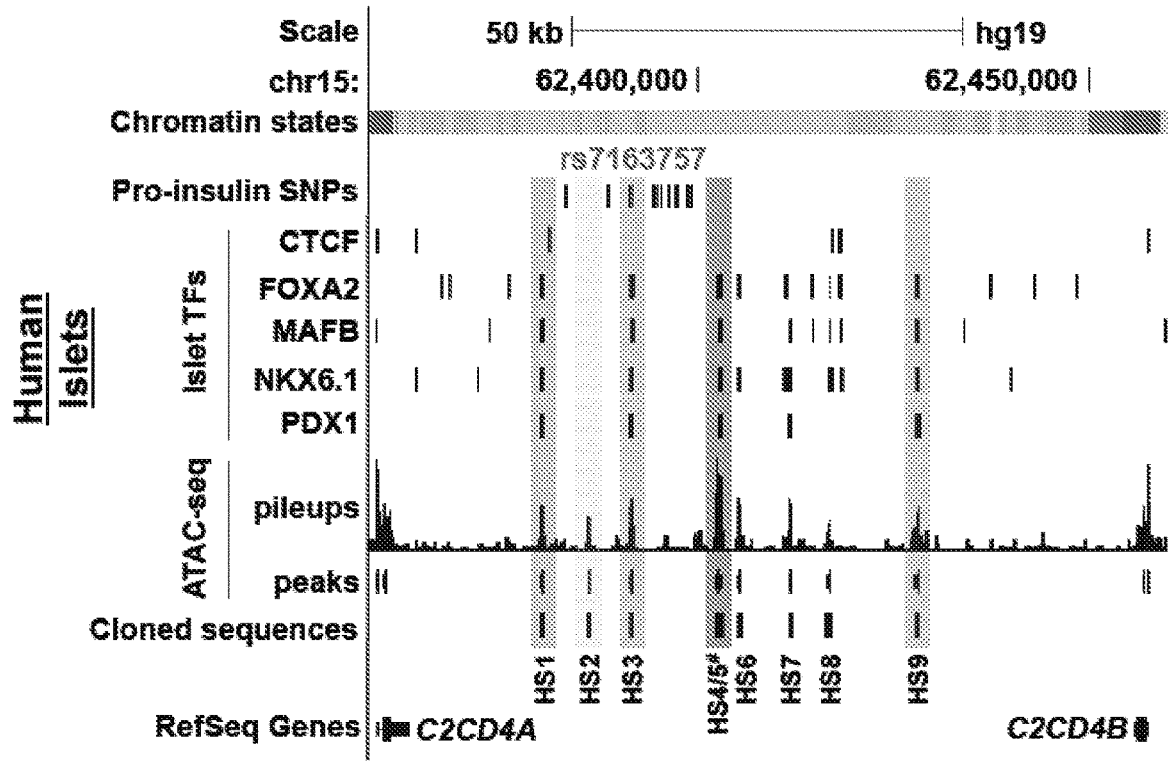
FIGS. 3A-3C. rs7163757 resides in an evolutionarily-conserved islet (beta cell) open chromatin site. UCSC Genome Browser views of C2CD4A/B/VPS13C stretch enhancer (SE) constituent open chromatin sites determined by ATAC-seq in (FIG. 3A) human islets, (FIG. 3B) mouse MIN6, and (C) rat INS-1(832/13) beta cells. Open chromatin sites were detected in this region and are indicated by the ATAC-seq pileups and the peaks (MACS peak calls) in each species between C2CD4A and C2CD4B (RefSeq Genes). Chromatin states are indicated as in FIGS. 2A-2C. One of the sixteen proinsulin variants (rs7163757) overlaps an open chromatin site (HS3) bound by multiple islet transcription factors (TFs) NKX6.1, FOXA2, PDX1 and MAFB but not CTCF according to published islet ChIP-seq data[16]. Black tick marks in panel A indicate the locations of the additional fifteen variants associated with higher proinsulin (Pro-insulin SNPs). Human genomic DNA sequences overlapping open chromatin sites (HS1-9) were selected and cloned as indicated. Human open chromatin DNA sequences that map to mouse and/or rat open chromatin sites are indicated. HS3 DNA sequence maps to open chromatin sites in both MIN6 and INS-1(832/13). HS1 and HS5 map only to MIN6 open chromatin sites; HS2, HS4 and HS9 map only to INS-1(832/13) open chromatin sites. HS4/5# stands for the individually cloned sites HS4, HS5 and the combined site HS4+5. Genome browser coordinates correspond to hg19, mm9, and rn5, genome builds respectively.

SEs can encompass multiple, discrete open chromatin sites[14,15,51]. Chromatin accessibility in human islets was profiled using the assay for transposase accessible chromatin (ATAC-seq)[29] to determine the constituent open chromatin sites within the C2CD4A/B/VPS13C islet SE and to identify any overlaps with the putative causal/functional variant(s) among the sixteen variants in this locus. As shown in FIG. 3A, nine intergenic open chromatin sites (HS 1-9) were detected between C2CD4A and C2CD4B in human islets (sequence pileups and MACS2 peak calls). All sites overlapped islet active enhancer states (FIG. 3A), some of which also exhibited evidence of chromatin accessibility or enhancer chromatin states in other tissues. By analyzing reported genome-wide binding sites for islet transcription factors (TFs) FOXA2, MAFB, NKX6.1 and PDX1[16], it was found that about half (4/9) of these sites were bound by all four islet TFs (FIG. 3A). Only one of the sixteen fine-mapped variants, rs7163757, overlapped an islet open chromatin site (FIG. 3A, HS3), suggesting this is the functional variant among the multiple linked variants.

Figure 3B:
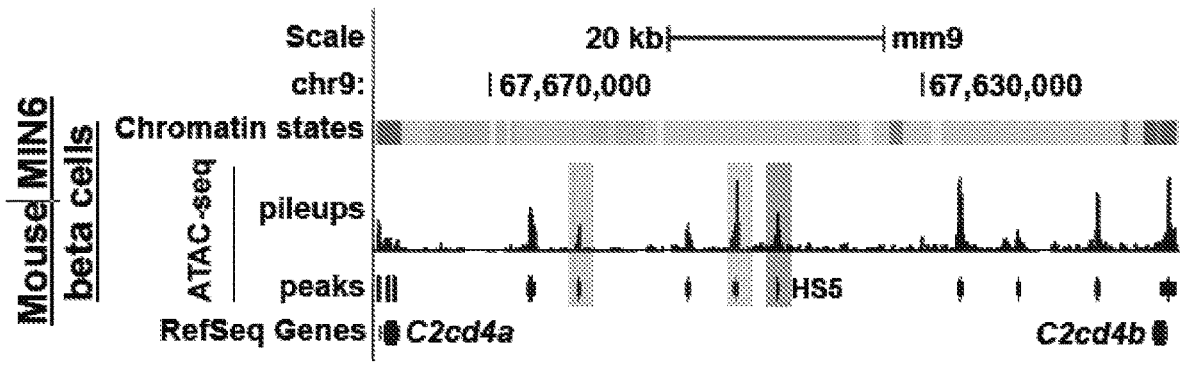
Figure 3C:
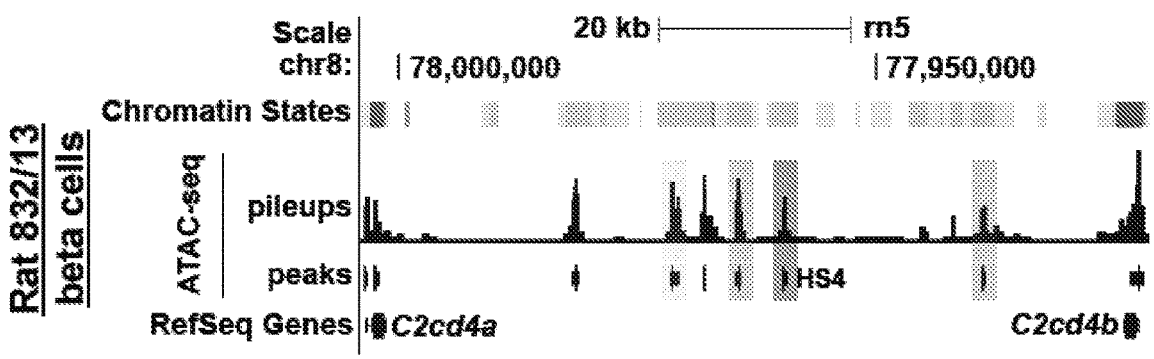

Sequences overlapping seven of the islet SE constituent sites exhibited evidence of sequence constraint through the vertebrate lineage. To determine which of the islet SE constituent sites in this locus were functionally preserved in rodents, ATAC-seq profiling was used and identified eight open chromatin sites in mouse MIN6 cell lines (FIG. 3B) and six sites in rat INS-1(832/13) (FIG. 3C) beta cell lines. Liftover (genome.ucsc.edu/cgi-bin/hgLiftOver) and bnmapper[52] comparative sequence analysis tools were used to identify mouse and rat sequences orthologous to the human islet HS1-9 open chromatin sites and to determine which of them overlapped beta cell SE constituent sites in MIN6 (FIG. 3B) and INS-1(832/13) (FIG. 3C) beta cell lines. Two adjacent open chromatin site sequences, HS 4 and 5 (FIG. 3) mapped to an open chromatin site in INS-1(832/13) (HS4) or in MIN6 (HS5). One open chromatin site sequence, HS1, mapped only to an open chromatin site in MIN6 (FIGS. 3A, 3B). HS2 and HS9 mapped only to open chromatin sites in INS-1(832/13) (FIGS. 3A, 3C). Only HS3 sequence mapped to open chromatin sites in the beta cell lines from both species (FIG. 3, dark gray shading). Thus, these comparative analyses highlight HS3, which contains the proinsulin-associated variant rs7163757, as the only sequence preserved as a functional regulatory site in both mouse and rat beta cells.

Example 4. Rs7163757 Risk Allele (C) Exhibits Higher Enhancer Activity than the Non-Risk Allele (T)

Figure 4A:
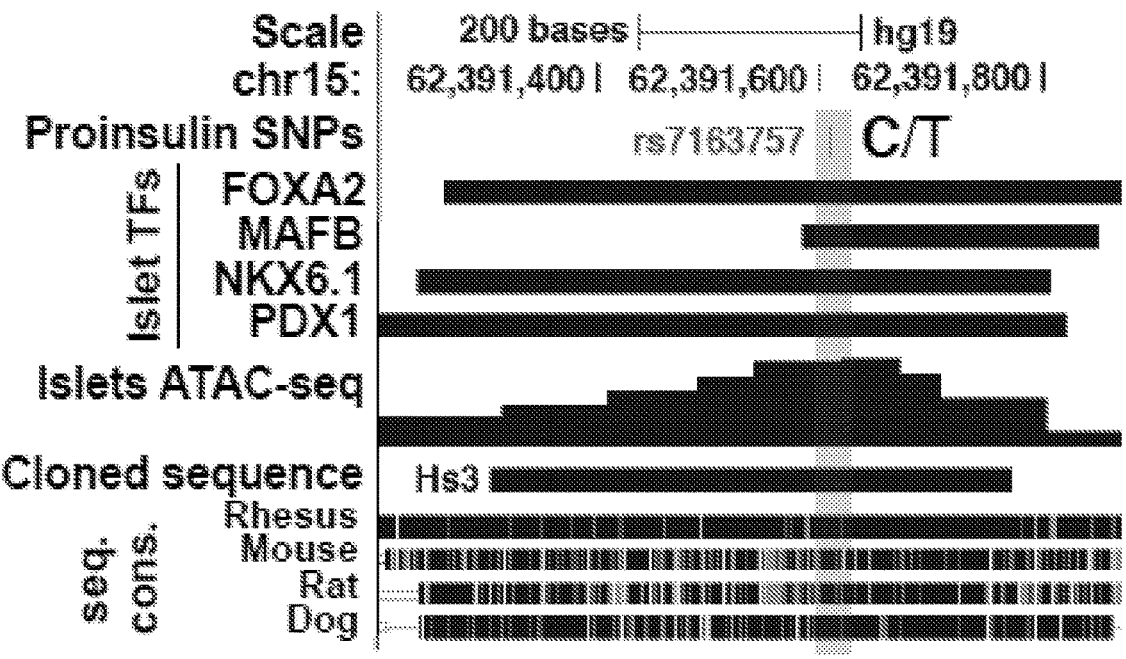
FIGS. 4A-4B. rs7163757 risk allele (C) exhibits two-fold higher enhancer activity than the non-risk allele (T).
Figure 4B:
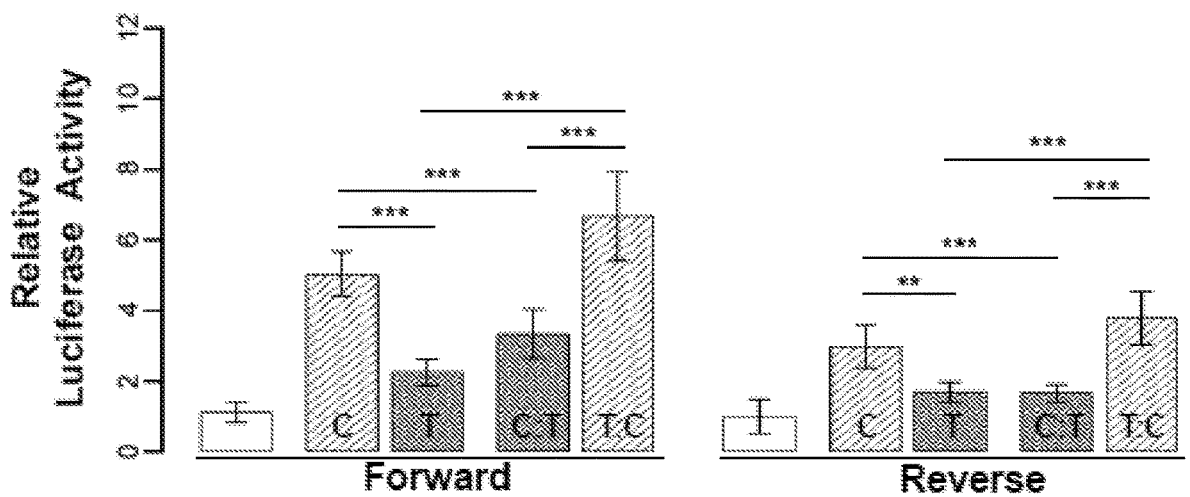

Based on chromatin profiling and cross-species analyses, it was hypothesized that rs7163757 alleles alter HS3 regulatory element activity. To test this, the HS3 sequence (FIG. 4A) from human islet gDNA containing either the risk (C) or non-risk (T) alleles were cloned and measured each sequence's enhancer activity in MIN6 and INS-1(832/13) beta cells using luciferase reporter assays. Both HS3 alleles exhibited enhancer activity compared to empty vector (FIG. 4B). However, the rs7163757 risk allele (C) conferred two-fold increased enhancer activity compared to the non-risk allele (T) (FIG. 4B). An additional sequence variant (rs28578604) was identified in the HS3 amplicon. To rule out a role for rs28578604 in the observed HS3 allelic enhancer activity differences, site-directed mutagenesis was used to experimentally convert the rs7163757 genotypes (T:C and C:T, respectively) while leaving rs28578604 unchanged. The mutagenized rs7163757 T:C and C:T constructs exhibited comparable enhancer activity to the original risk and non-risk haplotypes, respectively (FIG. 4B).

The additional C2CD4A/B SE constituent sites (FIG. 3A, HS1-9) were tested, and it was found that HS1, HS7, and HS9 sequences also enhance luciferase reporter activity in both orientations. HS1, HS2, and HS6 also contained sequence variants. However, significant haplotype-specific differences in enhancer activity of these islet SE constituent sequences were not detected. Thus, multiple islet SE constituent sites exhibit enhancer activity. However, only HS3, which contains the putative causal variant rs7163757, exhibits allelic differences in activity. Allelic analyses of ATAC-seq data from rs7163757 C/T heterozygous islet samples[34] did not reveal consistent or significant over- or underrepresentation of the risk allele in accessible/open chromatin, and it was found both alleles present in published islet active enhancer histone modifications and TF ChIP-seq datasets (not shown)[16,34]. Together, these data suggest that the rs7163757 alleles do not create or destroy the transcriptional enhancer. Thus, the rs7163757 risk allele (C) potentiates HS3 enhancer activity, potentially by creating a binding site for a stimulus- or stress-responsive TF.

Figure 5A:
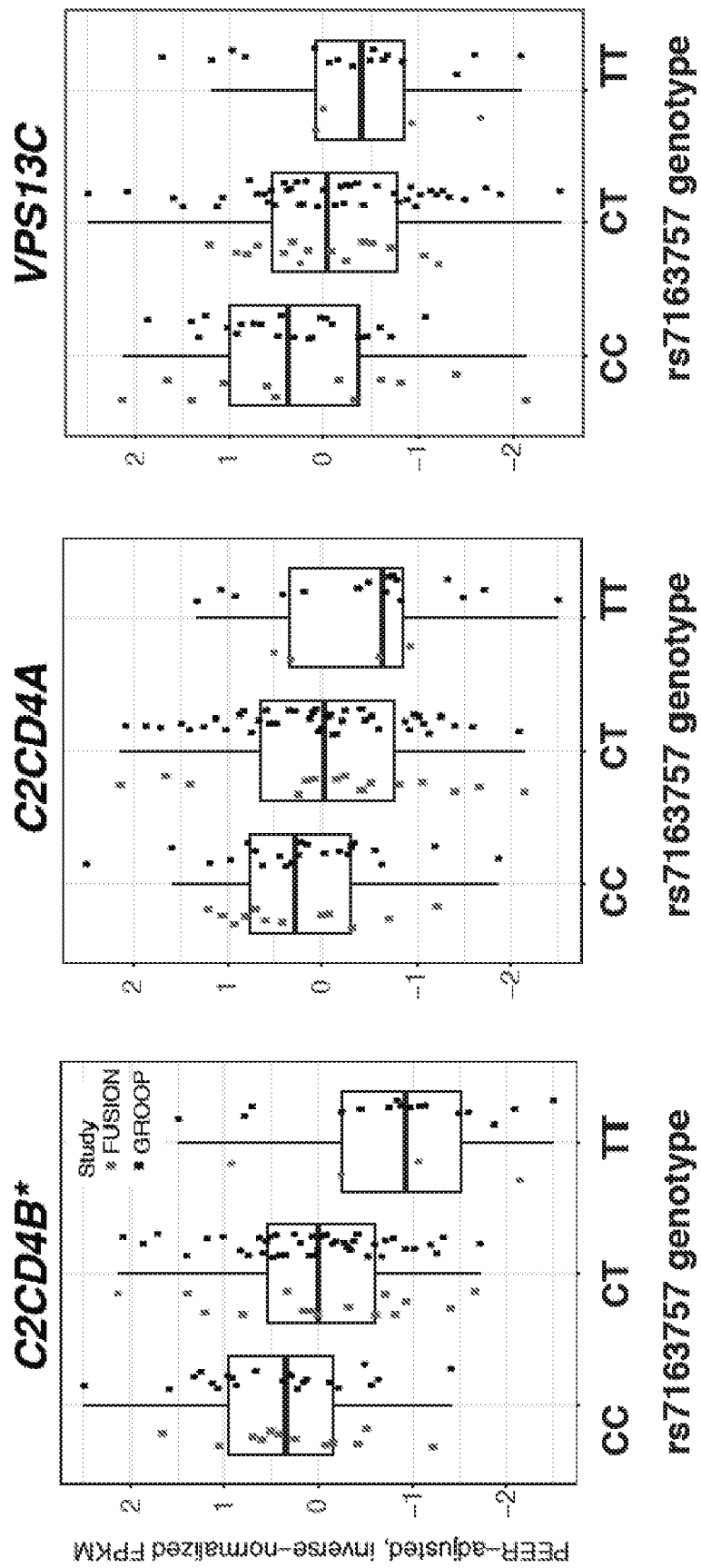
FIGS. 5A-5F. Islet C2CD4B and C2CD4A expression is increased by rs7163757 T2D risk allele (C) and induced by diabetogenic inflammatory cytokines.

Example 5. Increased Islet C2CD4B and C2CD4A Expression is Linked to the Fine-Mapped Putative Causal Variant(s) and Inflammatory Stress Response To identify the putative target gene(s) of the fine-mapped variants (Table 1), associations between rs7163757 genotype and expression of genes with transcription start sites residing within 1 megabase (Mb) of this putative functional variant (Methods) were examined in a recent study of 112 Caucasian islet samples[34] and in multiple tissues examined by the Genotype-Tissue Expression (GTEx) Consortium[53-55]. C2CD4A and C2CD4B were robustly expressed in islets and only selectively among other GTEx tissues, contrasting with the wide expression of VPS13C. The rs7163757 (C) risk allele was significantly associated with increased C2CD4B expression in both islet cohorts (FIG. 5A). Conditional analysis (Methods) indicated that rs7163757 was associated with C2CD4B expression independently of other variants in the region). Although not reaching statistical significance after genome-wide testing correction, C2CD4A also exhibited a trend of increased expression with increasing risk allele dosage in islets.

Figure 5B:
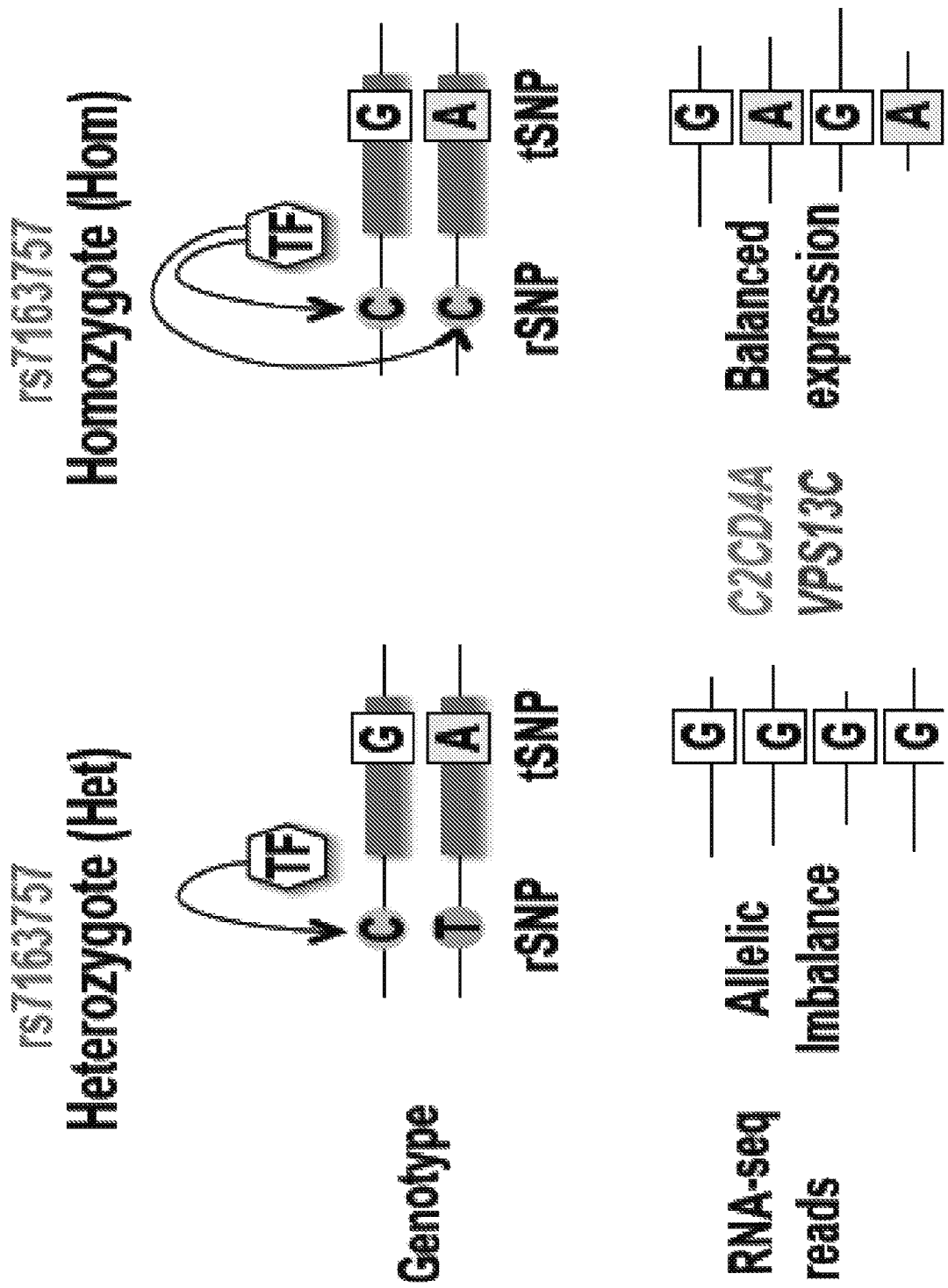
Figure 5C:
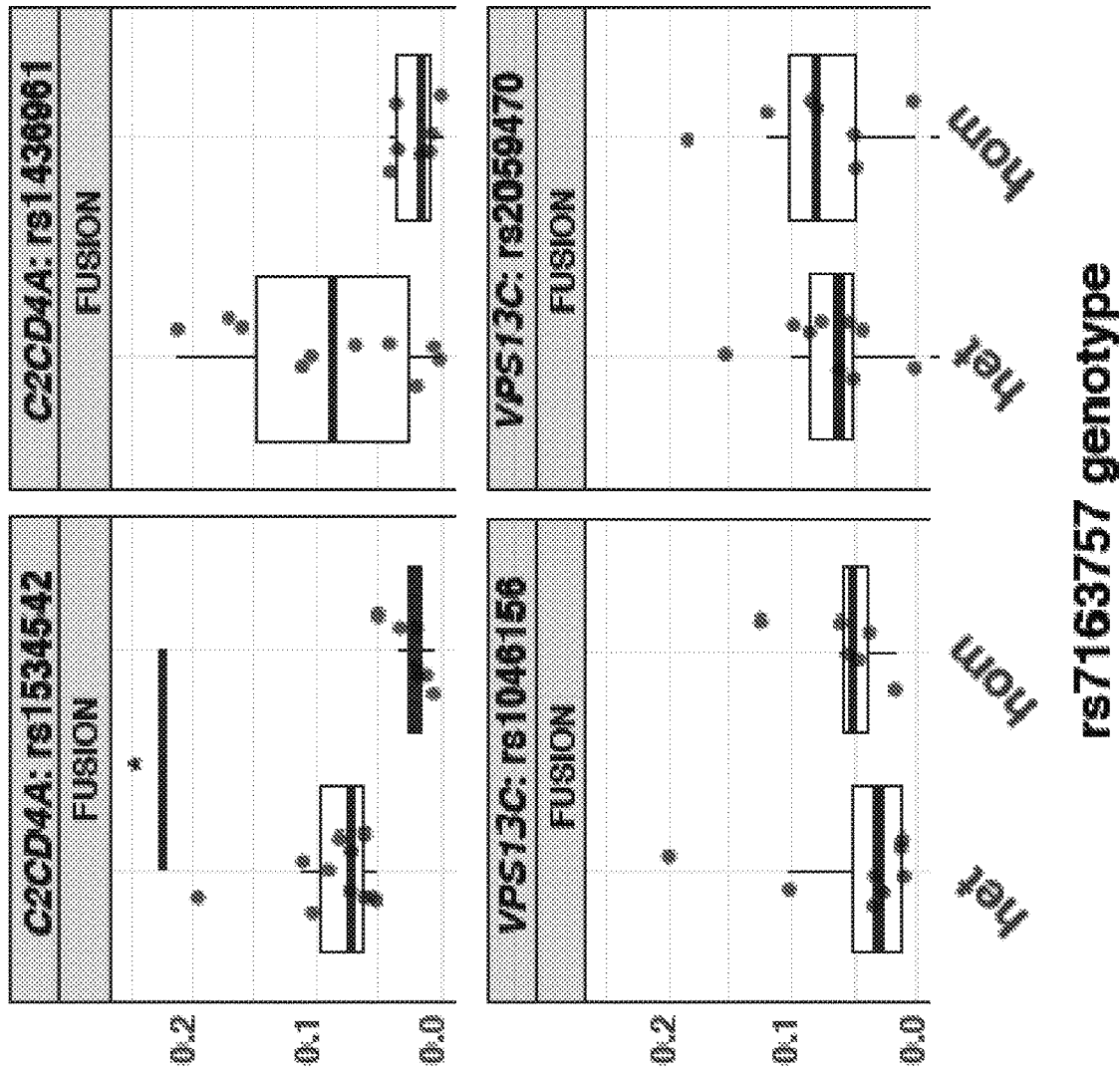

To assess further the potential links between rs7163757 genotype and C2CD4A and/or VPS13C expression, allele-specific eQTL (aseQTL) analyses[43] of transcribed SNPs (FIG. 5B, tSNPs) was completed to determine the relative abundance of C2CD4A and VPS13C mRNA transcripts produced from the maternal and paternal chromosomes within each islet sample. Specifically, studies were performed to determine if RNA-seq reads from deeply sequenced FUSION islet samples heterozygous for the putative rs7163757 regulatory SNP (FIG. 5B, rSNPs) exhibited increased allelic expression imbalance (AEI) for C2CD4A or VPS13C compared to rs7163757 homozygous islet samples. rs7163757 heterozygous FUSION islet samples exhibited significantly higher allelic expression imbalance for the C2CD4A tSNP rs1534542 (Storey's FDR <0.01) and a trend of increased AEI for C2CD4A tSNP rs1436961 (FIG. 5C). These tSNPs did not exhibit significant AEI differences in Groop islet samples, which may reflect differences in islet processing and culture times or the substantially lower RNA-seq coverage of tSNPs in these samples compared to FUSION samples. In both islet cohorts, no significant AEI differences between rs7163757 heterozygote and homozygote islet samples were observed for any VPS13C tSNPs (FIG. 5C).

Figure 5D:
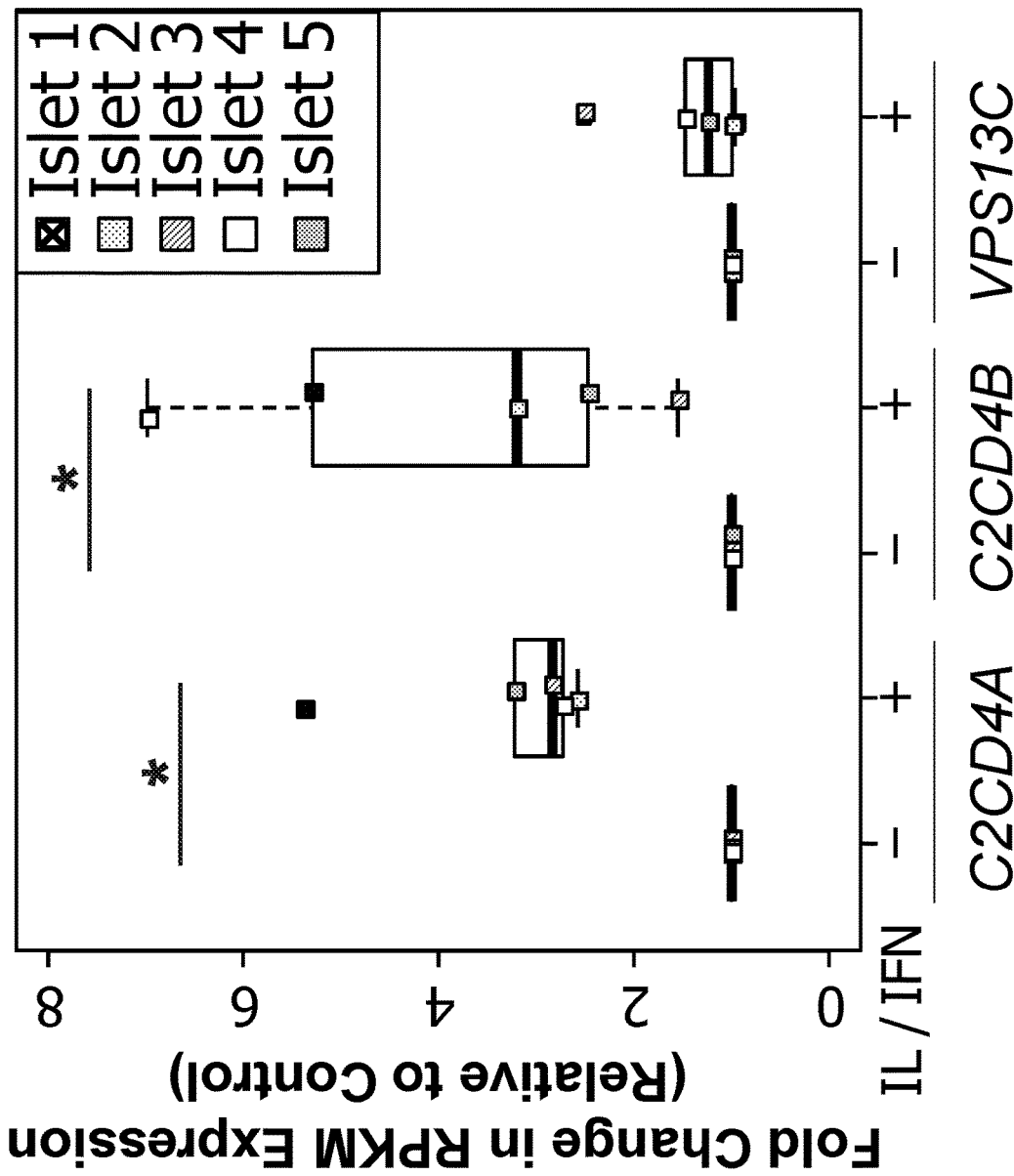
Figure 5F:
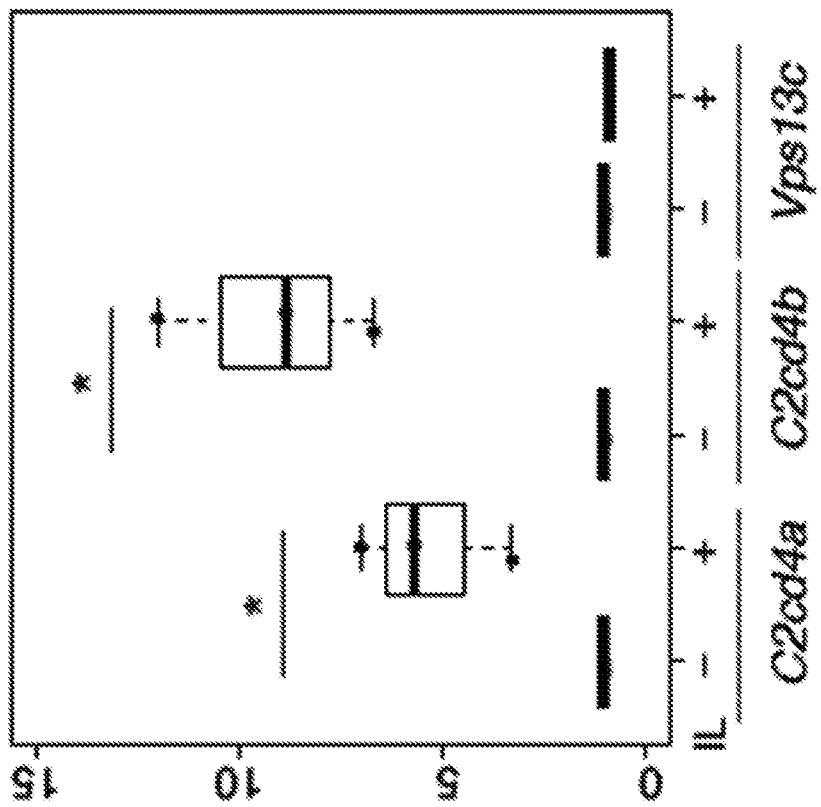
Figure 5E:
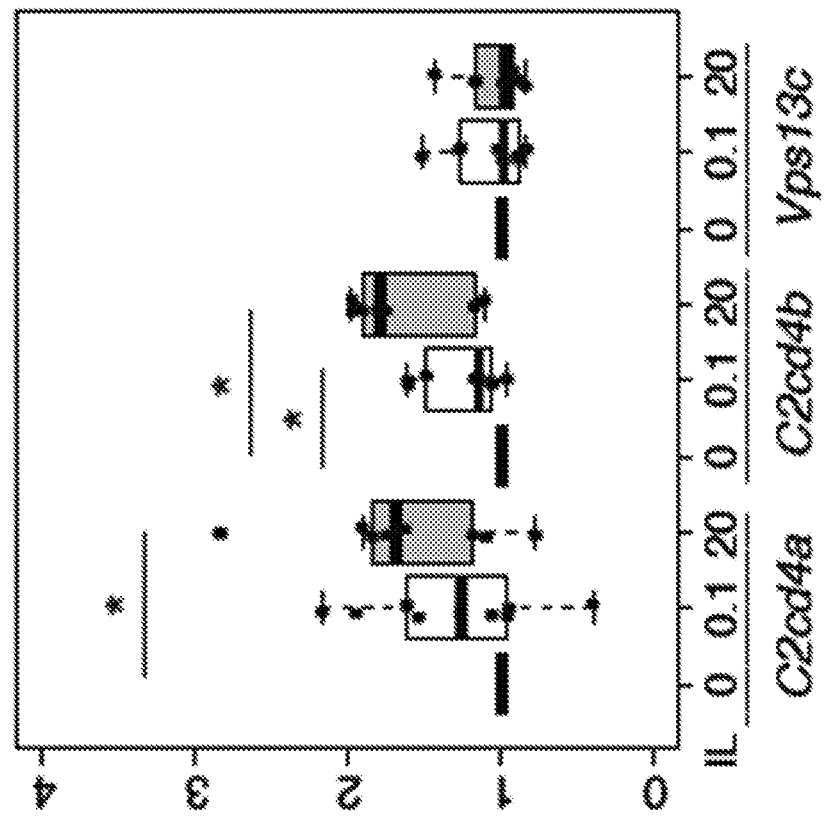

Both C2CD4A and C2CD4B expression are induced by inflammatory cytokines in endothelial cells[56]. To determine if C2CD4A, C2CD4B, and/or VPS13C expression are induced by these diabetogenic stressors[57] in islets/beta cells, RNA-seq data from human[46] and rat[47] islets exposed to inflammatory cytokines were analyzed. As shown in FIGS. 5D and 5E, both C2CD4A and C2CD4B expression, but not VPS13C expression, were induced by inflammatory cytokines in human and rat islets. Similarly, IL-1β induced both C2cd4a and C2cd4b in INS-1(832/13), while Vps13c was unaffected (FIG. 5F). Taken together, these data link the rs7163757 proinsulin-raising and T2D risk (C) allele to increased C2CD4B, and possibly C2CD4A, expression and implicate induction of C2CD4A and C2CD4B, but not VPS13C, in islet/beta cell responses to diabetogenic stressors.

Example 6. NFAT Potentiates Risk Allele Enhancer Activity

Figure 6A:
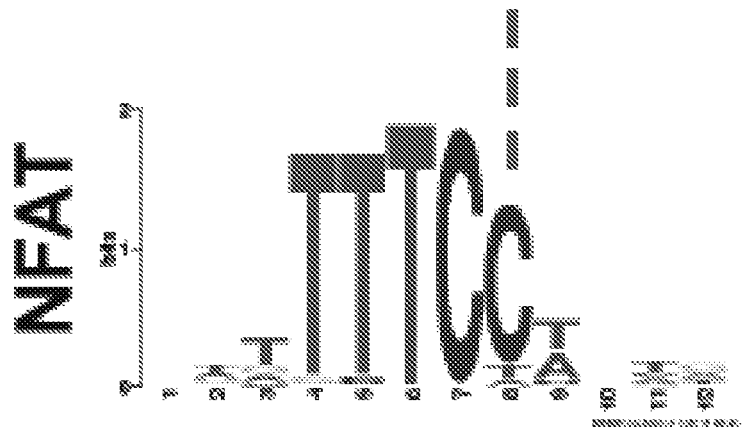
FIGS. 6A-6E. NFAT modulates rs7163757 risk allele (C) enhancer activity.
Figure 6B:
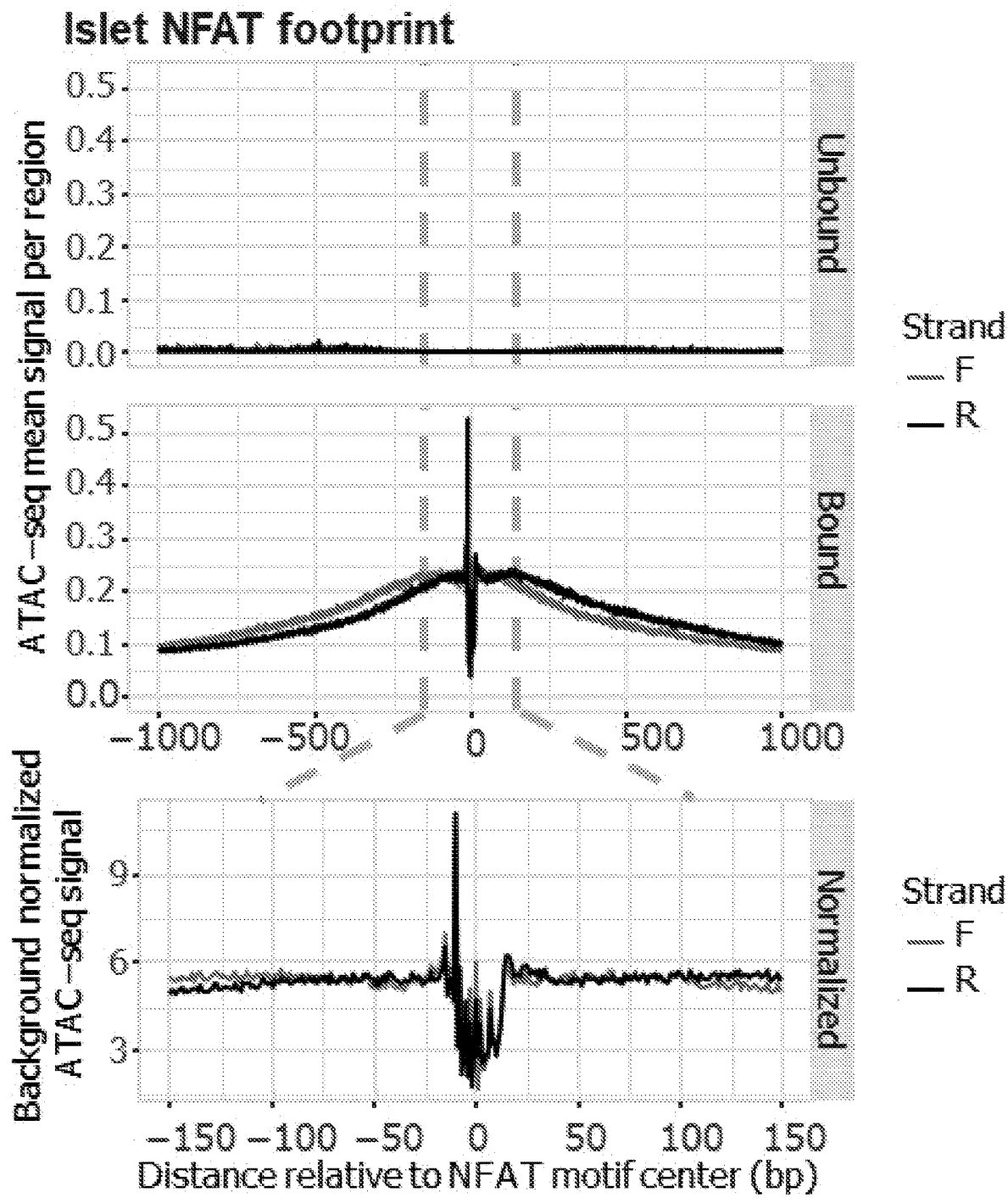

This next study sought to identify plausible trans-factors that could mediate the increased rs7163757 (C) allele enhancer activity observed in FIG. 4B. HaploReg v4.1[58] predicts the rs7163757 (C) risk allele, which exhibited increased enhancer activity (FIG. 4B), to create high affinity DNA binding motifs for the NFAT or IKZF2/Helios transcription factors (TFs) (FIG. 6A). Genes encoding IKZF2/Helios (IKZF2 [MIM 606234]) and multiple members of the NFAT TF family (NFATC1 [MIM 600489], NFATC2 [MIM 600490], NFATC3 [MIM602698], and NFATC4 [MIM 602699]) are expressed in human and mouse islet cells, MIN6, and INS-1(832/13) (not shown). It was hypothesized that the NFAT TF family was the mediator of the rs7163757 risk allele effects because (1) calcineurin/NFAT has well-described roles in islet physiology[59-62] and pathophysiology[63-65], including a recent report implicating NFAT isoforms as regulators of several putative T2D genes in mouse and human islets[66]; (2) NFAT modulates transcriptional inflammatory responses[64], and the putative rs7163757 target genes, C2CD4B and C2CD4A, are induced by inflammatory cytokines in islets and beta cells (FIGS. 5D-5F); (3) the rs7163757 risk/non-risk alleles alter a high information content site in the NFAT position weight matrix (FIG. 6A; PWM); and (4) NFAT footprints (FIG. 6B) in the ATAC-seq open chromatin site overlapping rs7163757 in both human islets (FIG. 3) were detected, which were both C/T heterozygotes.

Figure 6C:
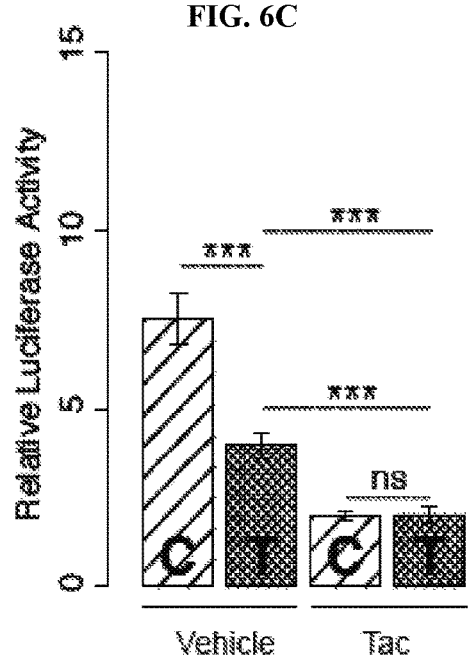

To test this hypothesis, pharmacologic inhibition of the calcineurin/NFAT pathway by tacrolimus (FK506) was first examined to determine how it would affect HS3 risk and non-risk allele enhancer activity. Calcineurin-mediated dephosphorylation is essential for NFAT translocation from the cytosol to nucleus[67], and tacrolimus inhibits this process. The effect of tacrolimus treatment on enhancer activity in MIN6 was tested, and it was found that it abrogated increased enhancer activity of the rs7163757 risk allele (C) to that of the rs7163757 non-risk (T) allele levels (FIG. 6C, compare C and T alleles' activity in "Tac" vs. "Veh" controls). These data thus provide pharmacologic evidence for the calcineurin/NFAT pathway as a mediator of rs7163757 risk allele effects.

Figure 6D:
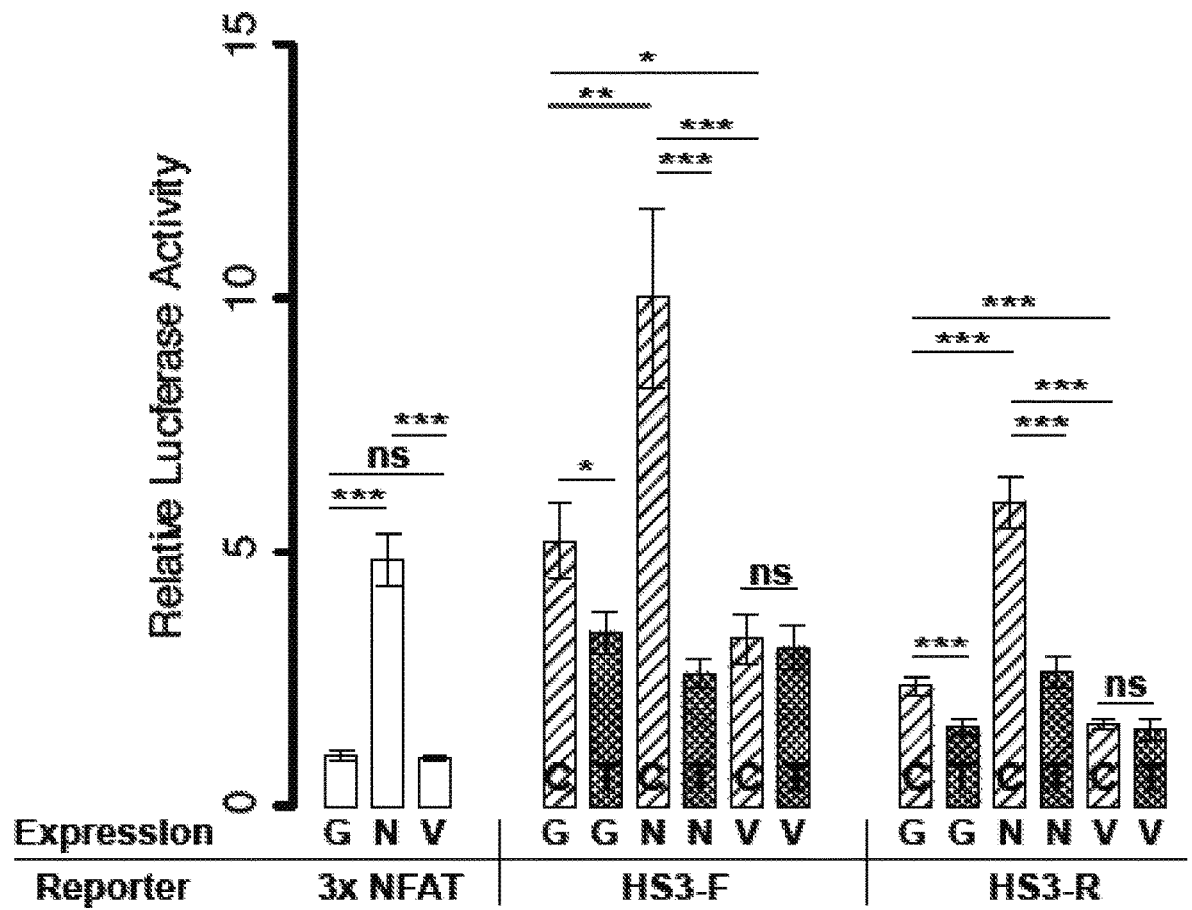

Next, studies tested how molecular manipulation of NFAT affected HS3 enhancer activity. MIN6 cells were co-transfected with the HS3 luciferase vector and plasmids expressing GFP-tagged NFATc1. Furthermore, since a peptide sequence ("VIVIT" (SEQ ID NO: 16)) has been shown to selectively inhibit calcineurin-NFAT interactions and NFAT activity[37,67], studies also tested HS3 activity when co-transfected with GFP-tagged VIVIT (SEQ ID NO: 16) to inhibit NFAT activity in the cells. As a positive control, each expression vector was co-transfected with a luciferase reporter plasmid containing three canonical NFAT binding sites (NFAT Reporter). Expression of GFP alone ("G"), NFATc1 alone ("N"), or VIVIT (SEQ ID NO: 16) alone ("V") did not alter transcriptional activity of the empty luciferase vector (pGL4.23, not shown). As expected, NFATc1 expression in MIN6 cells enhanced luciferase activity of the NFAT Reporter five-fold (FIG. 6D). Importantly, NFATc1 expression specifically potentiated enhancer activity of HS3 sequence containing the rs7163757 risk allele (C) compared to the non-risk allele (T) in both forward and reverse orientations (FIG. 6D, compare alleles in "N" groups). Expression of the inhibitory VIVIT (SEQ ID NO: 16) peptide GFP fusion reduced HS3 risk allele enhancer activity to that of the non-risk allele in both orientations (FIG. 6D, compare alleles in "V" groups). Microscopic analysis of the transfected cells indicated confirmed comparable GFP-VIVIT (SEQ ID NO: 16) and EGFP protein levels, both of which were more robust than the NFATc1 GFP fusion. This strongly suggests that NFAT-potentiated HS3 risk allele enhancer activity was not merely the consequence of more robust NFAT expression. Together, these results support the hypothesis that NFAT mediates increased enhancer activity of the rs7163757 risk allele.

Figure 6E:
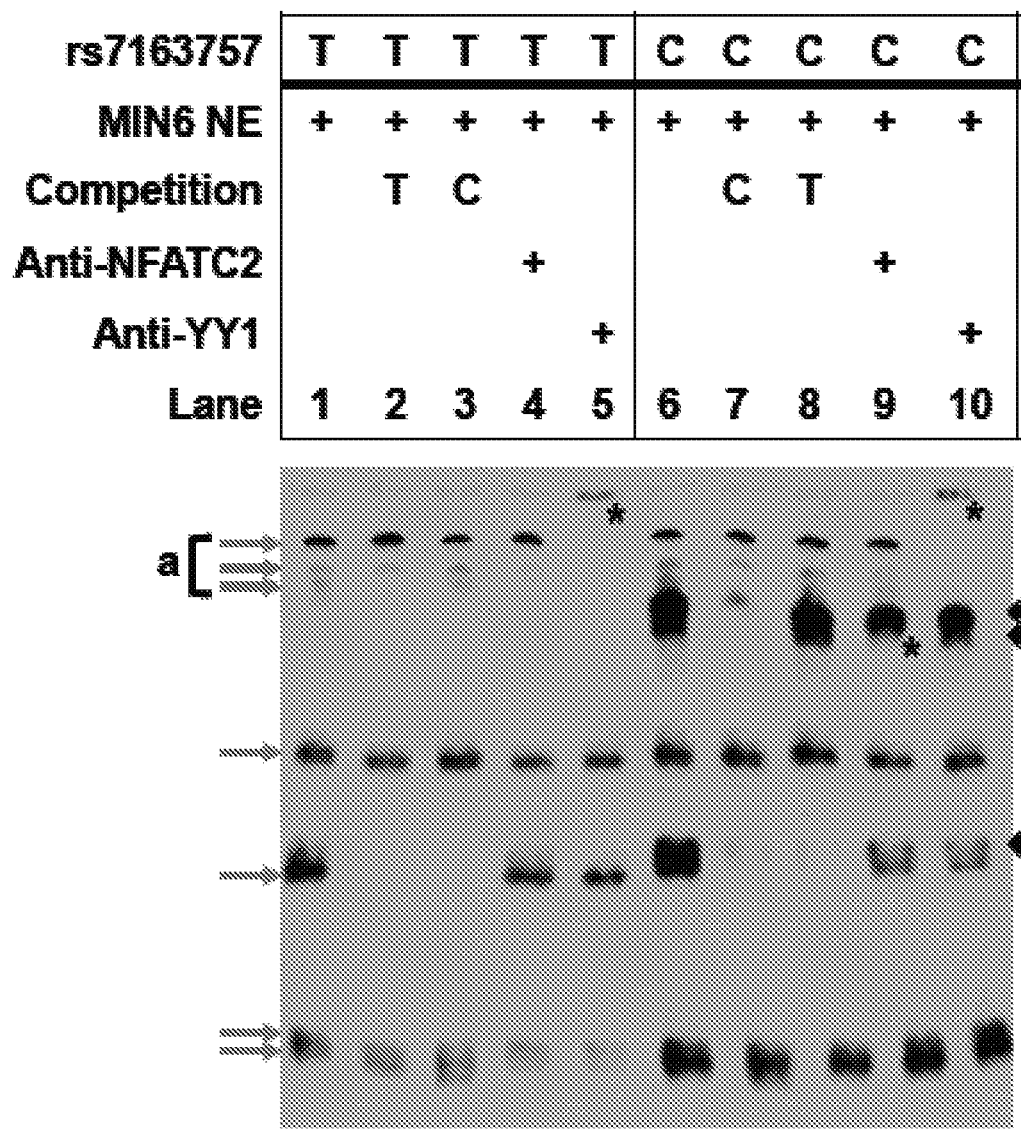

Finally, to determine if the risk and non-risk alleles are bound by different beta cell nuclear proteins/complexes, DNA probes containing the rs7163757 risk allele (C) or the non-risk allele (T) were incubated with MIN6 beta cell line nuclear extracts (NE) and looked for electrophoretic mobility differences of the resulting protein-DNA complexes. As shown in FIG. 6E, electrophoretic mobility shift assays revealed that the risk allele was bound by beta cell nuclear factors not bound to the non-risk allele (bands b, c, and d, compare lanes 1 and 6). Incubation of each labeled probe with excess unlabeled probe containing the risk or non-risk allele allowed us to determine the allele specificity of these complexes, revealing that complexes 'b' and 'c' were specifically disrupted by the risk allele (FIG. 6E, compare lanes 7 and 8). Finally, studies tested for the presence of candidate transcription factors and cofactors in the complexes binding this transcriptional enhancer sequence. Supershift and disruption of complex 'a' was observed when YY1 (FIG. 6E, asterisks in lanes 5 and 10) and p300 antibodies were co-incubated with the extract and probes, respectively, providing in vitro support that this sequence is bound by enhancer-associated cofactors. Addition of anti-FOXA2, MAFB, NKX6.1, and PDX1 antibodies disrupted several of the complexes formed with risk and non-risk alleles, providing in vitro support of the in vivo binding of this site, as determined by ChIP-seq in human islets[16]. Importantly, NFATc2 antibody completely disrupted the risk (C) allele-specific complex 'c' (FIG. 6E, asterisk, lane 9) and reduced complex 'd' binding (FIG. 6E, lane 9). These data indicate that rs7163757 risk and non-risk alleles are both bound by enhancer-associated cofactors YY1 and p300, consistent with in vivo chromatin accessibility and published islet transcription factor binding, but that the risk (C) allele is bound by additional nuclear factors, including NFAT. These data do not eliminate the possibility that other factors, such as IKZF/Helios, may bind and modulate risk allele enhancer activity. However, the luciferase reporter and EMSA results together provide pharmacologic, molecular, and biochemical evidence supporting one or more NFAT isoform as a factor that binds to and potentiates rs7163757 risk allele enhancer activity.

GWAS have identified over 150 loci contributing genetic susceptibility to islet dysfunction and T2D. The vast majority of GWAS SNPs associated with T2D and related molecular traits (e.g., fasting glucose, fasting insulin, 2-hour glucose, glucose-stimulated insulin secretion) reside in non-coding regions of the genome. Identifying (1) the causal variant(s), (2) their target gene(s), and (3) their direction(s) of effect for T2D risk (i.e., gain- or loss-of-function) at each associated locus is important to better understand the molecular genetic pathology underlying islet dysfunction and T2D, and to determine therapeutic suitability. In this study, genetic fine-mapping and functional genomic techniques was applied to refine the proinsulin and T2D association signal on 15q22.2 and address these three important questions. After identifying sixteen intergenic non-coding variants, functional (epi)genomics and experimental analyses was applied to implicate rs7163757 as the most likely functional variant, to identify C2CD4B, and likely C2CD4A as putative target genes of this human pancreatic islet enhancer SNP, and to link C2CD4A and C2CD4B induction with islet inflammatory stress responses. The T2D risk and proinsulin-raising allele (C) exhibits increased enhancer activity and is differentially bound by beta cell nuclear factors in vitro. Moreover, pharmacologic and molecular manipulation of the calcineurin/NFAT pathway combine with in vitro evidence to suggest that one or more of the NFAT TFs can bind to the risk allele and potentiate its enhancer activity. Taken together, these results implicate gain-of-function effects of the rs7163757 risk allele (C) on an evolutionarily conserved islet SE and increased C2CD4B (and likely C2CD4A) expression as a molecular mechanism underlying the 15q22.2 genetic association with increased proinsulin levels and T2D.

Human pancreatic islet eQTL and aseQTL analyses link increased C2CD4B expression, and potentially C2CD4A, to the T2D risk and proinsulin-increasing rs7163757 allele (C). While rs7163757 is detected as a lung eQTL for C2CD4A by the Genotype Tissue Expression Consortium[53-55], the link between rs7163757 genotype and C2CD4B expression appears to be unique to islets. C2CD4A and C2CD4B, but not VPS13C, are induced by proinflammatory cytokines in islets and beta cells. Moreover, in vitro and in vivo data strongly suggest that the risk allele increases enhancer activity and C2CD4B and C2CD4A expression. Notably, the trend of increased expression was consistent between RNA-seq profiles obtained from two independent islet cohorts[34,42], supporting the robust and reproducible nature of these observations. These results contrast with a previous report linking the rs7163757 risk allele to decreased enhancer activity and female-specific decreases in VPS13C and C2CD4A expression among 40 female islet samples[68]. Targeted functional studies will provide important insights to resolve this apparent discrepancy; these data, however, challenge the existing model suggesting female-specific decreases in VPS13C and C2CD4A expression as the mechanism(s) underlying rs7163757 risk allele association with islet dysfunction and T2D. Together, these data clearly motivate future studies to determine the role(s) that C2CD4B and/or C2CD4A may play in pathogenic or compensatory islet stress responses and to determine how these may be exploited to prevent and/or treat T2D.

SEs[14,15,51] are important transcriptional regulatory regions that govern cell type-specific functions. In human islets, genes encoding proteins involved in glucose sensing (e.g., GCK), insulin secretion (e.g., INS, ABCC8/KCNJ11), and islet cell identity (e.g., TFs PDX1, MAFA [MIM 610303], NKX6.1 [MIM 602563]) overlap or are nearby SE chromatin signatures. Evolutionary conservation of the C2CD4A/B/VPS13C SE signature reported here suggests that this locus is also an important region for islet function. rs7163757 resides in this conserved islet SE and the surrounding sequence, HS3, is an open chromatin site and an active enhancer independent of the rs7163757 genotype in human islets as indicated by in vivo islet ATAC-seq and TF ChIP-seq data and in vitro luciferase reporter activity. Consistent with this finding, the rs7163757 risk (C) and the non-risk (T) alleles are both empirically bound by multiple islet TFs according to islet ChIP-seq data[16]. This implies that the risk allele (C) does not create or destroy this open chromatin site, but that the observed increased risk allele (C) enhancer activity (gain-of-function effect) is facilitated by recruiting an additional TF, in this case NFAT, to a canonical binding site created by the risk allele. Such gain-of-function effects have been identified for other T2D-associated loci[69], and "enhancer hijacking" is emerging as a tumorigenic mechanism in cancer[70,71].

Together, the pharmacologic, molecular, and in vitro experiments in this study strongly suggest that NFAT is a TF family that mediates these gain-of-function risk allele effects. The NFAT TF family is linked to both physiologic and pathophysiologic transcriptional responses in islets/beta cells. Physiologically, it directly regulates Ins transcription in pancreatic beta cells in response to increased $Ca^{2+}$, levels and calcineurin activation[62], and pharmacologic calcineurin inhibition decreased human beta cell survival and murine beta cell proliferation[61]. Beta cell-specific deletion of the calcineurin regulatory subunit (Cnb1) in mice resulted in age-dependent diabetes characterized by decreased beta cell proliferation and mass and reduced pancreatic insulin content; conditional expression of active Nfatc1 in $Cnb1^{-/-}$ mice rescued these defects and prevented diabetes[60]. Conversely, islet expression of constitutively active calcineurin in mice resulted in glucose intolerance and loss of beta cell mass due to decreased proliferation and increased apoptosis[65]. Additionally, the NFAT TF family has been implicated in the pancreatic islet/beta cell inflammation response, wherein it mediates TNF alpha expression after exposure to the pro-inflammatory cytokine IL-1β[63]. Recent data suggest that binding partners, such as ERK and JNK, may recruit NFAT to distinct cis-regulatory elements to mediate physiologic and pathophysiologic/inflammatory gene expression responses, respectively[64]. Interestingly, C2CD4A and C2CD4B were both identified as inflammation-responsive genes in endothelial cells, suggesting that they may indeed be co-regulated: C2CD4A and C2CD4B expression increased 30- and 18-fold, respectively, after 2 hours of treatment with IL-1ß in endothelial cells[56]. C2CD4A and C2CD4B expression was three- to five-fold and two- to seven-fold induced, respectively, by IL-1β and IFNγ pro-inflammatory cytokines in human islets[46]; palmitate treatment induced C2CD4A expression three- to four-fold[72]. Three-fold induction of C2CD4A and C2CD4B expression was detected in human pancreatic islets after IL-1B treatment (data not shown). Similarly, a two-fold and three-fold induction of C2cd4a and C2cd4b in INS-1(832/13) was observed in beta cells treated with 2 U/ml IL-1β for 2 hours compared to untreated controls. Finally, C2CD4A was three-fold induced in diabetes-sensitive New Zealand Obese (NZO) mouse islets compared to those of diabetes-resistant B6-ob/ob mice after a carbohydrate challenge[73]. A working model has been proposed wherein the rs7163757 T2D risk allele creates NFAT-mediated/dependent enhancer gain-of-function and inappropriate, enhanced, or extended C2CD4B (and likely C2CD4A) expression in response to islet/beta cell inflammatory stress signaling. Multiple NFAT TF paralogs (NFATC1, NFATC2, and NFATC3) are expressed in islets. Thus, it will be important in future studies to elucidate the specific NFAT family member(s) mediating the rs7163757 risk allele effects and clarify the condition(s) that elicit NFAT binding to this regulatory site in vivo. Moreover, follow-up studies to define the molecular functions of C2CD4B and/or C2CD4A in human islets, and to determine the effect of their overexpression on islet/beta cell (patho) physiology will be critical to understand their roles in T2D pathogenesis and their utility as therapeutic targets to prevent and/or treat T2D.

Example 7. A Role for C2cd4a and C2cd4b in Glucose Stimulated Insulin Secretion (GSIS) in INS-1(832/13) Rat Islet Beta Cell Lines Based on human islet expression and epigenomic data linking the rs7163757 proinsulin raising and type 2 diabetes risk allele to altered C2CD4B, and likely C2CD4A, expression, it was hypothesized that C2cd4a, C2cd4b, or both genes would be required for proper insulin secretion in beta cells. To test this hypothesis, CRISPR/Cas9 was used to delete C2cd4a, C2cd4b, or both genes in INS-1 (832/13) and test the effects of deleting them on basal (3 mM glucose) or glucose-stimulated (15 mM glucose) insulin secretion (GSIS). As shown in FIG. 7C, C2cd4a (−/+) and C2cd4b (+/−) deletion clones exhibited significantly reduced/absent expression compared to wildtype (+/+) clones (p<0.005 for each comparison). Interestingly, C2CD4A expression was approximately seven-fold increase in C2cd4b deletion clones compared to wildtype clones, while no such effect on C2CD4B expression was observed in C2cd4a deletions. Deletion of both genes (FIG. 7C, −/−) resulted in undetectable C2CD4A or C2CD4B expression as anticipated.

After confirming that each targeted deletion resulted in a null allele with no gene expression, how C2cd4a and/or C2cd4b loss-of-function affected GSIS in the mutant beta cell lines was determined. Each single mutant, and the double mutant, did not exhibit insulin secretion differences under basal (3 mM) glucose concentrations (FIG. 7D, compare white bars among all groups). As shown in FIG. 7D, deletion of either C2cd4a (−/+) or C2cd4b (+/−) did not result in significant changes in GSIS compared to wildtype clones (compare gray bars between +/+, +/−, and −/+). Importantly, however, deletion of both genes led to an approximately two-fold reduction in insulin secretion in high (15 mM) glucose concentrations. Together, these data suggest that both C2CD4A and C2CD4B are required for proper glucose-stimulated, but not basal, insulin secretion.

Material and Methods

Fine-mapping Study Population and Phenotype

Genetic association results were reported for fasting pro-insulin levels from up to 8,635 non-diabetic Finnish men from the population-based Metabolic Syndrome in Men (METSIM) study[19]. Study participants with type 1 or type 2 diabetes (previously diagnosed, on diabetes medication, fasting glucose >7 mmol/l or 2-h glucose >11.1 mmol/l) were excluded from analysis. Mean age of analyzed participants was 57.2 years (median=57.0 years; range=45-74 years) and mean body mass index (BMI) was 26.8 kg/m$^2$ (median=26.3 kg/m$^2$; range=16.2 to 51.6 kg/m$^2$). Blood samples were drawn after a 12-h overnight fast and fasting plasma-specific proinsulin (Human Proinsulin RIA Kit, Linco Research; no cross-reaction with insulin or C-peptide) and fasting insulin (ADVIA Centaur Insulin IRI, 02230141, Siemens Medical Solutions Diagnostics; minimal cross-reaction with proinsulin or C-peptide) were measured by immunoassay. The study was approved by the ethics committee of the University of Kuopio and Kuopio University Hospital, and informed consent was obtained from all study participants.

Genotyping and Genotype Imputation

METSIM samples were genotyped with the Illumina HumanOmniExpress Beadchip (Illumina, San Diego, CA, USA). Illumina array probe sequences were mapped to the hg19 genome assembly using BWA[20]. SNP quality control steps prior to imputation included removing SNPs with ambiguously mapping probe sequences and SNPs with call rate <95% or Hardy-Weinberg equilibrium test p-value <10$^{-6}$. A two-step genotype imputation strategy[21] was followed. First, haplotypes were statistically estimated using SHAPEIT2[22] and then imputed genotypes into these estimated haplotypes using minimac2[23]. The haplotypes from 2,737 European individuals sequenced in the Genetics of Type 2 Diabetes (GoT2D) project were used as the imputation reference panel[3]. Participants were previously genotyped with the Illumina HumanExome BeadChip[12], which focuses on protein-altering variants selected from the exome sequences of >12,000 individuals. Exome chip variants were incorporated after imputation.

Fine-Mapping and Conditional Analysis

To account for relatedness between study participants and population structure, associations between the phenotype were tested and the estimated dosages (imputed variants) or additively coded genotypes (directly genotyped variants) using a linear mixed model with empirical kinship matrix, as implemented in EMMAX[24]. Log-transformed plasma pro-insulin was adjusted for age, BMI, and log-transformed insulin before association testing, and analyzed rank-based inverse normal-transformed residuals. Directly genotyped variants were analyzed with minor allele count (MAC) >5 and HWE test p-value >10$^{-6}$, and imputed variants with imputation quality score R$^2$>0.3 and minor allele frequency (MAF) >0.5%.

To identify additional independent signals in the region, a conditional analysis was carried out, in which the allele count of the most strongly associated SNP (rs7172432) was included as a covariate in the model. Regional association results were visualized using LocusZoom[25]. Linkage disequilibrium was estimated from the imputation reference panel.

For the Bayesian fine-mapping analysis, we followed Fuchsberger et al[3]. In brief, we defined the candidate set of variants by identifying all analyzed variants with $r^2>0.1$ with the most associated variant, and within a 5 Mb window centered on the most associated variant. We calculated approximate Bayes' factors (ABF) for each variant as:

$$ABF=\sqrt{1-r}e^{rz^2/2}$$

where $r=0.04/(s.e.^2+0.04)$, $z=\beta/s.e.$, and $\beta$ and s.e. are the log odds ratio estimate and its associated standard error. The posterior probability of being causal for each variant as ABF/T where T is the sum of ABF values over all candidate variants was then calculated. Next, variants were ranked in decreasing order by posterior probabilities and the 99% credible set was obtained by including variants with the highest posterior probabilities until the cumulative posterior probability >99%.

Primary Islet and Cell Culture

Fresh human non-diabetic pancreatic islets were purchased from ProdoLabs (UNOS #ABE1388) in accordance with regulations of Human Subjects research. Upon arrival, the cells were transferred into PIM(S) media (ProdoLabs), supplemented with PIM(ABS) (ProdoLabs) and PIM(G) (ProdoLabs) and kept in a T-150 non-tissue culture treated flask (VWR) for recovery at 37 C and 5% $CO_2$ overnight. ATAC-seq and RNA-seq were performed the following day as described below.

Mouse MIN6 and rat INS-1(832/13) (a kind gift from C. Newgard) beta cell lines were cultured as previously described[26,27]. Briefly, MIN6 were grown in DMEM (4.5 g/l Glucose) (Life Technologies) supplemented with 1 mM Sodium Pyruvate (Life Technologies), 100 mM 2-Mercaptoethanol (Sigma), and 10% Fetal Bovine Serum (Seradigm). INS-1(832/13) cells were cultured in RPMI-1640 (11.1 mM D-glucose) (Life Technologies) supplemented with 10% Fetal Bovine Serum (Seradigm), 10 mM HEPES (Life Technologies), 2 mM L-glutamine, 1 mM sodium pyruvate, and 50 mM 2-Mercaptoethanol (Sigma).

Chromatin Analyses (ChIP-seq and ATAC-seq)

Crosslinking and ChIP-seq of human islets, MIN6, and INS-1(832/13) beta cells were carried out as described[28]. Human islet, MIN6, and INS-1(832/13) beta cell line ATAC-seq libraries were prepared as described[29]. Approximately 250 islet equivalents (~250,000 islet cells), 250,000 INS-1 (832/13) cells, and 50,000 MIN6 cells were transposed.

Sequence Alignment, Processing, and Analysis

Chromatin states were determined using ChromHMM as described[14]. ATAC-seq reads were aligned to hg19 (human islets), mm9 (MIN6), and rn5 (INS-1(832/13)) reference genomes using BWA[20] with 'mem' option. Only reads uniquely mapping to their respective genomes were used in subsequent analysis. Reads mapping to the mitochondrial genome (chrM) were removed, and duplicate reads mapping to the nuclear genome were eliminated to avoid potential PCR amplification artifacts in ATAC-seq. Human islet, MIN6, and INS-1(832/13) ATAC-seq library and data statistics were collected. ATAC-seq enriched regions (peaks) in each sample or merged replicates were identified using the MACS2[30] program with the following parameters: MACS/ 2.1.0.20151222/bin/macs2 callpeak-t<input tag file>-f BED-n<output peak file>-g 'hs'—nomodel—shift-100—extsize 200-B.

RNA-seq

Human islet RNA-seq data and tracks were previously described[14]. Additionally, total RNA was extracted and purified from 32 Caucasian human pancreatic islet samples procured from IIDP and NDRI, MIN6, and INS-1(832/13) beta cell lines using Trizol (Life Technologies) according to the manufacturer's instructions, and sequenced using the Illumina TruSeq (human islets, MIN6) or Kapa Biosystems KAPA mRNA-seq (INS-1(832/13)) kits according to the manufacturer's instructions. MIN6 RNA-seq data were aligned to mm9 using tophat v1.3.2[31]. For INS-1(832/13) RNA-seq, the gene models for C2cd4a, C2cd4b and Vps13c were absent in the current version of the UCSC rn5 gene annotations (Illumina iGenomes). A reference guided transcriptome assembly was performed using cufflinks (v2.2.1) to construct the transcript models[31]. The assembled transcripts were then visualized on the UCSC genome browser and gene locations identified by homology to mouse annotations. Transcript models for each locus were collapsed to generate the corresponding gene model. These gene models were added to the existing rn5 gene annotations and a reference index created using RSEM[32] (v.1.12.2). RNA-seq reads were realigned to this reference index using RSEM to generate alignments and count matrices. INS-1(832/13) UCSC genome browser tracks were created using homer (v4.6)[33].

Human islet ATAC-seq footprint analysis

Transcription factor binding predictions in human islet ATAC-seq data were performed as described[34]. Briefly, matrices that represent the Tn5 integration events ±100 bp around position weight matrix (PWM) scan matches for a given motif were generated. These matrices were used as input for CENTIPEDE[35] to calculate the posterior probability of each motif instance being bound. Individual motifs were considered bound if the CENTIPEDE posterior was greater than or equal to 0.99 and the motif coordinates were completely intersecting an ATAC-seq peak in the sample of origin.

Stretch/Super Enhancer (SE) Constituent Sequence Cloning and Site-directed Mutagenesis Human SE constituent sequences from the region on chr15: 62363117-62455736 (GRCh37/hg19 coordinates), between C2CD4A and C2CD4B, were cloned. SE constituent site sequences were PCR amplified from islet genomic DNA (gDNA) of two individuals with different genotypes (Haplotype 1 and Haplotype 2) at several of the SNPs in this region using Phusion high fidelity polymerase (Thermo Scientific). Amplicons were cloned into pDONR201 and shuttled into modified pGL4.23 luciferase reporter vectors using Gateway cloning (Invitrogen) as previously described[28]. HS3 rs7163757 (C) and (T) alleles were interconverted using primer sequences (not shown) and the QuikChange Lightning site-directed mutagenesis kit (Agilent Technologies) according to the manufacturer's instructions.

Transfection and Dual Luciferase Reporter Assays

MIN6 or INS-1(832/13) cells were seeded at a density of 60,000 cells per well in 96-well-plates 24 hours prior to transfection. Cells were co-transfected in triplicate with 200 ng of pGL4.23 containing each human C2CD4A/B SE sequence and 2 ng Renilla (pRL-TK) using Lipofectamine 2000 Transfection reagent (Life Technologies) according to the manufacturer's instructions. Between four and sixteen clones were tested per C2CD4A/B SE sequence and orientation. Each plasmid was transfected and measured in triplicate, and experiments were completed on at least three separate occasions. 38-40 hours after transfection, cells were lysed in 1× Passive Lysis Buffer (PLB) using the Dual Luciferase Reporter Assay system (Promega) according to the manufacturer's instructions. Luciferase was measured on a Synergy2 Microplate Reader (BioTek). Firefly values were normalized to Renilla to control for differences in cell number or transfection efficiency. To determine glucose-stimulated activity of the reporters, INS-1(832/13) cells were grown in INS-1(832/13) media containing reduced glucose (3-5 mM) for 8-10 hours prior to transfection with the C2CD4A/B HS3 reporter plasmids. Transfected cells were cultured in reduced glucose medium for an additional 16 hours, after which they were grown in high (15 mM) or low (3 mM) glucose-containing medium for an additional 24 hours prior to cell lysis in 1× PLB and luciferase reporter activity measurement as described above. At least three plasmid preparations were tested for each HS3 allele on three separate occasions.

Pharmacologic inhibition of calcineurin/NFAT: MIN6 cells were pre-treated with 10 ng/ml tacrolimus (FK506) (Biotang) or ethanol vehicle control 30 minutes prior transfection with 200 ng of the C2CD4A/B SE firefly luciferase vectors and 2 ng Renilla (pRL-TK). Luciferase activity was tested as above for between four and five clones on three separate occasions.

Molecular manipulation of the Cn/NFAT pathway: 200 ng of the C2CD4A/B SE luciferase vectors were co-transfected in triplicate with 100 ng of plasmids expressing wildtype NFAT (EGFPC1-huNFATc1EE-WT[36]; Addgene, plasmid #24219) or a mutant NFAT peptide sequence (EGFPN1-VIVIT[37] (SEQ ID NO: 16); Addgene, plasmid #11106). pGL3-NFAT-luciferase[38] (Addgene, plasmid #17870), which contains 3 canonical NFAT binding sequences, was used as a positive control to measure NFAT activity and transcriptional responses in these experiments. GFP intensity was documented (GFP-channel=60% light intensity; Transmitted=53% light intensity) for all cells transfected with EGFPC1-huNFATc1EE-WT, EGFPN1-VIVIT (SEQ ID NO: 16), and pEGFP-C1 (Clontech, catalog #6084-1) expression constructs using an EVOS FL Cell Imaging System (Life Technologies) to confirm GFP fusion protein levels for each co-transfected expression plasmid. For these experiments, four independent clones were selected and tested on four separate occasions.

Islet SNP Genotyping and Imputation

Islet DNA samples were genotyped at the Genetic Resources Core Facility (GRCF) of the Johns Hopkins Institute of Genetic Medicine on the HumanOmni2.5-4v1_H BeadChip array (Illumina, San Diego, CA, USA). The same quality control criteria was applied to SNPs for further analysis as described for the METSIM samples. In addition, we filtered out A/T or C/G SNPs with MAF >0.2, or SNPs that have absolute alternate allele frequency difference >0.2 with 1000G EUR population, yielding 2,057,703 SNPs for imputation. SNP imputation and phasing was performed using the same strategy as described for METSIM samples. Haplotypes from 1000G phase3 v5[39] were used as the reference panel. To improve phasing quality given the small target sample set, samples were pre-phased together with the 2,504 reference panel samples using ShapeIT2[22].

Islet Expression Quantitative Trait Locus (eQTL) lookups and Conditional Analysis Cis-eQTL data for each gene (n=10) whose most upstream TSS was within 1 Mb of rs7163757 were obtained from a parallel study of expression in 112 human islets[34]. To determine whether cis-eQTL associations between rs7163757 and nearby genes could be affected by other strong eQTLs in the region, iterative conditional analysis was performed on each of these genes. The following linear regression model, fit within the two islet studies (n=31 and n=81) from Varshney et al[33] was used:

$$y_{ij} = \alpha + \beta_{jSNP} G_{iSNP} + \beta_{js} G_{is} + \varepsilon_{ij}$$

$Y_{ij}$ is the inverse-normalized and PEER-adjusted FPKM value for individual i and gene j, $G_{iSNP}$ is the imputed allele count of rs7163757, $\beta_{jSNP}$ is the regression coefficient of the imputed allele count for rs7163757, $G_{is}$ is the set of all SNPs within 1 Mb of the most upstream TSS of the gene, and $\varepsilon_{ij}$ is normally distributed with mean zero and variance $\sigma^2$. Only SNPs present in both studies (MAC >1) and with MAC >10 across all 112 samples were considered. The results from the two studies were combined using sample-size weighted meta-analysis[33]. If greater than or equal to one SNP had a meta-analysis p-value <1.2×10⁻⁴ (corresponding to the p-value threshold for cis-eQTLs with FDR <5%), the SNP with the most significant p-value in the model were retained and repeated the procedure until no added SNP had a p-value <1.2×10⁻⁴. This procedure corresponds to performing stepwise forward selection of SNPs within 1 Mb of the most upstream TSS based on the results of the meta-analysis at each step (using a stopping threshold p-value of 1.2×10⁻⁴). The conditional p-value for rs7163757 is the p-value for $\beta_{jSNP}$ from the final model. The Benjamini-Hochberg method[40] was used to adjust the conditional p-values for multiple testing.

Allele Specific Expression (ASE) Quantitative Trait Locus Analysis

ASE was quantified as described[41] using RNA-seq data from FUSION[34] and Groop[42] human islet samples, except stranded RNA-seq reads were considered together. Targeted ASE quantitative trait locus (aseQTL) analysis was performed to identify transcripts impacted by putative regulatory SNPs (rSNPs) in the C2CD4A/B/VPS13C locus. The approach to statistically associate an rSNP genotype with a transcribed SNP's (tSNP) ASE was performed as described[43] with the following modifications: 1) coordinates for all transcription start sites for a given gene were merged and extended 100 kb upstream and downstream; (2) any SNPs in this window were tested as rSNPs; (3) any SNP with quantified ASE that overlapped an exonic region of the gene with at least 30× coverage was tested as a tSNP; and (4) rSNPs and tSNPs were tested in a pairwise, gene-by-gene fashion. For a tSNP/rSNP pair to be tested, we required observing with quantified ASE at least five samples each that were rSNP heterozygotes and homozygotes.

The fraction reference allele (fracRef) value measures ASE at tSNPs and is converted to the absolute allelic imbalance, a value representing the allelic skew from the expected fracRef, for aseQTL analysis. For example, a SNP with fracRef of 0.8 (over-expressed reference allele) or 0.2 (over-expressed alternate allele) and expected fracRef of 0.5 results in an absolute allelic imbalance of 0.3. Allelic imbalance is calculated by taking the absolute value of the difference between the observed fracRef and the sample-specific and allele-pair-specific expected fracRef. Absolute allelic imbalance values range from 0 to 0.5; fracRef values range from 0 to 1. The tSNP absolute allelic imbalance values are compared for homozygous versus heterozygous rSNPs using a two-sided Wilcoxon Rank Sum Test (wilcox.test in R), producing a p-value for every rSNP and tSNP pair tested. Storey's FDR was performed to correct for multiple testing burden on genes within the topologically associating domain (TAD)[44] surrounding C2CD4A, C2CD4B, and VPS13C as opposed to genome-wide. q-values were calculated for each rSNP/tSNP pair within the TAD coordinates chr15:61412708-62612708 (hg19, as determined from hESC and IMR90 TADs[44] using Bioconductor's qvalue package.

Electrophoretic Mobility Shift Assay (EMSA)

EMSAs were carried out as previously described[45]. Briefly, 17 bp biotin end-labeled complementary oligonucleotides were designed surrounding the variant rs7163757 (5' biotin-TGATTTTTC [C/T] ATTTTAAGC-3'(SEQ ID NO: 15), Integrated DNA Technologies) and double-stranded probes were generated for both alleles. Nuclear extract from mouse insulinoma MIN6 cells was prepared using the NE-PER Extraction Kit (Thermo Scientific). The LightShift Chemiluminescent EMSA Kit (Thermo Scientific) was used following the manufacturer's instructions. Binding reactions consisted of 1× binding buffer, 1 µg poly (dI-dC), 4 µg nuclear extract, and 200 fmol labeled probe. Reactions were incubated at room temperature for 25 minutes. For competition reactions, 64-fold excess of unlabeled probe for either allele was included and pre-incubated for 15 min. For supershift assays, 4 µg of antibody (Nkx6.1, sc-15030X; PDX1, sc-14662X; YY1, sc-1703X; p300, sc-585x; FoxA2, sc-9187X; MafB, sc-22830X; NFATc2 (4G6-G5)x, sc-7296X (Santa Cruz Biotechnology); NFATc1(7A6), 556602; BD Biosciences) was added to the binding reaction and pre-incubated for 25 minutes. DNA-protein complexes were detected by chemiluminescence. EMSAs were repeated and yielded comparable results.

Inflammatory Cytokine Induction of C2CD4A, C2CD4B, and VPS13C in Human Islets, Rat Islets, and INS-1 (832/13) Beta Cells Processed RPKM (reads per kilobase of transcript per million mapped reads) values (Dataset S1) were obtained from published studies of 5 human islets treated with IL1-ß and IFN-γ[46] and of rat islets treated with 0.1 or 20 U/ml IL-1ß[47]. INS-1(832/13) cells were incubated in reduced-serum (1% FBS) INS-1(832/13) complete medium overnight, then treated for 2 hours with 0 or 2 U/ml recombinant rat IL-1ß (Biolegend) prior to RNA harvest and processing for RNA-seq as described above.

CRISPR-Cas9-Mediated Deletion of C2cd4a and C2cd4b

Figure 7A:
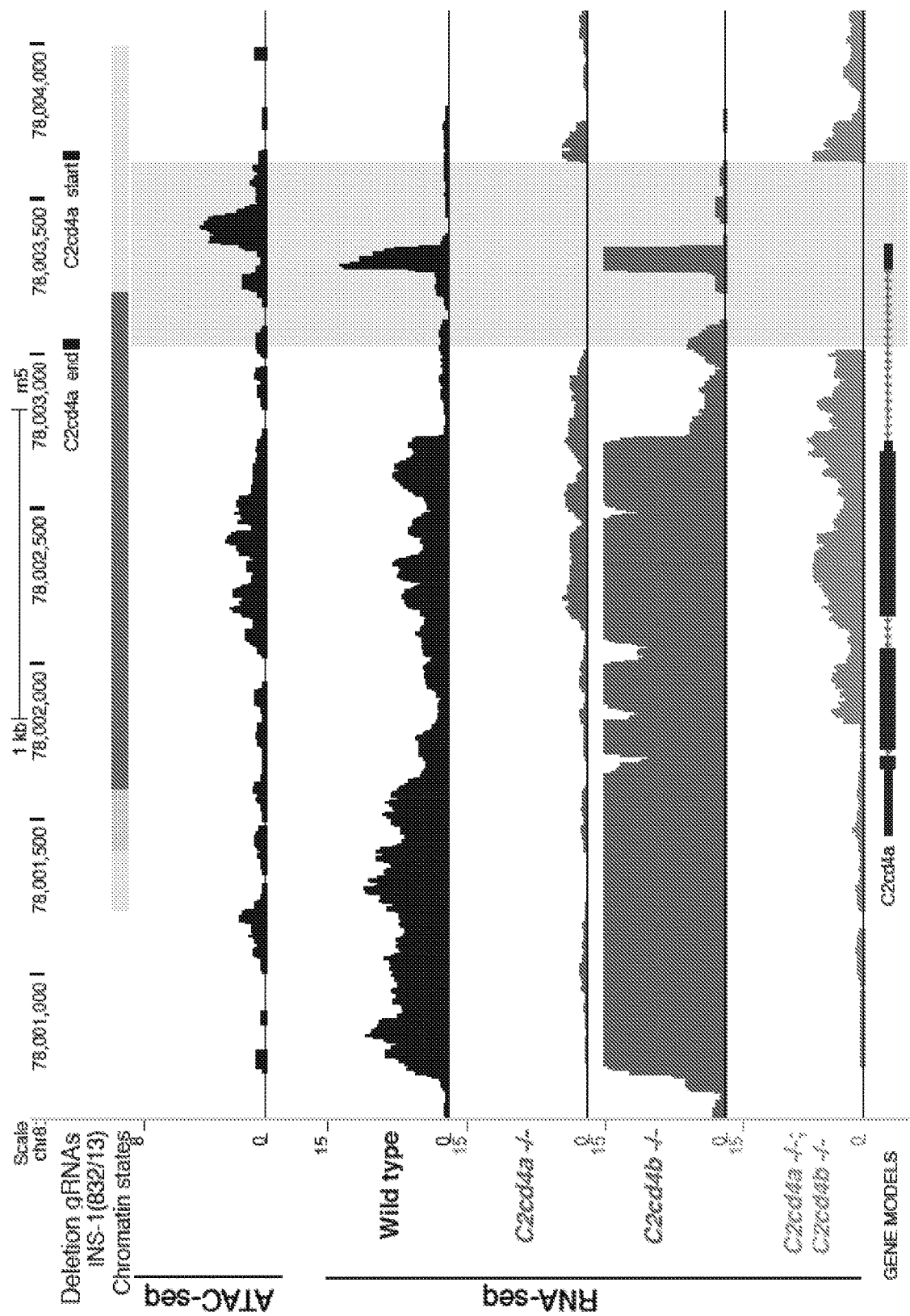
FIGS. 7A-7D. C2cd4a$^{-/-}$; C2cd4b$^{-/-}$ mutant INS-1(832/13) cells exhibit impaired glucosestimulated insulin secretion (GSIS).
Figure 7B:
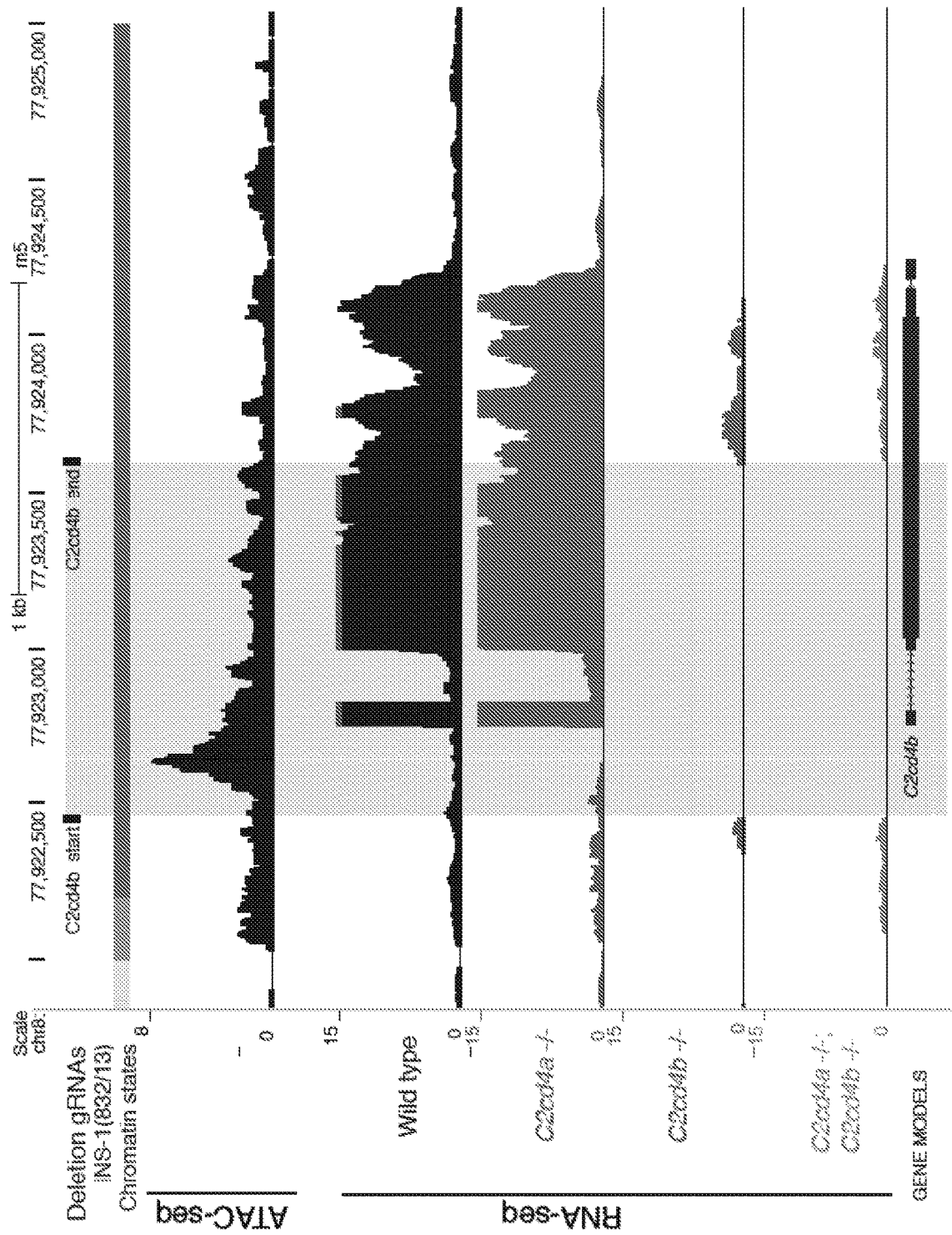
Figure 7C:
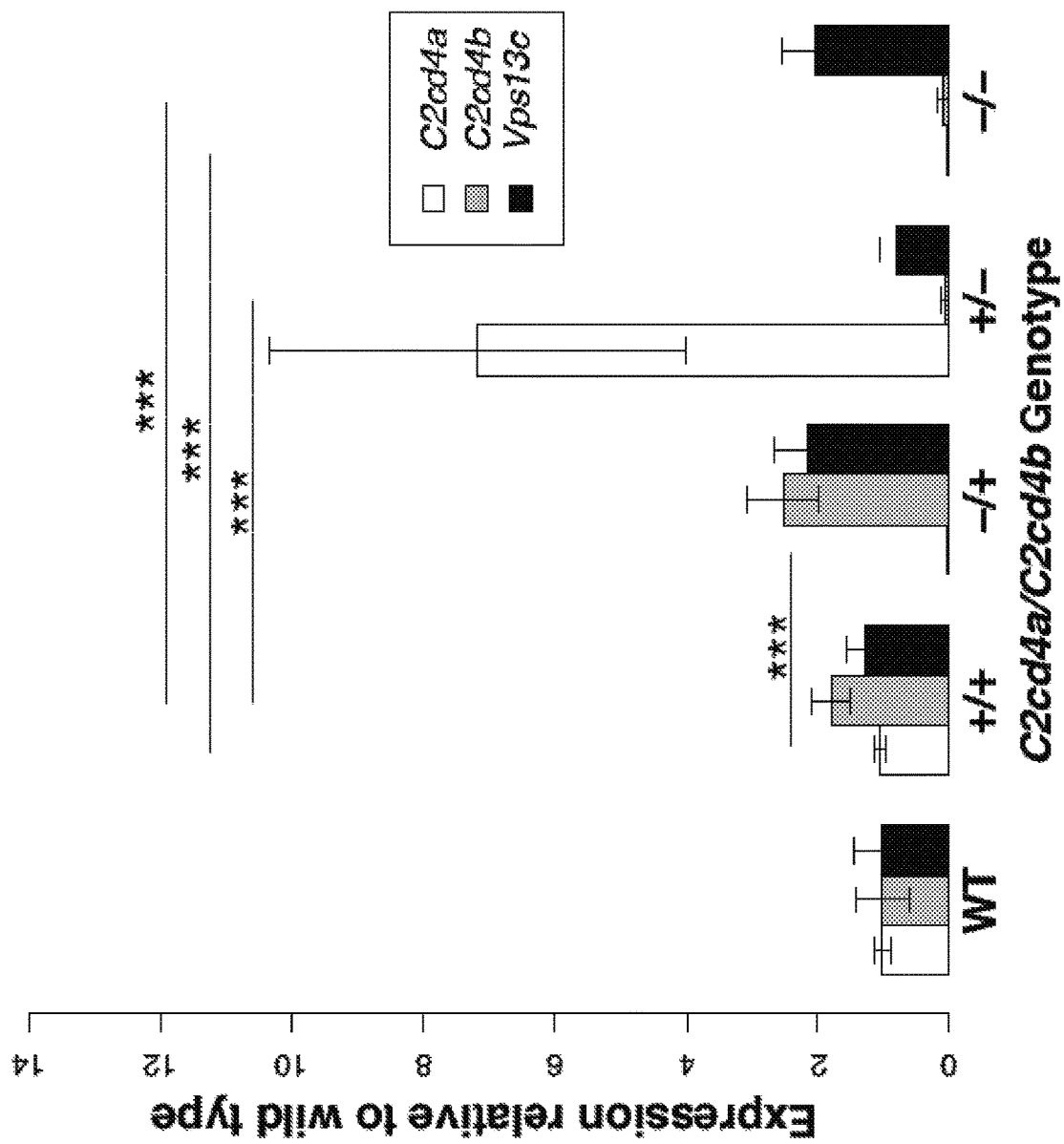
Figure 7D:
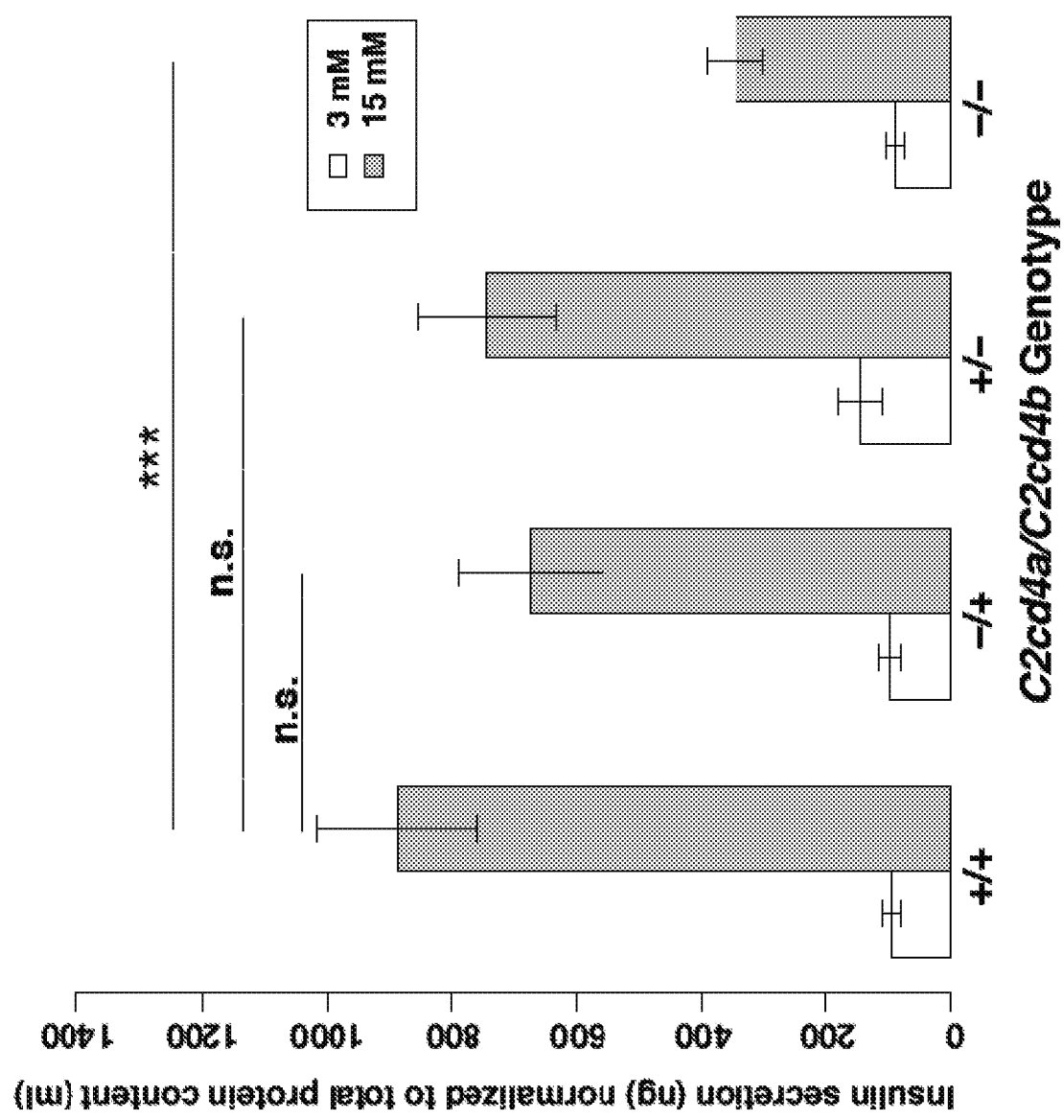
Figure 8A:
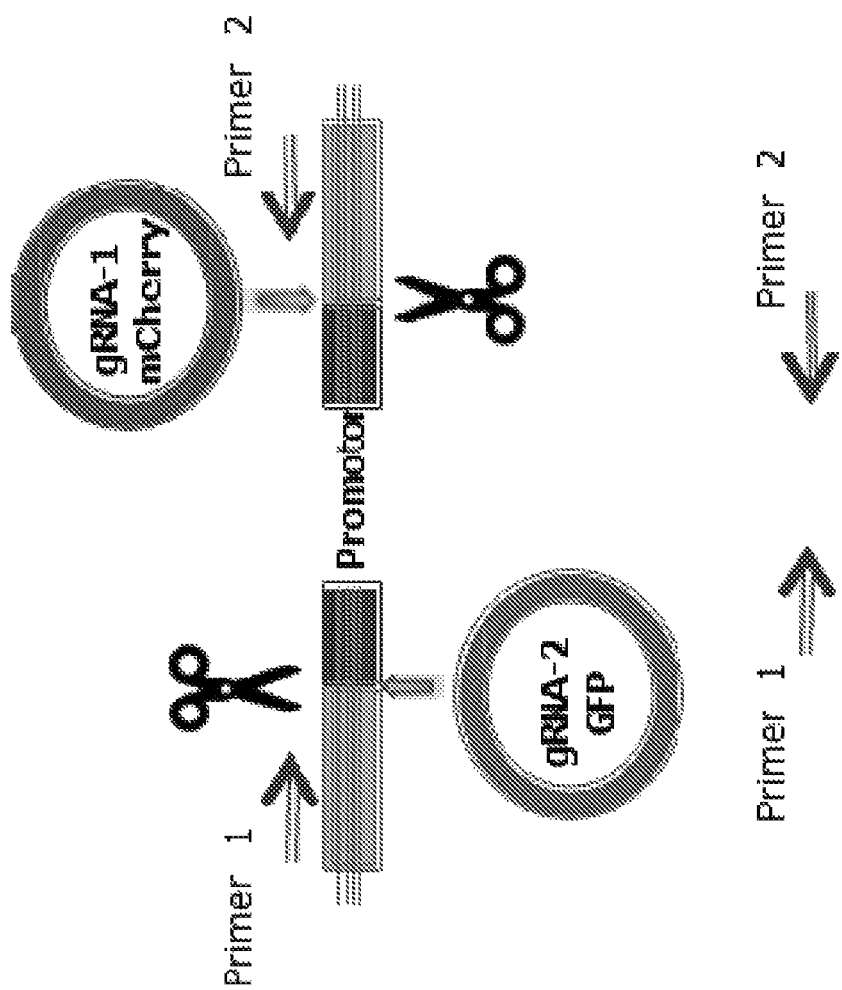
FIGS. 8A-8I. Strategy and confirmation of CRISPR/Cas9 genome editing of C2cd4a and C2cd4b loci to generate single and double mutants in INS-1(832/13) cells.
Figure 8B:
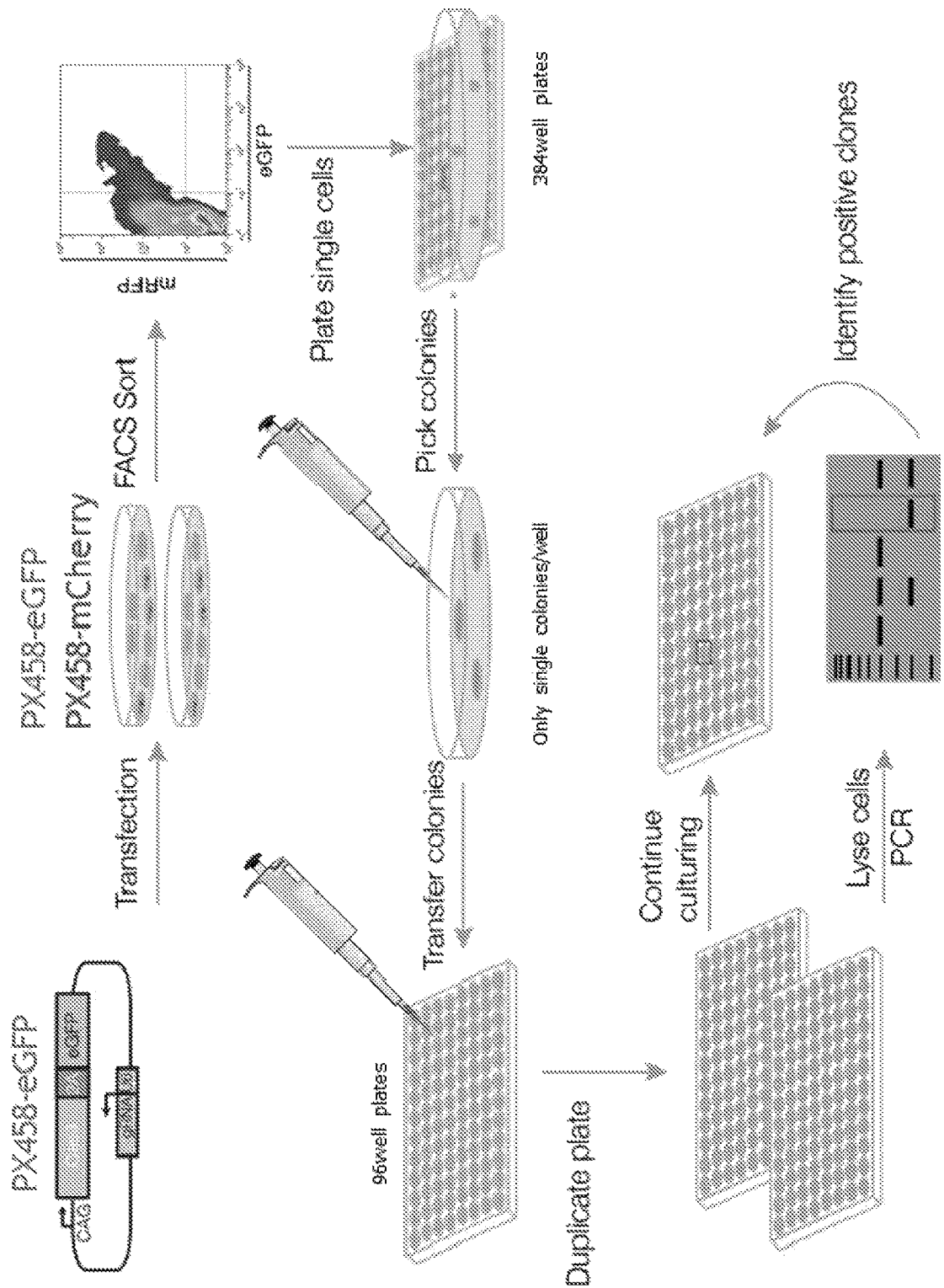

Guide RNA (gRNA) oligonucleotides (e.g., AGCCACTGGTATCGTCCCTT (SEQ ID NO: 1) (6358_C2cd4a_sgRNA1), TTCCAAAGGGACGATACCAG (SEQ ID NO: 2) (6359_C2cd4a_sgRNA2), CTGCTTTGACCGGCTCCCGG (SEQ ID NO: 8) (6360_C2cd4a_sgRNA3), CTGCTGCTTTGACCGGCTCC (SEQ ID NO: 3) (6361_C2cd4a_sgRNA4), CTGGATATGTTAAACGTAGG (SEQ ID NO: 4) (6362_C2cd4b_sgRNA1), CTTGGCATGTCCGTTTAGGA (SEQ ID NO: 5) (6363_C2cd4b_sgRNA2), CCTGGCCGTGCGCATCAAGG (SEQ ID NO: 6) (6364_C2cd4b_sgRNA3), and CCTTGATGCGCACGGCCAGG (SEQ ID NO: 7) (6365_C2cd4b_sgRNA4)) were designed to target the promoter region of C2cd4a and C2cd4b in the rat genome (rn5) using crispr.mit.edu (FIGS. 7A, 7B). Each gRNA targeting a site upstream of the C2cd4a or C2cd4b promoter was cloned into a pSpCas9(BB)-2A-GFP vector (PX458, Addgene, Cambridge, Massachusetts/USA), and gRNAs targeting a site downstream of the promotor for C2cd4a or C2cd4b were cloned into a previously reported, modified PX458 vector, in which GFP was replaced with mCherry (Roman et al., 2017; Diabetes) (FIG. 8A). The process for generating CRISPR-mediated deletions of each gene is depicted schematically in FIG. 8B. Each gRNA-containing GFP and mCherry vector were co-transfected in equimolar amounts into INS-1(832/13) cells using Lipofectamine 2000 (ThermoFisher Scientific, Waltham, Massachusetts/USA). Co-transfected INS-1(832/13) cells were incubated for 72 hours at 370 C with 5% $CO_2$.

Figure 8C:
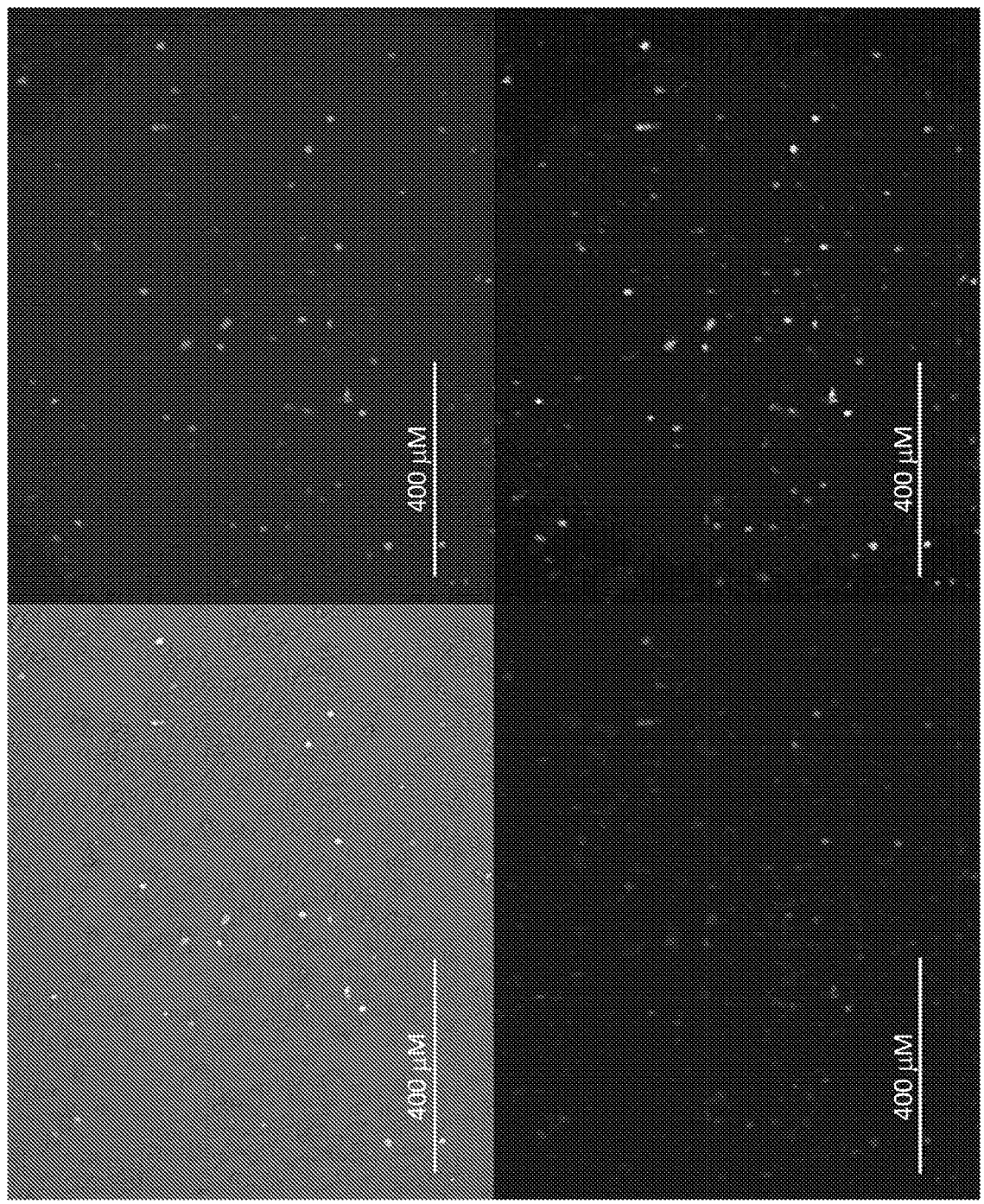
Figure 8D:
Figure 8E:
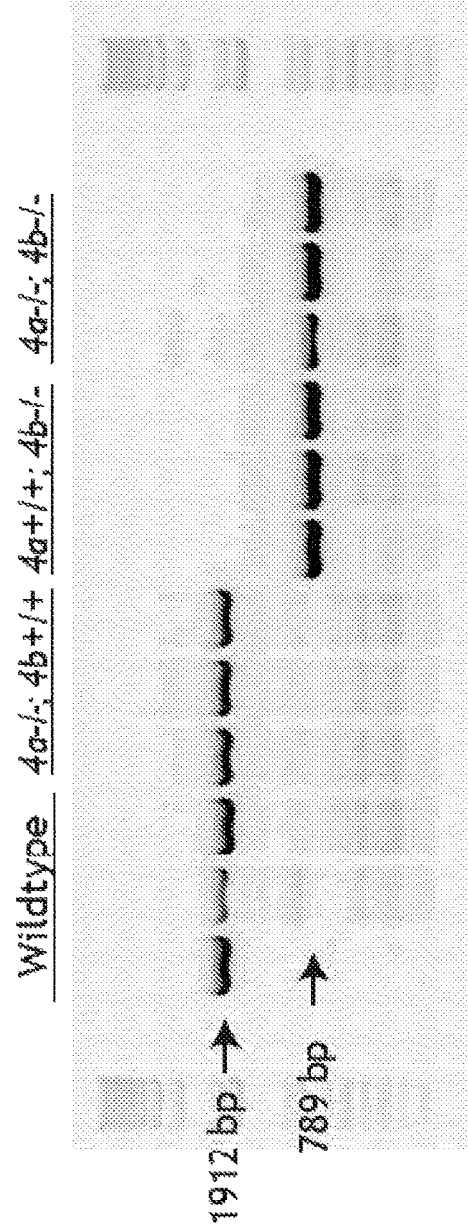
Figure 8F:
Figure 8G:
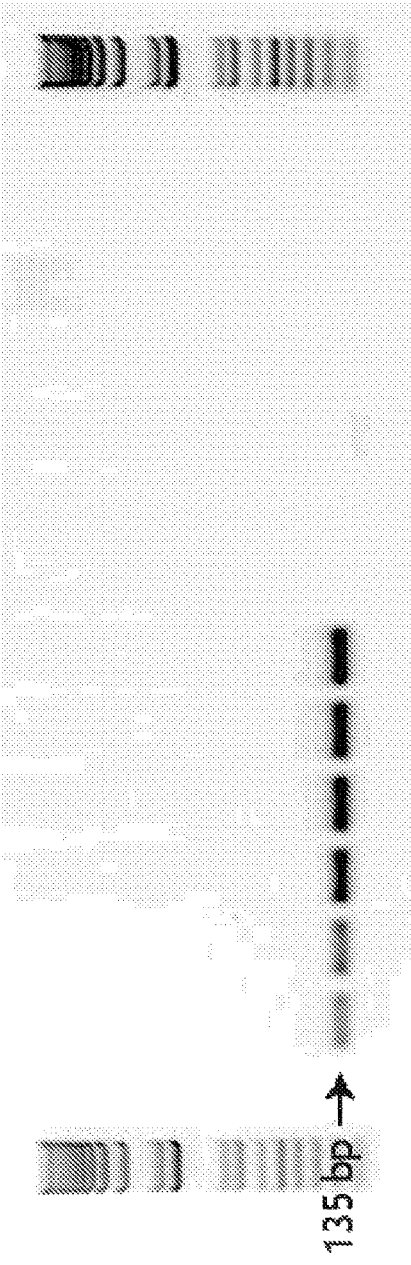
Figure 8H:
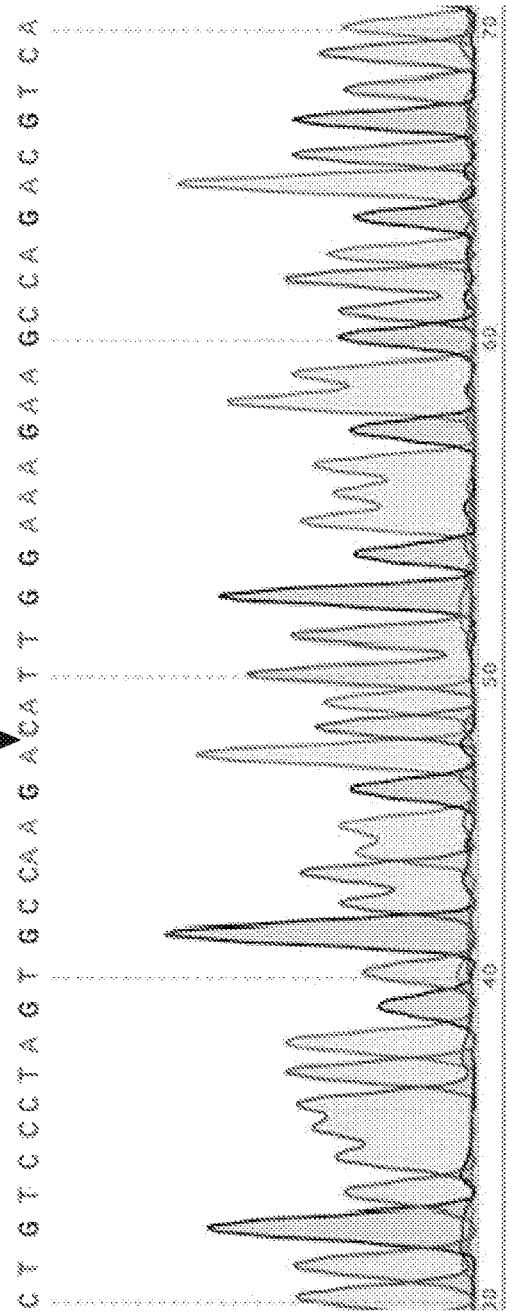
Figure 8I:
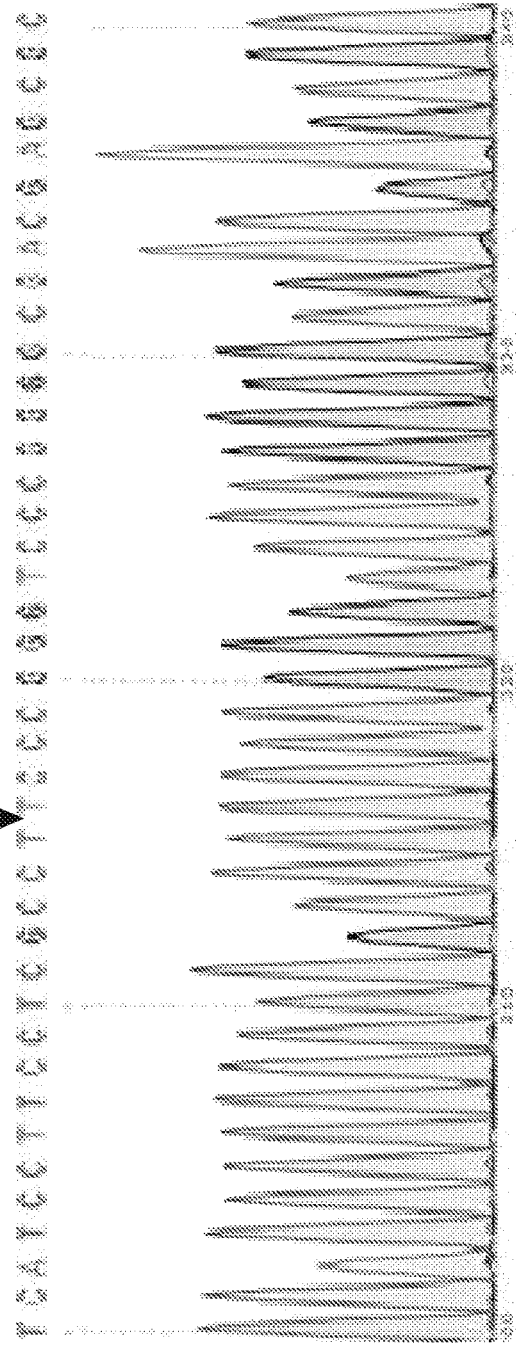

Fluorescence-activated single cell sorting (FACS) was used to place a single dual-positive (i.e., GFP+, mCherry+, as shown in FIG. 8C) cell into each well of a 384-well plate. INS-1(832/13) wildtype cells were also sorted as single cells into a 384-well plate to generate wildtype control clones. Sorted single cells were cultured and expanded for 21 days to generate clonal populations. Genomic DNA was extracted from each clone using QuickExtract (Epicentre, Madison, Wisconsin/USA). Diagnostic PCR was performed with primers spanning the gRNA-targeted regions (primer sequences found in accompanying supplemental table) in C2cd4a and C2cd4b to identify clones containing homozygous deletions of each targeted region. PCR detected homozygous 615 bp and 1123 bp deletions in C2cd4a (FIG. 8D) and C2cd4b (FIG. 8E), respectively, for seven and twenty-three clones. PCR using primers annealing to sequences within the deleted region independently confirmed absence of wildtype copies of the deleted C2cd4a or C2cd4b genomic DNA sequences in each deletion clone (FIG. 8F and FIG. 8G). Three clones each from $C2cd4a^{-/-}$ and $C2cd4b^{-/-}$ single gene deletions and from $C2cd4a^{-/-}$; $C2cd4b^{-/-}$ double deletions were selected for functional analyses, and Sanger sequencing was used to confirm the deletion and breakpoints in each clone (FIG. 8H and FIG. 8I). To generate $C2cd4a^{-/-}$; $C2cd4b^{-/-}$ double mutants, a single $C2cd4a^{-/-}$ clone was co-transfected with gRNAs targeting the C2cd4b locus, and cells were sorted, screened, and validated as performed for each single gene deletion. Validated homozygous deletions were assessed for effects on each gene's expression using qPCR and on insulin secretion as described below.

Reverse Transcriptase Quantitative PCR (RT-qPCR)

RNA was extracted using Trizol as previously described, and cDNA was synthesized using SuperScript IV (Invitrogen). Primer sequences can be found in the attached Supplemental Table. qPCR was performed using SYBR Green (Qiagen). C2cd4a, C2cd4b, and Vps13c transcript levels were normalized to that of the housekeeping/control gene Gapdh using the delta Ct method. C2CD4A, C2CD4B, and VPS13C expression plotted in FIG. 7C represents values relative to wild type expression of each gene. Glucose-stimulated insulin secretion (GSIS) assay Population doublings (PDs) 49-69 of each INS-1(832/13) clone were used for GSIS measurements. Cells were seeded at a density of 0.5×106/well in 1 ml medium in a 24-well plate. 18 hours prior to GSIS experiments, INS-1(832/13) culture medium containing 11.1 mmol/1 glucose was exchanged for fresh medium containing 5 mmol/1 glucose. GSIS was performed as previously described (Hohmeier et al., 2000). Briefly, cells were washed twice with HEPES balanced salt solution (HBSS) containing 3 mmol/1 glucose. After 2 hours, the buffer was switched to HBSS containing either 15 mmol/1 or 3 mmol/1 glucose and incubated for another 2 h. After 2 hours, 1 ml of supernatant was collected from each clone and glucose concentration. Cells were lysed in RIPA buffer (50 mM Tris HCl pH7.4, 1% NP40, 0.5% Na-Deoxycholate, 10% SDS, 150 mM NaCl, 2 mM EDTA+ Proteinase Inhibitor), and BCA assay (Pierce) was used to determine total protein levels for each clone and glucose concentration. Secreted insulin levels were measured in the supernatants using the rat high sensitivity ELISA kit (Mercodia). Insulin levels were normalized to total protein content for each clone and glucose concentration to determine insulin secretion as plotted in FIG. 7D.

REFERENCES

1. Mohlke, K. L. & Boehnke, M. Recent advances in understanding the genetic architecture of type 2 diabetes. *Hum. Mol. Genet.* 24, R85-92 (2015).

2. Ashcroft, F. M. & Rorsman, P. Diabetes mellitus and the R cell: the last ten years. *Cell* 148, 1160-1171 (2012).
3. Fuchsberger, C. et al. The genetic architecture of type 2 diabetes. *Nature* 536, 41-47 (2016).
4. Lawlor, N., Khetan, S., Ucar, D. & Stitzel, M. L. Genomics of Islet (Dys)function and Type 2 Diabetes. *Trends Genet.* TIG 33, 244-255 (2017).
5. Yamauchi, T. et al. A genome-wide association study in the Japanese population identifies susceptibility loci for type 2 diabetes at UBE2E2 and C2CD4A-C2CD4B. *Nat. Genet.* 42, 864-868 (2010).
6. Cui, B. et al. A genome-wide association study confirms previously reported loci for type 2 diabetes in Han Chinese. *PloS One* 6, e22353 (2011).
7. Shu, X. O. et al. Identification of new genetic risk variants for type 2 diabetes. *PLoS Genet.* 6, e1001127 (2010).
8. DIAbetes Genetics Replication And Meta-analysis (DIAGRAM) Consortium et al. Genome-wide trans-ancestry meta-analysis provides insight into the genetic architecture of type 2 diabetes susceptibility. *Nat. Genet.* 46, 234-244 (2014).
9. Dupuis, J. et al. New genetic loci implicated in fasting glucose homeostasis and their impact on type 2 diabetes risk. *Nat. Genet.* 42, 105-116 (2010).
10. Grarup, N. et al. The diabetogenic VPS13C/C2CD4A/C2CD4B rs7172432 variant impairs glucose-stimulated insulin response in 5,722 non-diabetic Danish individuals. *Diabetologia* 54, 789-794 (2011).
11. Strawbridge, R. J. et al. Genome-wide association identifies nine common variants associated with fasting proinsulin levels and provides new insights into the pathophysiology of type 2 diabetes. *Diabetes* 60, 2624-2634 (2011).
12. Huyghe, J. R. et al. Exome array analysis identifies new loci and low-frequency variants influencing insulin processing and secretion. *Nat. Genet.* 45, 197-201 (2013).
13. Saxena, R. et al. Genetic variation in GIPR influences the glucose and insulin responses to an oral glucose challenge. *Nat. Genet.* 42, 142-148 (2010).
14. Parker, S. C. J. et al. Chromatin stretch enhancer states drive cell-specific gene regulation and harbor human disease risk variants. *Proc. Natl. Acad. Sci. U.S.A* 110, 17921-17926 (2013).
15. Hnisz, D. et al. Super-enhancers in the control of cell identity and disease. *Cell* 155, 934-947 (2013).
16. Pasquali, L. et al. Pancreatic islet enhancer clusters enriched in type 2 diabetes risk-associated variants. *Nat. Genet.* 46, 136-143 (2014).
17. Roadmap Epigenomics Consortium et al. Integrative analysis of 111 reference human epigenomes. *Nature* 518, 317-330 (2015).
18. Stitzel, M. L., Kycia, I., Kursawe, R. & Ucar, D. Transcriptional Regulation of the Pancreatic Islet: Implications for Islet Function. *Curr. Diab. Rep.* 15, 66 (2015).
19. Stancikovi, A. et al. Changes in insulin sensitivity and insulin release in relation to glycemia and glucose tolerance in 6,414 Finnish men. *Diabetes* 58, 1212-1221 (2009).
20. Li, H. & Durbin, R. Fast and accurate short read alignment with Burrows-Wheeler transform. *Bioinforma. Oxf Engl.* 25, 1754-1760 (2009).
21. Howie, B., Fuchsberger, C., Stephens, M., Marchini, J. & Abecasis, G. R. Fast and accurate genotype imputation in genome-wide association studies through pre-phasing. *Nat. Genet.* 44, 955-959 (2012).
22. Delaneau, O., Marchini, J. & Zagury, J.-F. A linear complexity phasing method for thousands of genomes. *Nat. Methods* 9, 179-181 (2012).
23. Fuchsberger, C., Abecasis, G. R. & Hinds, D. A. minimac2: faster genotype imputation. *Bioinforma. Oxf Engl.* 31, 782-784 (2015).
24. Kang, H. M. et al. Variance component model to account for sample structure in genome-wide association studies. *Nat. Genet.* 42, 348-354 (2010).
25. Pruim, R. J. et al. LocusZoom: regional visualization of genome-wide association scan results. *Bioinforma. Oxf Engl.* 26, 2336-2337 (2010).
26. Miyazaki, J. et al. Establishment of a pancreatic beta cell line that retains glucose-inducible insulin secretion: special reference to expression of glucose transporter isoforms. *Endocrinology* 127, 126-132 (1990).
27. Hohmeier, H. E. et al. Isolation of INS-1-derived cell lines with robust ATP-sensitive K+ channel-dependent and-independent glucose-stimulated insulin secretion. *Diabetes* 49, 424-430 (2000).
28. Stitzel, M. L. et al. Global epigenomic analysis of primary human pancreatic islets provides insights into type 2 diabetes susceptibility loci. *Cell Metab.* 12, 443-455 (2010).
29. Buenrostro, J. D., Giresi, P. G., Zaba, L. C., Chang, H. Y. & Greenleaf, W. J. Transposition of native chromatin for fast and sensitive epigenomic profiling of open chromatin, DNA-binding proteins and nucleosome position. *Nat Meth* 10, 1213-1218 (2013).
30. Zhang, Y. et al. Model-based analysis of ChIP-Seq (MACS). *Genome Biol.* 9, R137 (2008).
31. Trapnell, C. et al. Differential gene and transcript expression analysis of RNA-seq experiments with TopHat and Cufflinks. *Nat. Protoc.* 7, 562-578 (2012).
32. Li, B. & Dewey, C. N. RSEM: accurate transcript quantification from RNA-Seq data with or without a reference genome. *BMC Bioinformatics* 12, 323 (2011).
33. Heinz, S. et al. Simple combinations of lineage-determining transcription factors prime cis-regulatory elements required for macrophage and B cell identities. *Mol. Cell* 38, 576-589 (2010).
34. Varshney, A. et al. Genetic regulatory signatures underlying islet gene expression and type 2 diabetes. *Proc. Natl. Acad. Sci. U.S.A* (2017). doi:10.1073/pnas.1621192114
35. Pique-Regi, R. et al. Accurate inference of transcription factor binding from DNA sequence and chromatin accessibility data. *Genome Res.* 21, 447-455 (2011).
36. Beals, C. R., Clipstone, N. A., Ho, S. N. & Crabtree, G. R. Nuclear localization of N F-ATc by a calcineurin-dependent, cyclosporin-sensitive intramolecular interaction. *Genes Dev.* 11, 824-834 (1997).
37. Aramburu, J. et al. Affinity-driven peptide selection of an NFAT inhibitor more selective than cyclosporin A. *Science* 285, 2129-2133 (1999).
38. Clipstone, N. A. & Crabtree, G. R. Identification of calcineurin as a key signalling enzyme in T-lymphocyte activation. *Nature* 357, 695-697 (1992).
39. 1000 Genomes Project Consortium et al. A global reference for human genetic variation. *Nature* 526, 68-74 (2015).
40. Benjamini, Y. & Hochberg, Y. Controlling the false discovery rate: a practical and powerful approach to multiple testing. *J. R. Stat. Soc.* Ser. B 57, 289-300 (1995).
41. Scott, L. J. et al. The genetic regulatory signature of type 2 diabetes in human skeletal muscle. *Nat. Commun.* 7, 11764 (2016).

42. Fadista, J. et al. Global genomic and transcriptomic analysis of human pancreatic islets reveals novel genes influencing glucose metabolism. *Proc. Natl. Acad. Sci. U.S.A* 111, 13924-13929 (2014).
43. Battle, A. et al. Characterizing the genetic basis of transcriptome diversity through RNA-sequencing of 922 individuals. *Genome Res.* 24, 14-24 (2014).
44. Dixon, J. R. et al. Topological domains in mammalian genomes identified by analysis of chromatin interactions. *Nature* 485, 376-380 (2012).
45. Fogarty, M. P., Cannon, M. E., Vadlamudi, S., Gaulton, K. J. & Mohlke, K. L. Identification of a regulatory variant that binds FOXA1 and FOXA2 at the CDC123/CAMK1D type 2 diabetes GWAS locus. *PLoS Genet.* 10, e1004633 (2014).
46. Eizirik, D. L. et al. The human pancreatic islet transcriptome: expression of candidate genes for type 1 diabetes and the impact of pro-inflammatory cytokines. *PLoS Genet.* 8, e1002552 (2012).
47. Arous, C., Ferreira, P. G., Dermitzakis, E. T. & Halban, P. A. Short term exposure of beta cells to low concentrations of interleukin-10 improves insulin secretion through focal adhesion and actin remodeling and regulation of gene expression. *J. Biol. Chem.* 290, 6653-6669 (2015).
48. Wellcome Trust Case Control Consortium et al. Bayesian refinement of association signals for 14 loci in 3 common diseases. *Nat. Genet.* 44, 1294-1301 (2012).
49. Wakefield, J. A Bayesian measure of the probability of false discovery in genetic epidemiology studies. *Am. J. Hum. Genet.* 81, 208-227 (2007).
50. Scott, R. A. et al. An Expanded Genome-Wide Association Study of Type 2 Diabetes in Europeans. *Diabetes* (2017). doi:10.2337/db16-1253
51. Whyte, W. A. et al. Master transcription factors and mediator establish super-enhancers at key cell identity genes. *Cell* 153, 307-319 (2013).
52. Denas, O. et al. Genome-wide comparative analysis reveals human-mouse regulatory landscape and evolution. *BMC Genomics* 16, 87 (2015).
53. Melé, M. et al. Human genomics. The human transcriptome across tissues and individuals. *Science* 348, 660-665 (2015).
54. GTEx Consortium. The Genotype-Tissue Expression (GTEx) project. *Nat. Genet.* 45, 580-585 (2013).
55. GTEx Consortium. Human genomics. The Genotype-Tissue Expression (GTEx) pilot analysis: multitissue gene regulation in humans. *Science* 348, 648-660 (2015).
56. Warton, K., Foster, N. C., Gold, W. A. & Stanley, K. K. A novel gene family induced by acute inflammation in endothelial cells. *Gene* 342, 85-95 (2004).
57. Halban, P. A. et al. j-cell failure in type 2 diabetes: postulated mechanisms and prospects for prevention and treatment. *Diabetes Care* 37, 1751-1758 (2014).
58. Ward, L. D. & Kellis, M. HaploReg v4: systematic mining of putative causal variants, cell types, regulators and target genes for human complex traits and disease. *Nucleic Acids Res.* 44, D877-881 (2016).
59. Goodyer, W. R. et al. Neonatal R cell development in mice and humans is regulated by calcineurin/NFAT. *Dev. Cell* 23, 21-34 (2012).
60. Heit, J. J. et al. Calcineurin/NFAT signalling regulates pancreatic beta-cell growth and function. *Nature* 443, 345-349 (2006).
61. Soleimanpour, S. A. et al. *Calcineurin signaling regulates human islet {beta}-cell survival. J. Biol. Chem.* 285, 40050-40059 (2010).
62. Lawrence, M. C., Bhatt, H. S. & Easom, R. A. NFAT regulates insulin gene promoter activity in response to synergistic pathways induced by glucose and glucagon-like peptide-1. *Diabetes* 51, 691-698 (2002).
63. Lawrence, M. C., Naziruddin, B., Levy, M. F., Jackson, A. & McGlynn, K. Calcineurin/nuclear factor of activated T cells and MAPK signaling induce TNF-{alpha}gene expression in pancreatic islet endocrine cells. *J. Biol. Chem.* 286, 1025-1036 (2011).
64. Lawrence, M. C. et al. NFAT targets signaling molecules to gene promoters in pancreatic (3-cells. *Mol. Endocrinol. Baltim. Md* 29, 274-288 (2015).
65. Bernal-Mizrachi, E., Cras-Mdneur, C., Ye, B. R., Johnson, J. D. & Permutt, M. A. Transgenic overexpression of active calcineurin in beta-cells results in decreased beta-cell 50 mass and hyperglycemia. *PloS One* 5, e11969 (2010).
66. Keller, M. P. et al. The Transcription Factor Nfatc2 Regulates j-Cell Proliferation and Genes Associated with Type 2 Diabetes in Mouse and Human Islets. *PLoS Genet.* 12, e1006466 (2016).
67. Aramburu, J. et al. Selective inhibition of NFAT activation by a peptide spanning the calcineurin targeting site of NFAT. *Mol. Cell* 1, 627-637 (1998).
68. Mehta, Z. B. et al. Changes in the expression of the type 2 diabetes-associated gene VPS13C in the 3-cell are associated with glucose intolerance in humans and mice. *Am. J. Physiol. Endocrinol. Metab.* 311, E488-507 (2016).
69. Gaulton, K. J. et al. Genetic fine mapping and genomic annotation defines causal mechanisms at type 2 diabetes susceptibility loci. *Nat. Genet.* 47, 1415-1425 (2015).
70. Northcott, P. A. et al. Enhancer hijacking activates GFI1 family oncogenes in medulloblastoma. *Nature* 511, 428-434 (2014).
71. Weischenfeldt, J. et al. Pan-cancer analysis of somatic copy-number alterations implicates IRS4 and IGF2 in enhancer hijacking. *Nat. Genet.* (2016). doi:10.1038/ng.3722
72. Cnop, M. et al. RNA sequencing identifies dysregulation of the human pancreatic islet transcriptome by the saturated fatty acid palmitate. *Diabetes* 63, 1978-1993 (2014).
73. Kluth, O. et al. Differential transcriptome analysis of diabetes-resistant and-sensitive mouse islets reveals significant overlap with human diabetes susceptibility genes. *Diabetes* 63, 4230-4238 (2014).

What is claimed is:

1. A mouse comprising homozygous deletions in C2 calcium-dependent domain containing 4A (C2cd4a$^{-/-}$) and C2 calcium-dependent domain containing 4B (C2cd4b$^{-/-}$), wherein C2cd4a$^{-/-}$ C2cd4b$^{-/-}$ cells of the mouse exhibit impaired glucose stimulated insulin secretion (GSIS).

2. The mouse of claim 1, wherein the mouse is an NZO/HILtJ mouse.

3. A method comprising administering to the mouse of claim 1 a therapy to treat diabetes.

4. The method of claim 3, wherein the therapy is for insulin resistance.

* * * * *